United States Patent
Liu et al.

(10) Patent No.: US 10,406,162 B2
(45) Date of Patent: Sep. 10, 2019

(54) SUBSTITUTED 2,3-DIHYDROIMIDAZO [1,2-C]QUINAZOLINE-CONTAINING COMBINATIONS

(71) Applicant: BAYER PHARMA AKTIENGESELLSCHAFT, Berlin (DE)

(72) Inventors: Ningshu Liu, Berlin (DE); Carol Pena, Basking Ridge, NJ (US); Michael Jeffers, Ridgewood, NJ (US); Isabelle Genvresse, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/556,908

(22) PCT Filed: Mar. 7, 2016

(86) PCT No.: PCT/EP2016/054727
§ 371 (c)(1),
(2) Date: Sep. 8, 2017

(87) PCT Pub. No.: WO2016/142312
PCT Pub. Date: Sep. 15, 2016

(65) Prior Publication Data
US 2018/0055851 A1    Mar. 1, 2018

Related U.S. Application Data

(60) Provisional application No. 62/130,418, filed on Mar. 9, 2015.

(51) Int. Cl.
*A61K 31/53*     (2006.01)
*A61K 31/505*   (2006.01)
(Continued)

(52) U.S. Cl.
CPC ............ *A61K 31/53* (2013.01); *A61K 31/519* (2013.01); *A61K 31/535* (2013.01);
(Continued)

(58) Field of Classification Search
CPC .............................. A61K 31/53; A61K 31/519
(Continued)

(56) References Cited

U.S. PATENT DOCUMENTS 7,511,041 B2    3/2009  Shimada
8,129,386 B2    3/2012  Shimada
(Continued)

FOREIGN PATENT DOCUMENTS

WO    WO2004029055 A1    4/2004
WO    WO-2008/070150      6/2008
(Continued)

OTHER PUBLICATIONS

Eskander, R., et al. (2014) "Exploiting the therapeutic potential of the PI3K-AKT-mTOR pathway in enriched populations of gynecologic malignancies," *Expert Rev. Clin. Pharmacol.*, 7(6):847-858.
(Continued)

*Primary Examiner* — Shengjun Wang
(74) *Attorney, Agent, or Firm* — Morrison & Foerster LLP

(57) ABSTRACT

The present invention relates to * combinations of: • component A: one or more 2,3-dihydroimidazo[1,2-c]quinazoline compounds of general formula (A1) or (A2), or a physiologically acceptable salt, solvate, hydrate or • stereoisomer thereof; • component B: one or more substituted 5-(1-benzothiophen-2-yl)pyrrolo[2,1-f][1,2,4]-triazin-4-amine compounds of general formula (B), or a physiologically acceptable salt, solvate, hydrate or stereoisomer thereof; • in which optionally some or all of the components are in the form of a pharmaceutical formulation which is
(Continued)

ready for use to be administered simultaneously, concurrently, separately or sequentially, • dependently of one another by the oral, intravenous, topical, local installations, • intraperitoneal or nasal route; * use of such combinations for the preparation of a medicament for the treatment or prophylaxis of a cancer; * a kit comprising such a combination; * use of biomarkers which is the loss of tumor suppressor PTEN or FBXW7, for predicting the sensitivity and/or resistance of a cancer patient to said compound and providing a rationale-based dosage to increase sensitivity and/or to overcome resistance; * a method of determining the loss of tumor suppressor PTEN or FBXW7; and a method for determining perturbations in PIK3CA, PIK3CB, PIK3CD, PIK3CG, PIK3R1, PIK3R2, PIK3R3, PIK3R4, PIK3R5, FGFR1, FGFR2, FGFR3 and/or FGFR4.

13 Claims, 5 Drawing Sheets

(51) Int. Cl.
| | | |
|---|---|---|
| A61K 31/519 | (2006.01) | |
| A61K 31/535 | (2006.01) | |
| A61K 31/5377 | (2006.01) | |
| C12Q 1/6886 | (2018.01) | |

(52) U.S. Cl.
CPC ........ *A61K 31/5377* (2013.01); *C12Q 1/6886* (2013.01); *C12Q 2600/156* (2013.01); *C12Q 2600/158* (2013.01)

(58) Field of Classification Search
USPC ........................................ 514/243, 257, 267
See application file for complete search history.

(56) References Cited

U.S. PATENT DOCUMENTS

| | | | |
|---|---|---|---|
| 8,466,283 | B2 | 6/2013 | Hentemann |
| 8,859,572 | B2 | 10/2014 | Hentemann et al. |
| 9,636,344 | B2 | 5/2017 | Peters |
| RE46,856 | E | 5/2018 | Hentemann |
| 9,999,623 | B2 | 6/2018 | Liu |
| 10,035,803 | B2 | 7/2018 | Peters et al. |
| 10,117,874 | B2 | 11/2018 | Liu |
| 2014/0072529 | A1 | 3/2014 | Peters |
| 2014/0243295 | A1 | 8/2014 | Liu |
| 2015/0141420 | A1 | 5/2015 | Liu et al. |
| 2018/0042929 | A1 | 2/2018 | Liu |
| 2018/0193349 | A1 | 7/2018 | Liu et al. |
| 2018/0282337 | A1 | 10/2018 | Peters et al. |

FOREIGN PATENT DOCUMENTS

| | | |
|---|---|---|
| WO | WO2010034414 A1 | 4/2010 |
| WO | WO-2011/128407 | 10/2011 |
| WO | WO-2012/136553 | 10/2012 |
| WO | WO2012136549 A1 | 10/2012 |
| WO | WO-2013/087578 | 6/2013 |
| WO | WO2014166820 A1 | 10/2014 |
| WO | WO-2014/191938 | 12/2014 |
| WO | WO2015082322 A1 | 6/2015 |
| WO | WO2009091550 A3 | 3/2016 |
| WO | WO2016071426 A1 | 5/2016 |
| WO | WO2016071435 A3 | 6/2016 |
| WO | WO2016142313 A1 | 9/2016 |
| WO | WO2017134000 A1 | 8/2017 |
| WO | WO2017134030 A1 | 8/2017 |
| WO | WO2017153220 A1 | 9/2017 |

OTHER PUBLICATIONS

International Search Report dated May 17, 2016, for PCT Application No. PCT/EP2016/054727, filed on Jul. 3, 2016, 6 pages.
Katoh, M., et al. (2014) "FGF Receptors: Cancer Biology and Therapeutics," *Medicinal Research Reviews*, 34(2):280-300.
Konecny, G., et al. (May 2013) "Activity of the Fibroblast Growth Factor Receptor Inhibitors Dovitinib (TKI258) and NVP-BGJ398 in Human Endometrial Cancer Cells," *Mol. Cancer Ther.*, 12(5):632-642.
Liu, N., et al. (Nov. 2013) "BAY 80/6946 Is a Highly Selective Intravenous PI3K Inhibitor with Potent p110α and p110δ Activities in Tumor Cell Lines and Xenograft Models," *Mol. Cancer Ther.*, 12(11):2319-2330.
Singh, C., et al. (Feb. 2015) "Target Next Generation Sequencing (NGS) for the Identification of Clinically Actionable Mutations in Advanced Stage/Recurrent Endometrial Carcinoma (EC)," *Modern Pathology*, 28(2s):307A.
Stelloo, E., et al. (2015) "Refining prognosis and identifying targetable pathways for high-risk endometrial cancer; a TransPORTEC initiative," Modern Pathology, 28(6):836-844.
U.S. Appl. No. 14/009,599, filed internationally on Mar. 29, 2012, for Peters et al. (Also published as US-20140072529, cited herewith) (U.S. Patent Application is not submitted herewith pursuant to the waiver of 37 C.F.R. § 1.98(a)(2)(iii) issued by the Office dated Sep. 21, 2004.).
U.S. Appl. No. 14/009,751, filed internationally on Mar. 29, 2012, for Liu et al. (Also published as US-20140243295, cited herewith) (U.S. Patent Application is not submitted herewith pursuant to the waiver of 37 C.F.R. § 1.98(a)(2)(iii) issued by the Office dated Sep. 21, 2004.).
U.S. Appl. No. 14/500,484, filed Sep. 29, 2014, for Liu et al. (Also published as US-20150141420, cited herewith) (U.S. Patent Application is not submitted herewith pursuant to the waiver of 37 C.F.R. § 1.98(a)(2)(iii) issued by the Office dated Sep. 21, 2004.).
U.S. Appl. No. 15/524,581, filed internationally on Mar. 5, 2015, for Peters et al. (Also published as US-20180282337, cited herewith) (U.S. Patent Application is not submitted herewith pursuant to the waiver of 37 C.F.R. § 1.98(a)(2)(iii) issued by the Office dated Sep. 21, 2004.).
U.S. Appl. No. 15/557,036, filed internationally on Mar. 7, 2016, for Liu et al. (Also published as US-20180042929, cited herewith) (U.S. Patent Application is not submitted herewith pursuant to the waiver of 37 C.F.R. § 1.98(a)(2)(iii) issued by the Office dated Sep. 21, 2004.).
U.S. Appl. No. 15/861,555, filed Jan. 3, 2018, for Liu et al. (Also published as US-20180193349, cited herewith) (U.S. Patent Application is not submitted herewith pursuant to the waiver of 37 C.F.R. § 1.98 (a)(2)(iii) issued by the Office dated Sep. 21, 2004.).
U.S. Appl. No. 16/074,037, filed internationally on Jan. 31, 2017, for Pena et al. (U.S. Patent Application is not submitted herewith pursuant to the waiver of 37 C.F.R. § 1.98(a)(2)(iii) issued by the Office dated Sep. 21, 2004.).
U.S. Appl. No. 16/074,728, filed internationally on Jan. 30, 2017, for Liu et al. (U.S. Patent Application is not submitted herewith pursuant to the waiver of 37 C.F.R. § 1.98(a)(2)(iii) issued by the Office dated Sep. 21, 2004.).
U.S. Appl. No. 16/082,712, filed internationally on Mar. 1, 2017, for Schwarz et al. (U.S. Patent Application is not submitted herewith pursuant to the waiver of 37 C.F.R. § 1.98(a)(2)(iii) issued by the Office dated Sep. 21, 2004.).

SUBSTITUTED 2,3-DIHYDROIMIDAZO[1,2-C]QUINAZOLINE-CONTAINING COMBINATIONS

CROSS REFERENCE TO RELATED APPLICATIONS

This application is a National Phase application under 35 U.S.C. § 371 of International Application No. PCT/EP2016/054727, filed Mar. 7, 2016, which claims priority benefit of U.S. Application No. 62/130,418, filed Mar. 9, 2015, the disclosures of each of which are hereby incorporated by reference in their entireties for all purposes.

The present invention relates:
to combinations of:
component A: one or more 2,3-dihydroimidazo[1,2-c]quinazoline compounds of general formula (A1) or (A2), or a physiologically acceptable salt, solvate, hydrate or stereoisomer thereof;
component B: one or more substituted 5-(1-benzothiophen-2-yl)pyrrolo[2,1-f][1,2,4]-triazin-4-amine compounds of general formula (B), or a physiologically acceptable salt, solvate, hydrate or stereoisomer thereof; and, optionally,
component C: one or more further pharmaceutical agents;
in which optionally either or both of components A and B in any of the above-mentioned combinations are in the form of a pharmaceutical formulation which is ready for use to be administered simultaneously, concurrently, separately or sequentially. The components may be administered independently of one another by the oral, intravenous, topical, local installations, intraperitoneal or nasal route.

Another aspect of the present invention relates to the use of such combinations as described supra for the preparation of a medicament for the treatment or prophylaxis of a cancer, particularly endometrial cancer (hereinafter abbreviated to "EC"), particularly 1st line, 2nd line, relapsed, refractory, type I or type II EC, or endometriosis.

Further, the present invention relates to:
a kit comprising:
a combination of:
component A: one or more 2,3-dihydroimidazo[1,2-c]quinazoline compounds of general formula (A1) or (A2), or a physiologically acceptable salt, solvate, hydrate or stereoisomer thereof;
component B: one or more substituted 5-(1-benzothiophen-2-yl)pyrrolo[2,1-f][1,2,4]-triazin-4-amine compounds of general formula (B), or a physiologically acceptable salt, solvate, hydrate or stereoisomer thereof;
in which optionally either or both of said components (A) and (B) in any of the above-mentioned combinations are in the form of a pharmaceutical formulation which is ready for use to be administered simultaneously, concurrently, separately or sequentially. The components may be administered independently of one another by the oral, intravenous, topical, local installations, intraperitoneal or nasal route.

Further, the present invention relates to:
use of biomarkers, such as the loss of tumor suppressor PTEN or FBXW7, either alone or in combination with another form of PI3K pathway activation selected from perturbation of any of the following alone or in combination: mutation in PIK3CA, PIK3CB, PIK3CD, PIK3CG, PIK3R1, PIK3R2, PIK3R3, PIK3R4, PIK3R5, FGFR1, FGFR2, FGFR3 and/or FGFR4; PTEN-loss and alteration of PIK3CA, PIK3CB, PIK3CD, PIK3CG, PIK3R1, PIK3R2, PIK3R3, PIK3R4, PIK3R5, FGFR1, FGFR2, FGFR3 and/or FGFR4 which may be measured at either the protein level, mRNA level, or DNA level,
for predicting the sensitivity and/or resistance of a patient with endometrial cancer (hereinafter abbreviated to "EC"), particularly 1st line, 2nd line, relapsed, refractory, type I or type II EC, or endometriosis, to a combination of a component A and a component B as defined herein, thus providing rationale-based dosage as defined herein to overcome said resistance of a patient with endometrial cancer (hereinafter abbreviated to "EC"), particularly 1st line, 2nd line, relapsed, refractory, type I or type II EC, or endometriosis, to a combination of a component A and a component B as defined herein (patient stratification);
a method of determining the loss of tumor suppressor PTEN or FBXW7; and
a method for determining perturbations in PIK3CA, PIK3CB, PIK3CD, PIK3CG, PIK3R1, PIK3R2, PIK3R3, PIK3R4, PIK3R5, FGFR1, FGFR2, FGFR3 and/or FGFR4. PTEN loss and alteration of PIK3CA, PIK3CB, PIK3CD, PIK3CG, PIK3R1, PIK3R2, PIK3R3, PIK3R4, PIK3R5, FGFR1, FGFR2, FGFR3 and/or FGFR4.

BACKGROUND OF THE INVENTION

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

The PI3K signaling pathway is one of the prominent pathways that promote tumor cell survival. PI3K is activated by many cancer related receptor tyrosine kinases (e.g. PDGFR, EGFR, HER2/3, or IGF-1R), cell adhesion molecules, GPCR, and oncogenic proteins (such as Ras). The PI3K pathway activation by genetic alteration of PI3K (activation mutation and/or amplification) and/or loss-of-function of the tumour suppressor PTEN are frequently found in many tumors. Furthermore, activation of PI3K is one of the major mechanisms causing the resistance of tumors to radio-, chemo- and targeted therapeutics.

Once PI3K is activated, it catalyzes the generation of PIP3 from PIP2. The biological active PIP3 binds to the pleckstrin homology (PH) domains of PDK-1, AKT, and other PH-domain containing proteins, such as Rho and PLC. As the consequence of binding to PIP3, these proteins are translocated to the cell membrane and are subsequently activated to induce tumor cell proliferation, survival, invasion and migration.

Fibroblast growth factors (FGFs) and their receptors (FGFRs) drive crucial developmental signaling pathways, which are responsible for many functions of the tumor cells, including cell proliferation, survival and migration through downstream signaling pathways mediated by PLCγ/PKC, RAS/MAPK, PI3K/AKT, and STATs. FGFR signaling pathways also regulate tumor stromal cells as well as tumor angiogenesis. There are several types of genetic evidence that support an oncogenic function of FGFRs: gene amplifications, activating mutations, chromosomal translocations and aberrant splicing at the post-transcriptional level.

Endometrial cancer (EC) is the most common gynecologic malignancy in industrialized countries, with an incidence rate of 12.9 per 100,000 women per year. Early-stage EC (stage I or II) can be effectively treated with surgery, while treatment of recurrent or high grade metastatic disease is limited to cytotoxic chemotherapy, e.g. paclitaxel and carboplatin. In addition, for recurrent EC, there are still no agreement and no definitive drugs of choice in spite of the poor prognosis of this subset of patients. It is noteworthy that the available chemotherapies do not provide long-term disease control, and many patients demonstrate intrinsic resistance and significant toxicities to these therapies. As such, it remains an important unmet medical need for recurrent EC. The successful management of these patients depends on the identification and understanding of molecular mechanisms underlying the initiation and progression of EC to achieve a more tailored therapy, based on the biological tumor profile.

As described in the present text, the anti-tumor efficacy of the PI3K inhibitor copanlisib was investigated in preclinical tumor models in vitro and in vivo in combination. The combination of the PI3K inhibitor copanlisib with FGFR inhibitors was found to be synergistic, which led to tumor regression in preclinical tumor model in vivo compared to tumor progression or tumor stasis in animals treated with monotherapy of each agent.

Unexpectedly, and this represents a basis of the present invention, when combinations of:
component A: a 2,3-dihydroimidazo[1,2-c]quinazoline compound of general formula (A1) or (A2), or a physiologically acceptable salt, solvate, hydrate or stereoisomer thereof, as described and defined herein; with
component B: a substituted 5-(1-benzothiophen-2-yl)pyrrolo[2,1-f][1,2,4]-triazin-4-amine compounds of general formula (B), or a physiologically acceptable salt, solvate, hydrate or stereoisomer thereof, as described and defined herein;
were evaluated for the treatment of endometrial cancer (hereinafter abbreviated to "EC"), particularly 1st line, 2nd line, relapsed, refractory, type I or type II EC, or endometriosis, synergistically increased anti-tumor activities were demonstrated with these combinations compared to each monotherapy, providing a fundamental rationale for the clinical combination therapy using PI3K inhibitors-FGFR inhibitors.

To the Applicant's knowledge, no generic or specific disclosure or suggestion in the prior art is known that either combinations of:
component A: one or more 2,3-dihydroimidazo[1,2-c]quinazoline compounds of general formula (A1) or (A2), or a physiologically acceptable salt, solvate, hydrate or stereoisomer thereof;
component B: one or more substituted 5-(1-benzothiophen-2-yl)pyrrolo[2,1-f][1,2,4]-triazin-4-amine compounds of general formula (B), or a physiologically acceptable salt, solvate, hydrate or stereoisomer thereof;
in which optionally either or both of said components A and B of any of the above-mentioned combinations are in the form of a pharmaceutical formulation which is ready for use to be administered simultaneously, concurrently, separately or sequentially, would be effective in the treatment or prophylaxis of cancer, particularly endometrial cancer (hereinafter abbreviated to "EC"), particularly 1st line, 2nd line, relapsed, refractory, type I or type II EC, or endometriosis.

Based on the action of the testing compounds described in this invention, the combinations of the present invention as described and defined herein, show a beneficial effect in the treatment of cancer, particularly endometrial cancer (hereinafter abbreviated to "EC"), particularly 1st line, 2nd line, relapsed, refractory, type I or type II EC, or endometriosis.

Accordingly, in accordance with a first aspect, the present invention relates: to combinations of:

component A: one or more 2,3-dihydroimidazo[1,2-c]quinazoline compounds of general formula (A1) or (A2), or a physiologically acceptable salt, solvate, hydrate or stereoisomer thereof;
component B: one or more substituted 5-(1-benzothiophen-2-yl)pyrrolo[2,1-f][1,2,4]-triazin-4-amine compounds of general formula (B), or a physiologically acceptable salt, solvate, hydrate or stereoisomer thereof;
in which optionally either or both of said components A and B) of any of the above-mentioned combinations are in the form of a pharmaceutical formulation which is ready for use to be administered simultaneously, concurrently, separately or sequentially. The components may be administered independently of one another by the oral, intravenous, topical, local installations, intraperitoneal or nasal route.

In accordance with a second aspect, of the present invention relates to the use of any of such combinations as described supra for the preparation of a medicament for the treatment or prophylaxis of a cancer, particularly endometrial cancer (hereinafter abbreviated to "EC"), particularly 1st line, 2nd line, relapsed, refractory, type I or type II EC, or endometriosis.

Further, in accordance with a third aspect, the present invention relates to a kit comprising:
a combination of:
component A: one or more 2,3-dihydroimidazo[1,2-c]quinazoline compounds of general formula (A1) or (A2), or a physiologically acceptable salt, solvate, hydrate or stereoisomer thereof;
component B: one or more substituted 5-(1-benzothiophen-2-yl)pyrrolo[2,1-f][1,2,4]-triazin-4-amine compounds of general formula (B), or a physiologically acceptable salt, solvate, hydrate or stereoisomer thereof;
in which optionally either or both of components A and B in any of the above-mentioned combinations are in the form of a pharmaceutical formulation which is ready for use to be administered simultaneously, concurrently, separately or sequentially. The components may be administered independently of one another by the oral, intravenous, topical, local installations, intraperitoneal or nasal route.

Further, in accordance with a fourth aspect, the present invention relates:
to use of biomarkers, such as the loss of tumor suppressor PTEN or FBXW7, either alone or in combination with another form of PI3K pathway activation selected from perturbation of any of the following alone or in combination: mutation in PIK3CA, PIK3CB, PIK3CD, PIK3CG, PIK3R1, PIK3R2, PIK3R3, PIK3R4, PIK3R5, FGFR1, FGFR2, FGFR3 and/or FGFR4; PTEN-loss and alteration of PIK3CA, PIK3CB, PIK3CD, PIK3CG, PIK3R1, PIK3R2, PIK3R3, PIK3R4, PIK3R5, FGFR1, FGFR2, FGFR3 and/or FGFR4 which may be measured at either the protein level, mRNA level, or DNA level,
for predicting the sensitivity and/or resistance of a patient with endometrial cancer (hereinafter abbreviated to "EC"), particularly 1st line, 2nd line, relapsed, refractory, type I or type II EC, or endometriosis, to a combination of a component A and a component B as defined herein, thus providing rationale-based dosage as defined herein to overcome said resistance of a patient with endometrial cancer (hereinafter abbreviated to "EC"), particularly 1st line, 2nd line, relapsed, refractory, type I or type II EC, or endometriosis, to a combination of a component A and a component B as defined herein (patient stratification);
to a method of determining the loss of tumor suppressor PTEN or FBXW7; and to a method for determining perturbations in PIK3CA, PIK3CB, PIK3CD, PIK3CG, PIK3R1, PIK3R2, PIK3R3, PIK3R4, PIK3R5, FGFR1, FGFR2, FGFR3 and/or FGFR4. PTEN loss and alteration of PIK3CA, PIK3CB, PIK3CD, PIK3CG, PIK3R1, PIK3R2, PIK3R3, PIK3R4, PIK3R5, FGFR1, FGFR2, FGFR3 and/or FGFR4.

DETAILED DESCRIPTION OF THE INVENTION

Figure 1:
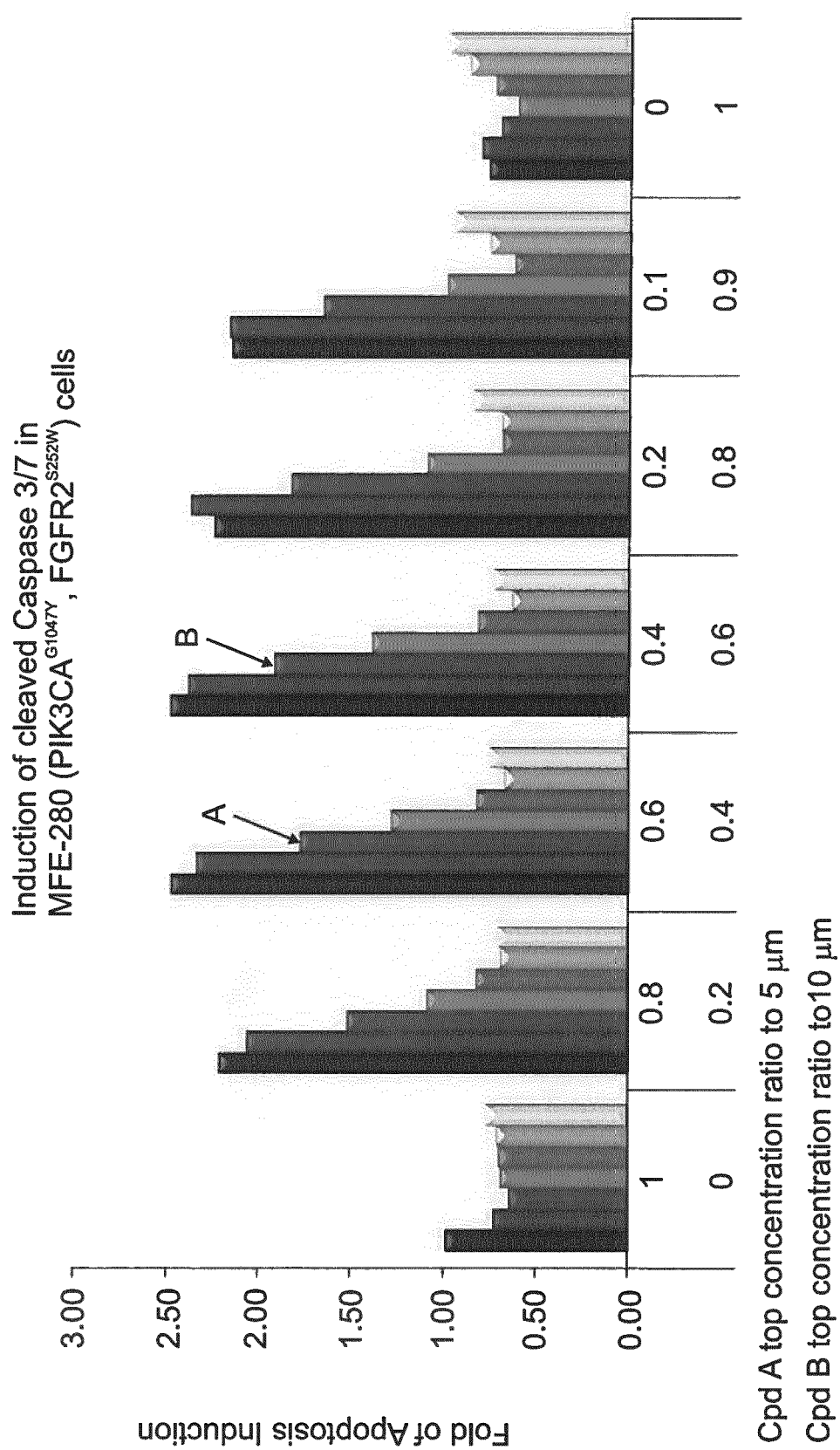
FIG. 1 shows a graph of apoptosis induction by PI3K inhibitor compound A (copanlisib) and/or FGFR inhibitor compound B in MFE-280 cells.

In accordance with an embodiment of the above-mentioned aspects of the present invention, said combinations are of:

component A: which is one or more 2,3-dihydroimidazo[1,2-c]quinazoline compounds of general formula (A1):

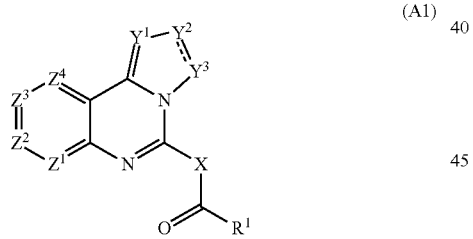

(A1)

wherein
X represents $CR^5R^6$ or NH;
$Y^1$ represents $CR^3$ or N;
Chemical bond between $Y^2 Y^2 = Y^3 Y^3$ represents a single bond or double bond,
with the proviso that when the $Y^2 Y^2 = Y^3 Y^3$ represents a double bond,
$Y^2$ and $Y^3$ independently represent $CR^4$ or N, and
when $Y^2 Y^2 = Y^3 Y^3$ represents a single bond, $Y^2$ and $Y^3$ independently represent $CR^3R^4$ or $NR^4$;
$Z^1$, $Z^2$, $Z^3$ and $Z^4$ independently represent CH, $CR^2$ or N;
$R^1$ represents aryl optionally having 1 to 3 substituents selected from $R^{11}$, $C_{3-8}$ cycloalkyl optionally having 1 to 3 substituents selected from $R^{11}$,
$C_{1-6}$ alkyl optionally substituted by
aryl, heteroaryl, $C_{1-6}$ alkoxyaryl, aryloxy, heteroaryloxy or one or more halogen,
$C_{1-6}$ alkoxy optionally substituted by
carboxy, aryl, heteroaryl, $C_{1-6}$ alkoxyaryl, aryloxy, heteroaryloxy or one or more halogen,
or
a 3 to 15 membered mono- or bi-cyclic heterocyclic ring that is saturated or unsaturated, and contains 1 to 3 heteroatoms selected from the group consisting of N, O and S, and optionally having 1 to 3 substituents selected from $R^{11}$
wherein
$R^{11}$ represents
halogen, nitro, hydroxy, cyano, carboxy, amino, N—($C_{1-6}$alkyl)amino, N-(hydroxy$C_{1-6}$alkyl)amino, N,N-di($C_{1-6}$alkyl)amino, N—($C_{1-6}$acyl)amino, N-(formyl)-N—($C_{1-6}$alkyl)amino, N—($C_{1-6}$alkanesulfonyl) amino, N-(carboxy$C_{1-6}$alkyl)-N—($C_{1-6}$ alkyl)amino, N—($C_{1-6}$alkoxycabonyl)amino, N—[N,N-di($C_{1-6}$alkyl)amino methylene]amino, N—[N,N-di($C_{1-6}$alkyl)amino ($C_{1-6}$ alkyl)methylene]amino, N—[N,N-di($C_{1-6}$alkyl)amino $C_{2-6}$alkenyl]amino, aminocarbonyl, N—($C_{1-6}$alkyl)aminocarbonyl, N,N-di($C_{1-6}$alkyl)aminocarbonyl, $C_{3-8}$cycloalkyl, $C_{1-6}$alkylthio, $C_{1-6}$alkanesulfonyl, sulfamoyl, $C_{1-6}$alkoxycarbonyl,
N-arylamino wherein said aryl moiety is optionally having 1 to 3 substituents selected from $R^{101}$, N-(aryl $C_{1-6}$alkyl)amino wherein said aryl moiety is optionally having 1 to 3 substituents selected from $R^{101}$, aryl $C_{1-6}$alkoxycarbonyl wherein said aryl moiety is optionally having 1 to 3 substituents selected from $R^{101}$,
$C_{1-6}$alkyl optionally substituted by mono-, di- or tri-halogen, amino, N—($C_{1-6}$alkyl)amino or N,N-di ($C_{1-6}$ alkyl)amino,
$C_{1-6}$alkoxy optionally substituted by mono-, di- or tri-halogen, N—($C_{1-6}$alkyl)sulfonamide, or N-(aryl) sulfonamide,
or
a 5 to 7 membered saturated or unsaturated ring having 1 to 3 heteroatoms selected from the group consisting of O, S and N, and optionally having 1 to 3 substituents selected from $R^{101}$
wherein
$R^{101}$ represents
halogen, carboxy, amino, N—($C_{1-6}$ alkyl)amino, N,N-di($C_{1-6}$alkyl)amino, aminocarbonyl, N—($C_{1-6}$alkyl) aminocarbonyl, N,N-di($C_{1-6}$alkyl)aminocarbonyl, pyridyl,
$C_{1-6}$ alkyl optionally substituted by cyano or mono- di- or tri-halogen,
or
$C_{1-6}$alkoxy optionally substituted by cyano, carboxy, amino, N—($C_{1-6}$ alkyl)amino, N,N-di($C_{1-6}$alkyl) amino, aminocarbonyl, N—($C_{1-6}$alkyl)aminocarbonyl, N,N-di($C_{1-6}$alkyl)aminocarbonyl or mono-, di- or tri-halogen;
$R^2$ represents hydroxy, halogen, nitro, cyano, amino, N—($C_{1-6}$alkyl)amino, N,N-di($C_{1-6}$alkyl)amino, N-(hydroxy$C_{1-6}$alkyl)amino, N-(hydroxy$C_{1-6}$alkyl)-N— ($C_{1-6}$ alkyl)amino, $C_{1-6}$ acyloxy, amino$C_{1-6}$acyloxy, $C_{2-6}$alkenyl, aryl,
a 5-7 membered saturated or unsaturated heterocyclic ring having 1 to 3 heteroatoms selected from the group consisting O, S and N, and optionally substituted by
hydroxy, $C_{1-6}$ alkyl, $C_{1-6}$ alkoxy, oxo, amino, amino $C_{1-6}$alkyl, N—($C_{1-6}$alkyl)amino, N,N-di($C_{1-6}$alkyl) amino, N—($C_{1-6}$ acyl)amino, N—($C_{1-6}$alkyl)carbonylamino, phenyl, phenyl $C_{1-6}$ alkyl, carboxy, $C_{1-6}$alkoxycarbonyl, aminocarbonyl, N—($C_{1-6}$alkyl)aminocarbonyl, or N,N-di($C_{1-6}$alkyl)amino,
—C(O)—$R^{20}$
wherein
$R^{20}$ represents $C_{1-6}$ alkyl, $C_{1-6}$ alkoxy, amino, N—($C_{1-6}$ alkyl)amino, N,N-di($C_{1-6}$alkyl)amino, N—($C_{1-6}$ acyl)amino, or a 5-7 membered saturated or unsaturated heterocyclic ring having 1 to 3 heteroatoms selected from the group consisting O, S and N, and optionally substituted by $C_{1-6}$ alkyl, $C_{1-6}$ alkoxy, oxo, amino, N—($C_{1-6}$alkyl)amino, N,N-di($C_{1-6}$ alkyl)amino, N—($C_{1-6}$ acyl)amino, phenyl, or benzyl,
$C_{1-6}$ alkyl optionally substituted by $R^{21}$
or
$C_{1-6}$ alkoxy optionally substituted by $R^{21}$
wherein
$R^{21}$ represents cyano, mono-, di or tri-halogen, hydroxy, amino, N—($C_{1-6}$alkyl)amino, N,N-di($C_{1-6}$ alkyl)amino, N-(hydroxy$C_{1-6}$ alkyl) amino, N-(halophenyl$C_{1-6}$ alkyl) amino, amino $C_{2-6}$ alkylenyl, $C_{1-6}$ alkoxy, hydroxy$C_{1-6}$ alkoxy, —C(O)—$R^{201}$, —NHC(O)—$R^{201}$, $C_{3-8}$cycloalkyl, isoindolino, phthalimidyl, 2-oxo-1,3-oxazolidinyl, aryl or a 5 or 6 membered saturated or unsaturated heterocyclic ring having 1 to 4 heteroatoms selected from the group consisting O, S and N optionally substituted by hydroxy, $C_{1-6}$ alkyl, $C_{1-6}$ alkoxy, $C_{1-6}$ alkoxycarbonyl, hydroxy$C_{1-6}$ alkoxy, oxo, amino, amino$C_{1-6}$ alkyl, N—($C_{1-6}$alkyl)amino, N,N-di($C_{1-6}$ alkyl) amino, N—($C_{1-6}$ acyl)amino, or benzyl,
wherein
$R^{201}$ represents hydroxy, amino, N—($C_{1-6}$alkyl) amino, N,N-di($C_{1-6}$alkyl)amino, N-(halophenyl$C_{1-6}$ alkyl) amino, $C_{1-6}$alkyl, amino$C_{1-6}$ alkyl, amino$C_{2-6}$ alkylenyl, $C_{1-6}$ alkoxy, a 5 or 6 membered saturated or unsaturated heterocyclic ring having 1 to 4 heteroatoms selected from the group consisting O, S and N optionally substituted by hydroxy, $C_{1-6}$ alkyl, $C_{1-6}$ alkoxy, $C_{1-6}$ alkoxycarbonyl, hydroxy$C_{1-6}$ alkoxy, oxo, amino, N—($C_{1-6}$ alkyl)amino, N,N-di($C_{1-6}$alkyl)amino, N—($C_{1-6}$ acyl)amino or benzyl;
$R^3$ represents hydrogen, halogen, aminocarbonyl, or $C_{1-6}$ alkyl optionally substituted by aryl $C_{1-6}$ alkoxy or mono-, di- or tri-halogen;
$R^4$ represents hydrogen or $C_{1-6}$ alkyl;
$R^5$ represents hydrogen or $C_{1-6}$ alkyl; and
$R^6$ represents halogen, hydrogen or $C_{1-6}$ alkyl;
or a physiologically acceptable salt, solvate, hydrate or stereoisomer thereof; said compounds are published as compounds of general formulae I, I-a, and I-b in International patent application PCT/EP2003/010377, published as WO 04/029055 A1 on Apr. 8, 2004, which is incorporated herein by reference in its entirety. In WO 04/029055, said compounds of general formula I, I-a and I-b are described on pp. 6 et seq., they may be synthesized according to the methods given therein on pp. 26 et seq., and are exemplified as specific compound Examples 1-1 to 1-210 on pp. 47 to 106, specific compound Examples 2-1 to 2-368 on pp. 107 to 204, specific compound Examples 3-1 to 3-2 on pp. 205 to 207, and as specific compound Examples 4-1 to 4-2 on pp. 208 to 210, therein.

Said component A may be in the form of a pharmaceutical formulation which is ready for use to be administered simultaneously, concurrently, separately or sequentially. The components may be administered independently of one another by the oral, intravenous, topical, local installations, intraperitoneal or nasal route.

In accordance with another embodiment of the above-mentioned aspects of the present invention, said combinations are of:

component A: which is one or more 2,3-dihydroimidazo[1,2-c]quinazoline compounds of general formula (A1), supra, which is selected from the list consisting of specific compound Examples 1-1 to 1-210 on pp. 47 to 106, specific compound Examples 2-1 to 2-368 on pp. 107 to 204, specific compound Examples 3-1 to 3-2 on pp. 205 to 207, and specific compound Examples 4-1 to 4-2 on pp. 208 to 210, of in International patent application PCT/EP2003/010377, published as WO 04/029055 A1 on Apr. 8, 2004, which is incorporated herein by reference in its entirety, or a physiologically acceptable salt, solvate, hydrate or stereoisomer thereof.

Said component A may be in the form of a pharmaceutical formulation which is ready for use to be administered simultaneously, concurrently, separately or sequentially. The components may be administered independently of one another by the oral, intravenous, topical, local installations, intraperitoneal or nasal route.

As mentioned supra, said specific compound Examples may be synthesized according to the methods given in WO 04/029055 A1 on pp. 26 et seq.

In accordance with another embodiment of the above-mentioned aspects of the present invention, said combinations are of:

component A: which is one or more 2,3-dihydroimidazo[1,2-c]quinazoline compounds of general formula (A2):

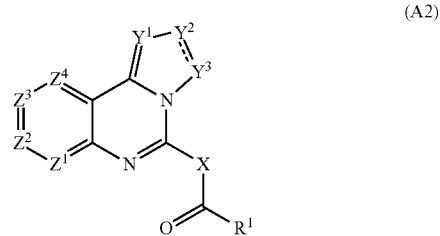

(A2)

in which:

X represents $CR^5R^6$ or NH;

$Y^1$ represents $CR^3$ or N;

the chemical bond between $Y^2 Y^2 = Y^3 Y^3$ represents a single bond or double bond, with the proviso that when the $Y^2 Y^2 = Y^3 Y^3$ represents a double bond, $Y^2$ and $Y^3$ independently represent $CR^4$ or N, and when $Y^2 = Y^3$ represents a single bond, $Y^2$ and $Y^3$ independently represent $CR^3R^4$ or $NR^4$;

$Z^1$, $Z^2$, $Z^3$ and $Z^4$ independently represent CH, $CR^2$ or N;

$R^1$ represents aryl optionally having 1 to 3 substituents selected from $R^{11}$, $C_{3-8}$ cycloalkyl optionally having 1 to 3 substituents selected from $R^{11}$, $C_{1-6}$ alkyl optionally substituted by aryl, heteroaryl, $C_{1-6}$ alkoxyaryl, aryloxy, heteroaryloxy or one or more halogen, $C_{1-6}$ alkoxy optionally substituted by carboxy, aryl, heteroaryl, $C_{1-6}$ alkoxyaryl, aryloxy, heteroaryloxy or one or more halogen, or a 3 to 15 membered mono- or bi-cyclic heterocyclic ring that is saturated or unsaturated, optionally having 1 to 3 substituents selected from $R^{11}$, and contains 1 to 3 heteroatoms selected from the group consisting of N, O and S, wherein $R^{11}$ represents halogen, nitro, hydroxy, cyano, carboxy, amino, N—($C_{1-6}$alkyl)amino, N-(hydroxy$C_{1-6}$alkyl) amino, N,N-di($C_{1-6}$alkyl)amino, N—($C_{1-6}$acyl) amino, N-(formyl)-N—($C_{1-6}$alkyl)amino, N—($C_{1-6}$ alkanesulfonyl) amino, N-(carboxy$C_{1-6}$alkyl)-N—($C_{1-6}$alkyl)amino, N—($C_{1-6}$alkoxycabonyl)amino, N—[N,N-di($C_{1-6}$alkyl)amino methylene]amino, N—[N,N-di($C_{1-6}$alkyl)amino ($C_{1-6}$alkyl)methylene] amino, N—[N,N-di($C_{1-6}$alkyl)amino $C_{2-6}$alkenyl] amino, aminocarbonyl, N—($C_{1-6}$alkyl)aminocarbonyl, N,N-di($C_{1-6}$alkyl)aminocarbonyl, $C_{3-8}$cycloalkyl, $C_{1-6}$ alkylthio, $C_{1-6}$alkanesulfonyl, sulfamoyl, $C_{1-6}$alkoxycarbonyl, N-arylamino wherein said aryl moiety is optionally having 1 to 3 substituents selected from $R^{101}$, N-(aryl $C_{1-6}$alkyl)amino wherein said aryl moiety is optionally having 1 to 3 substituents selected from $R^{101}$, aryl $C_{1-6}$alkoxycarbonyl wherein said aryl moiety is optionally having 1 to 3 substituents selected from $R^{101}$, $C_{1-6}$alkyl optionally substituted by mono-, di- or tri-halogen, amino, N—($C_{1-6}$alkyl)amino or N,N-di($C_{1-6}$ alkyl)amino, $C_{1-6}$alkoxy optionally substituted by mono-, di- or tri-halogen, N—($C_{1-6}$alkyl)sulfonamide, or N-(aryl) sulfonamide, or a 5 to 7 membered saturated or unsaturated ring having 1 to 3 heteroatoms selected from the group consisting of O, S and N, and optionally having 1 to 3 substituents selected from $R^{101}$ wherein $R^{101}$ represents halogen, carboxy, amino, N—($C_{1-6}$ alkyl)amino, N,N-di($C_{1-6}$alkyl)amino, aminocarbonyl, N—($C_{1-6}$alkyl)aminocarbonyl, N,N-di($C_{1-6}$ alkyl)aminocarbonyl, pyridyl, $C_{1-6}$ alkyl optionally substituted by cyano or mono- di- or tri-halogen, and $C_{1-6}$alkoxy optionally substituted by cyano, carboxy, amino, N—($C_{1-6}$alkyl)amino, N,N-di($C_{1-6}$alkyl) amino, aminocarbonyl, N—($C_{1-6}$alkyl)aminocarbonyl, N,N-di($C_{1-6}$alkyl)aminocarbonyl or mono-, di- or tri-halogen;

$R^2$ represents hydroxy, halogen, nitro, cyano, amino, N—($C_{1-6}$alkyl)amino, N,N-di($C_{1-6}$alkyl)amino, N-(hydroxy$C_{1-6}$alkyl)amino, N-(hydroxy$C_{1-6}$alkyl)-N—($C_{1-6}$ alkyl)amino, $C_{1-6}$ acyloxy, amino$C_{1-6}$acyloxy, $C_{2-6}$alkenyl, aryl, a 5-7 membered saturated or unsaturated heterocyclic ring having 1 to 3 heteroatoms selected from the group consisting O, S and N, and optionally substituted by hydroxy, $C_{1-6}$ alkyl, $C_{1-6}$ alkoxy, oxo, amino, amino $C_{1-6}$alkyl, N—($C_{1-6}$alkyl)amino, N,N-di($C_{1-6}$alkyl) amino, N—($C_{1-6}$ acyl)amino, N—($C_{1-6}$alkyl)carbonylamino, phenyl, phenyl $C_{1-6}$ alkyl, carboxy, $C_{1-6}$alkoxycarbonyl, aminocarbonyl, N—($C_{1-6}$alkyl) aminocarbonyl, or N,N-di($C_{1-6}$alkyl)amino, —C(O)—$R^{20}$ wherein $R^{20}$ represents $C_{1-6}$ alkyl, $C_{1-6}$ alkoxy, amino, N—($C_{1-6}$ alkyl)amino, N,N-di($C_{1-6}$alkyl)amino, N—($C_{1-6}$ acyl)amino, or a 5-7 membered saturated or unsaturated heterocyclic ring having 1 to 3 heteroatoms selected from the group consisting O, S and N, and optionally substituted by $C_{1-6}$ alkyl, $C_{1-6}$ alkoxy, oxo, amino, N—($C_{1-6}$alkyl)amino, N,N-di($C_{1-6}$ alkyl)amino, N—($C_{1-6}$ acyl)amino, phenyl, or benzyl, $C_{1-6}$ alkyl optionally substituted by $R^{21}$, or $C_{1-6}$ alkoxy optionally substituted by $R^{21}$, wherein $R^{21}$ represents cyano, mono-, di or tri-halogen, hydroxy, amino, N—($C_{1-6}$alkyl)amino, N,N-di ($C_{1-6}$alkyl)amino, N-(hydroxy$C_{1-6}$ alkyl) amino, N-(halophenyl$C_{1-6}$ alkyl) amino, amino $C_{2-6}$ alkylenyl, $C_{1-6}$ alkoxy, hydroxy$C_{1-6}$ alkoxy, —C(O)—$R^{201}$, —NHC(O)—$R^{201}$, $C_{3-8}$cycloalkyl, isoindolino, phthalimidyl, 2-oxo-1,3-oxazolidinyl, aryl or a 5 or 6 having 1 to 4 heteroatoms selected from the group consisting O, S and N, and optionally substituted by hydroxy, $C_{1-6}$ alkyl, $C_{1-6}$ alkoxy, $C_{1-6}$ alkoxycarbonyl, hydroxy$C_{1-6}$ alkoxy, oxo, amino, amino$C_{1-6}$alkyl, N—($C_{1-6}$alkyl)amino, N,N-di($C_{1-6}$alkyl)amino, N—($C_{1-6}$ acyl)amino, or benzyl, wherein $R^{201}$ represents hydroxy, amino, N—($C_{1-6}$alkyl) amino, N,N-di($C_{1-6}$alkyl)amino, N-(halophenyl$C_{1-6}$ alkyl) amino, $C_{1-6}$alkyl, amino$C_{1-6}$ alkyl, amino$C_{2-6}$ alkylenyl, $C_{1-6}$ alkoxy, a 5 or 6 membered saturated or unsaturated heterocyclic ring having 1 to 4 heteroatoms selected from the group consisting O, S and N, and optionally substituted by hydroxy, $C_{1-6}$ alkyl, $C_{1-6}$ alkoxy, $C_{1-6}$ alkoxycarbonyl, hydroxy$C_{1-6}$ alkoxy, oxo, amino, N—($C_{1-6}$alkyl)amino, N,N-di($C_{1-6}$ alkyl)amino, N—($C_{1-6}$ acyl)amino or benzyl;

$R^3$ represents hydrogen, halogen, aminocarbonyl, or $C_{1-6}$ alkyl optionally substituted by aryl $C_{1-6}$ alkoxy or mono-, di- or tri-halogen;

$R^4$ represents hydrogen or $C_{1-6}$ alkyl;

$R^5$ represents hydrogen or $C_{1-6}$ alkyl; and $R^6$ represents halogen, hydrogen or $C_{1-6}$ alkyl;

or a physiologically acceptable salt, solvate, hydrate or stereoisomer thereof; said compounds are published as compounds of general formulae I, Ia, Ib, Ic, Id and Ie in International patent application PCT/US2007/024985, published as WO 2008/070150 A1 on Jun. 12, 2008, which is incorporated herein by reference in its entirety. In WO 2008/070150, said compounds of general formula I, Ia, Ib, Ic, Id and Ie are described on pp. 9 et seq., they may be synthesized according to the methods given therein on pp. 42, et seq., and are exemplified as specific compound Examples 1 to 103 therein on pp. 65 to 101. Biological test data for certain of said compounds are given therein on pp. 101 to 107.

The definitions used in relation to the structure (A) in this text are as follows:

The term 'alkyl' refers to a straight or branched hydrocarbon chain radical consisting solely of carbon and hydrogen atoms, containing solely of carbon and hydrogen atoms, containing no unsaturation, having from one to eight carbon atoms, and which is attached to the rest of the molecule by a single bond, such as illustratively, methyl, ethyl, n-propyl 1-methylethyl (isopropyl), n-butyl, n-pentyl, and 1,1-dimethylethyl (t-butyl).

The term "alkenyl" refers to an aliphatic hydrocarbon group containing a carbon-carbon double bond and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, 2- and butenyl.

The term "alkynyl" refers to a straight or branched chain hydrocarbonyl radicals having at least one carbon-carbon triple bond, and having in the range of about 2 up to 12 carbon atoms (with radicals having in the range of about 2 up to 10 carbon atoms presently being preferred) e.g., ethynyl.

The term "alkoxy" denotes an alkyl group as defined herein attached via oxygen linkage to the rest of the molecule. Representative examples of those groups are methoxy and ethoxy.

The term "alkoxyakyl" denotes an alkoxy group as defined herein attached via oxygen linkage to an alkyl group which is then attached to the main structure at any carbon from alkyl group that results in the creation of a stable structure the rest of the molecule. Representative examples of those groups are $-CH_2OCH_3$, $-CH_2OC_2H_5$.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronapththyl, adamantyl and norbornyl groups bridged cyclic group or sprirobicyclic groups e.g spiro (4,4) non-2-yl.

The term "cycloalkylalkyl" refers to cyclic ring-containing radicals containing in the range of about about 3 up to 8 carbon atoms directly attached to alkyl group which is then also attached to the main structure at any carbon from the alkyl group that results in the creation of a stable structure such as cyclopropylmethyl, cyclobutylethyl, cyclopentylethyl.

The term "aryl" refers to aromatic radicals having in the range of 6 up to 14 carbon atoms such as phenyl, naphthyl, tetrahydronapthyl, indanyl, biphenyl.

The term "arylalkyl" refers to an aryl group as defined herein directly bonded to an alkyl group as defined herein which is then attached to the main structure at any carbon from alkyl group that results in the creation of a stable structure the rest of the molecule. e.g., $-CH_2C_6H_5$, $-C_2H_5C_6H_5$.

The term "heterocyclic ring" refers to a stable 3- to 15 membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl cinnolinyl dioxolanyl, indolizinyl, naphthyridinyl, perhydroazepinyl, phenazinyl, phenothiazinyl, phenoxazinyl, phthalazil, pyridyl, pteridinyl, purinyl, quinazolinyl, quinoxalinyl, quinolinyl, isoquinolinyl, tetrazoyl, imidazolyl tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl pyridazinyl, oxazolyl oxazolinyl oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl.

The term "heteroaryl" refers to heterocyclic ring radical as defined herein which are aromatic. The heteroaryl ring radical may be attached to the main structure at any heteroatom or carbon atom that results in the creation of a stable structure.

The heterocyclic ring radical may be attached to the main structure at any heteroatom or carbon atom that results in the creation of a stable structure.

The term "heteroarylalkyl" refers to heteroaryl ring radical as defined herein directly bonded to alkyl group. The heteroarylalkyl radical may be attached to the main structure at any carbon atom from alkyl group that results in the creation of a stable structure.

The term "heterocyclyl" refers to a heterocylic ring radical as defined herein. The heterocylyl ring radical may be attached to the main structure at any heteroatom or carbon atom that results in the creation of a stable structure.

The term "heterocyclylalkyl" refers to a heterocylic ring radical as defined herein directly bonded to alkyl group. The heterocyclylalkyl radical may be attached to the main structure at carbon atom in the alkyl group that results in the creation of a stable structure.

The term "carbonyl" refers to an oxygen atom bound to a carbon atom of the molecule by a double bond.

The term "halogen" refers to radicals of fluorine, chlorine, bromine and iodine.

Said component A may be in the form of a pharmaceutical formulation which is ready for use to be administered simultaneously, concurrently, separately or sequentially. The components may be administered independently of one another by the oral, intravenous, topical, local installations, intraperitoneal or nasal route.

In accordance with another embodiment of the abovementioned aspects of the present invention, said combinations are of:

component A: which is one or more 2,3-dihydroimidazo [1,2-c]quinazoline compounds of general formula (A2), supra, which is selected from the list consisting of:

Example 1: N-[7-methoxy-8-(3-morpholin-4-yl-propoxy)-2,3-dihydroimidazo[1,2-c]quinazolin-5-yl]pyrimidine-5-carboxamide Example 2: N-(8-{3-[(2R,6S)-2,6-dimethylmorpholin-4-yl]propoxy}-7-methoxy-2,3-dihydroimidazo[1,2-c]quinazolin-5-yl)nicotinamide Example 3: N-(8-{3-[(2R,6S)-2,6-dimethylmorpholin-4-yl]propoxy}-7-methoxy-2,3-dihydroimidazo[1,2-c]quinazolin-5-yl)-2,4-dimethyl-1,3-thiazole-5-carboxamide Example 4: 2-amino-N-[7-methoxy-8-(3-morpholin-4-ylpropoxy)-2,3-dihydroimidazo[1,2-c]quinazolin-5-yl]-1,3-thiazole-5-carboxamide Example 5: 2-amino-N-[7-methoxy-8-(3-morpholin-4-ylpropoxy)-2,3-dihydroimidazo[1,2-c]quinazolin-5-yl]isonicotinamide Example 6: 2-amino-N-[7-methoxy-8-(3-morpholin-4-ylpropoxy)-2,3-dihydroimidazo[1,2-c]quinazolin-5-yl]-4-methyl-1,3-thiazole-5-carboxamide Example 7: 2-amino-N-[7-methoxy-8-(3-morpholin-4-ylpropoxy)-2,3-dihydroimidazo[1,2-c]quinazolin-5-yl]-4-propylpyrimidine-5-carboxamide Example 8: N-{8-[2-(4-ethylmorpholin-2-yl)ethoxy]-7-methoxy-2,3-dihydroimidazo[1,2-c]quinazolin-5-yl}nicotinamide Example 9: N-{8-[2-(dimethylamino)ethoxy]-7-methoxy-2,3-dihydroimidazo[1,2-c]quinazolin-5-yl}pyrimidine-5-carboxamide Example 10: N-(8-{8-[2-(hydroxymethyl)morpholin-4-yl]propoxy}-7-methoxy-2,3-dihydroimidazo[1,2-c]quinazolin-5-yl)nicotinamide Example 11: N-(8-{3-[2-(hydroxymethyl)morpholin-4-yl]propoxy}-7-methoxy-2,3-dihydroimidazo[1,2-c]quinazolin-5-yl)nicotinamide Example 12: N-{8-[3-(dimethylamino)propoxy]-7-methoxy-2,3-dihydroimidazo[1,2-c]quinazolin-5-yl}nicotinamide 1-oxide Example 13: 2-amino-N-[7-methoxy-8-(3-morpholin-4-ylpropoxy)-2,3-dihydroimidazo[1,2-c]quinazolin-5-yl]pyrimidine-5-carboxamide Example 14: N-[7-methoxy-8-(3-morpholin-4-yl-propoxy)-2,3-dihydroimidazo[1,2-c]quinazolin-5-yl]-6-(2-pyrrolidin-1-ylethyl)nicotinamide Example 15: 6-(cyclopentylamino)-N-[7-methoxy-8-(3-morpholin-4-ylpropoxy)-2,3-dihydroimidazo[1,2-c]quinazolin-5-yl]nicotinamide

| Example | Structure |
|---|---|
| 16 | 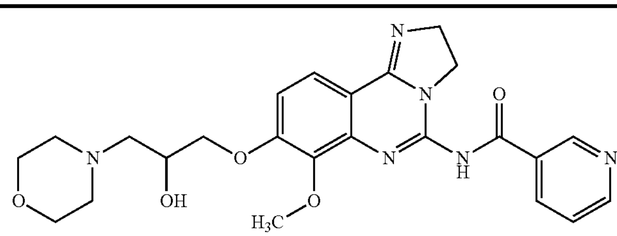 |
| 17 | 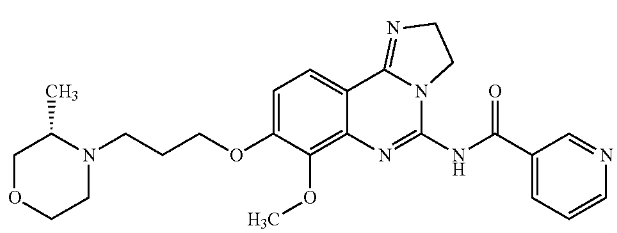 [SMILES: COc1c(OCCCN2CCOC[C@@H]2C)ccc2c1N=C(NC(=O)c1cccnc1)N1CCN=C21] |
| 18 | 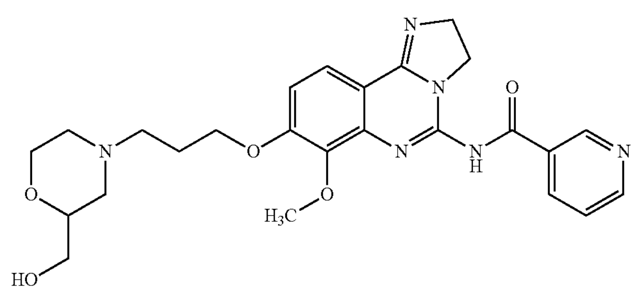 [SMILES: COc1c(OCCCN2CCOC(CO)C2)ccc2c1N=C(NC(=O)c1cccnc1)N1CCN=C21] |

US 10,406,162 B2
-continued
| Example | Structure |
|---|---|
| 19 | 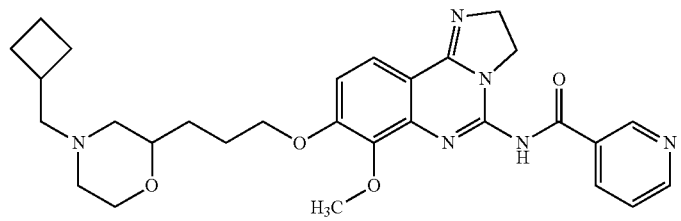 [SMILES: COc1c(OCCCC2CN(CC3CCC3)CCO2)ccc2c1N=C(NC(=O)c1cccnc1)N1CCN=C21] |
| 20 | 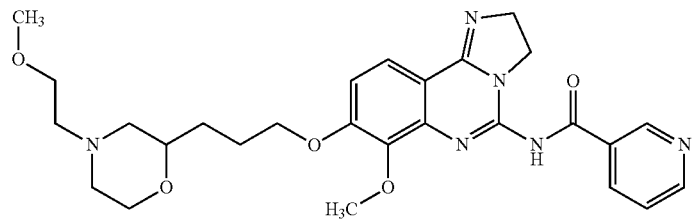 [SMILES: COCCN1CCOC(CCCOc2ccc3c(c2OC)N=C(NC(=O)c2cccnc2)N2CCN=C32)C1] |
| 21 | 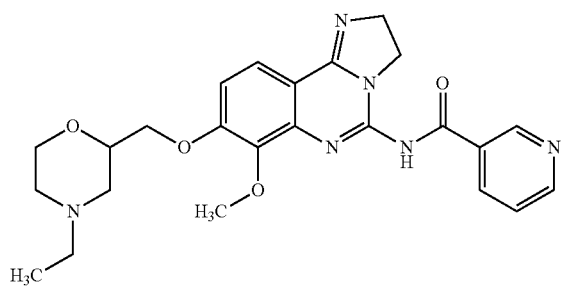 [SMILES: CCN1CCOC(COc2ccc3c(c2OC)N=C(NC(=O)c2cccnc2)N2CCN=C32)C1] |
| 22 | 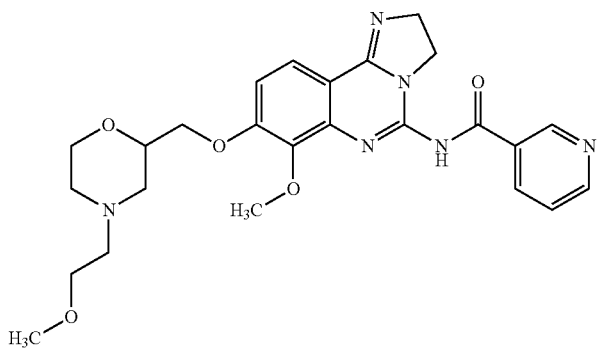 [SMILES: COCCN1CCOC(COc2ccc3c(c2OC)N=C(NC(=O)c2cccnc2)N2CCN=C32)C1] |
| 23 | 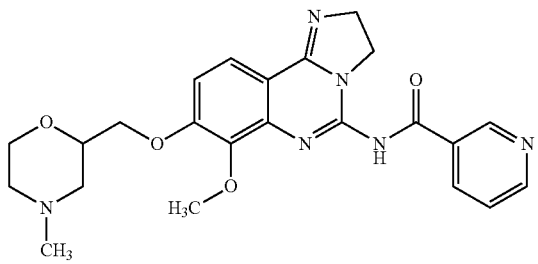 [SMILES: COc1c(OCC2CN(C)CCO2)ccc2c1N=C(NC(=O)c1cccnc1)N1CCN=C21] |
| 24 | 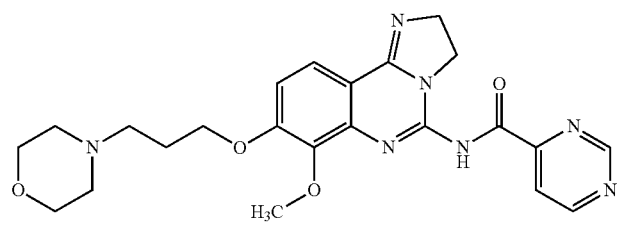 [SMILES: COc1c(OCCCN2CCOCC2)ccc2c1N=C(NC(=O)c1ccncn1)N1CCN=C21] |

-continued
| Example | Structure |
|---------|-----------|
| 25 | 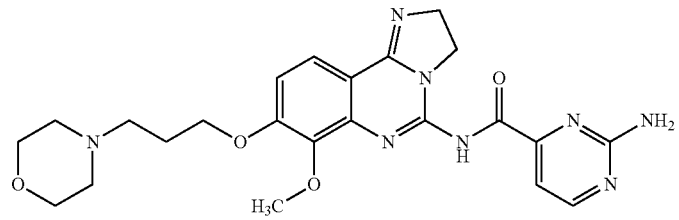 [SMILES: COc1c(OCCCN2CCOCC2)ccc2c1N=C(NC(=O)c1ccnc(N)n1)N1CCN=C21] |
| 26 | 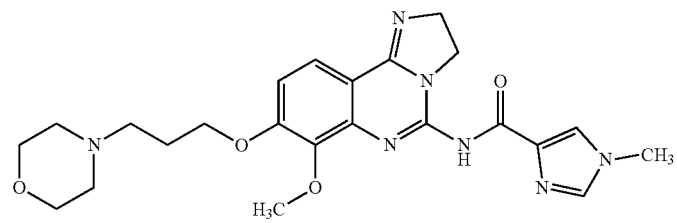 [SMILES: COc1c(OCCCN2CCOCC2)ccc2c1N=C(NC(=O)c1cn(C)cn1)N1CCN=C21] |
| 27 | 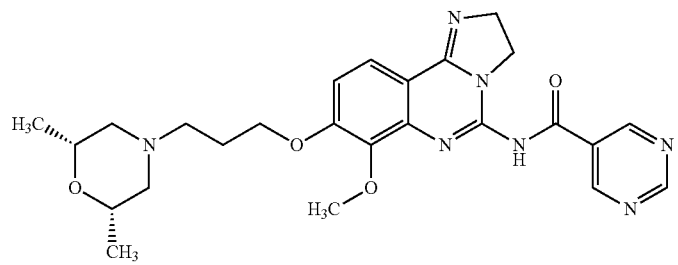 [SMILES: COc1c(OCCCN2C[C@@H](C)O[C@@H](C)C2)ccc2c1N=C(NC(=O)c1cncnc1)N1CCN=C21] |
| 28 | 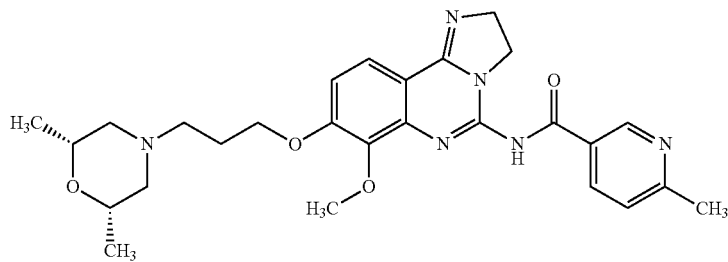 |
| 29 | 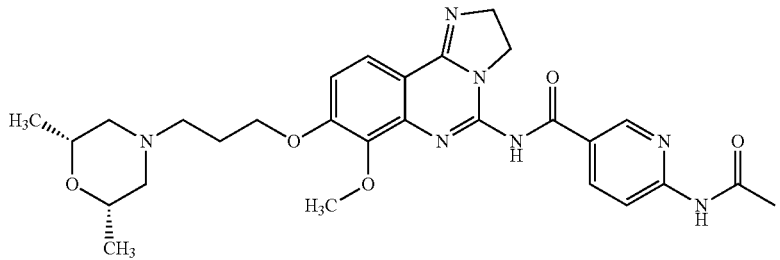 [SMILES: COc1c(OCCCN2C[C@@H](C)O[C@@H](C)C2)ccc2c1N=C(NC(=O)c1ccc(NC(C)=O)nc1)N1CCN=C21] |
| 30 | 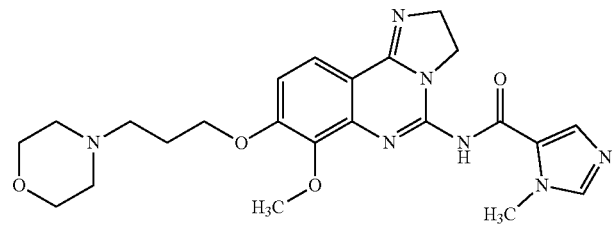 [SMILES: COc1c(OCCCN2CCOCC2)ccc2c1N=C(NC(=O)c1cncn1C)N1CCN=C21] |

-continued
| Example | Structure |
|---|---|
| 31 | 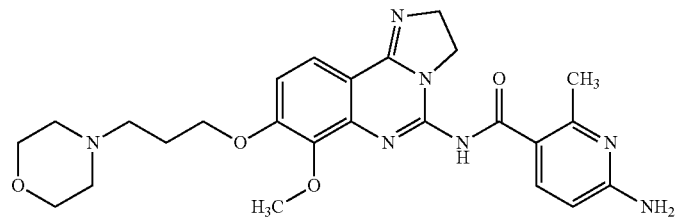 [SMILES: COc1c(OCCCN2CCOCC2)ccc2c1N=C(NC(=O)c1ccc(N)nc1C)N1CCN=C21] |
| 32 | 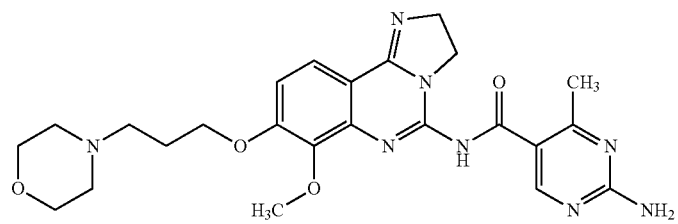 [SMILES: COc1c(OCCCN2CCOCC2)ccc2c1N=C(NC(=O)c1cnc(N)nc1C)N1CCN=C21] |
| 33 | 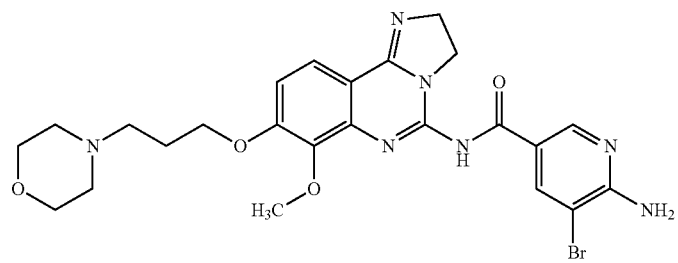 [SMILES: COc1c(OCCCN2CCOCC2)ccc2c1N=C(NC(=O)c1cnc(N)c(Br)c1)N1CCN=C21] |
| 34 | 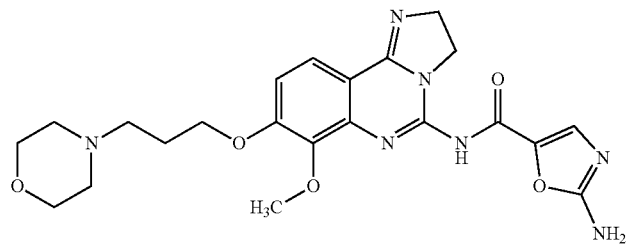 [SMILES: COc1c(OCCCN2CCOCC2)ccc2c1N=C(NC(=O)c1cnc(N)o1)N1CCN=C21] |
| 35 | 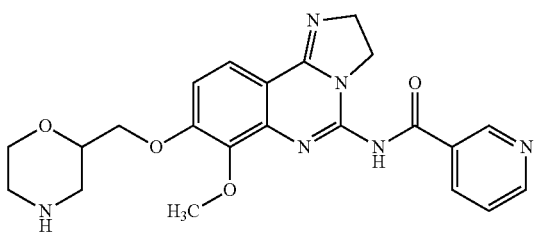 [SMILES: COc1c(OCC2CNCCO2)ccc2c1N=C(NC(=O)c1cccnc1)N1CCN=C21] |
| 36 | 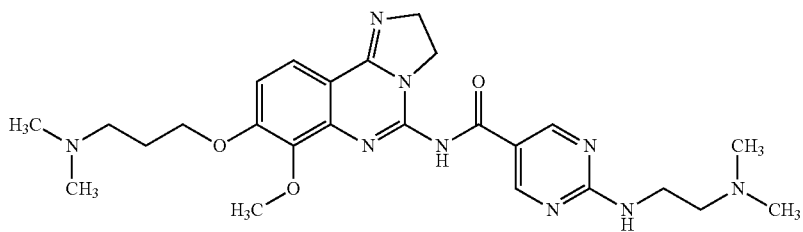 |

| Example | Structure |
|---|---|
| 37 | 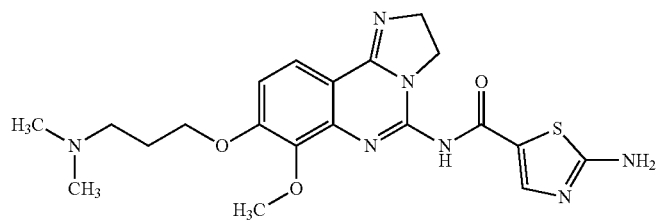 [SMILES: COc1c(OCCCN(C)C)ccc2c1N=C(NC(=O)c1cnc(N)s1)N1CCN=C21] |
| 38 | 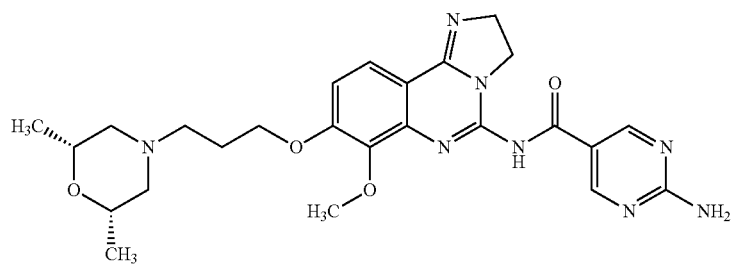 |
| 39 | 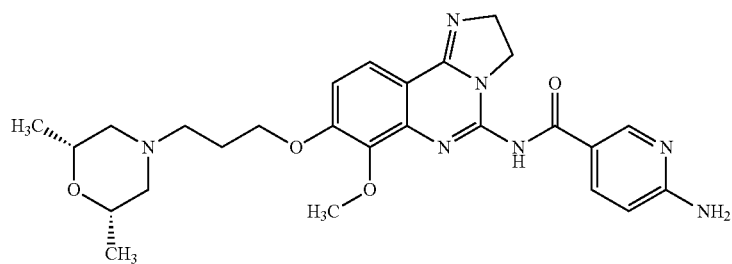 [SMILES: COc1c(OCCCN2C[C@@H](C)O[C@@H](C)C2)ccc2c1N=C(NC(=O)c1ccc(N)nc1)N1CCN=C21] |
| 40 | 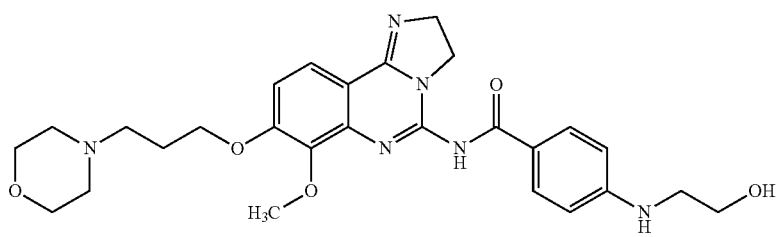 [SMILES: COc1c(OCCCN2CCOCC2)ccc2c1N=C(NC(=O)c1ccc(NCCO)cc1)N1CCN=C21] |
| 41 | 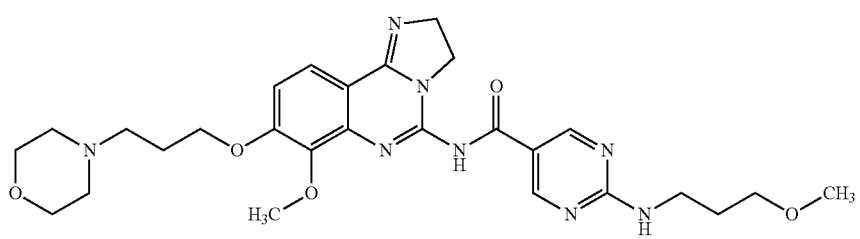 [SMILES: COCCCNc1ncc(C(=O)NC2=Nc3c(ccc(OCCCN4CCOCC4)c3OC)C3=NCCN23)cn1] |
| 42 | 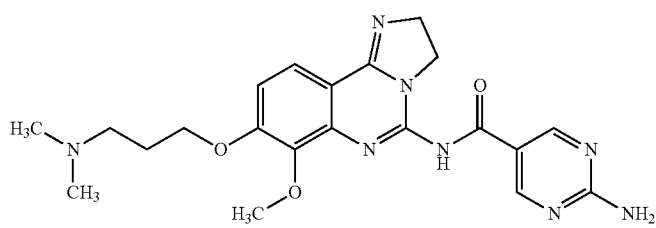 [SMILES: COc1c(OCCCN(C)C)ccc2c1N=C(NC(=O)c1cnc(N)nc1)N1CCN=C21] |

-continued
| Example | Structure |
|---|---|
| 43 | 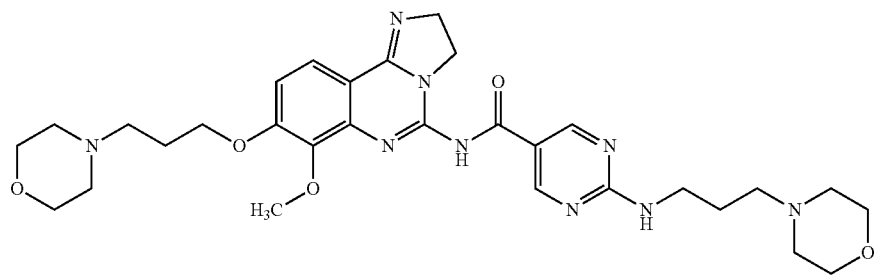 [SMILES: COc1c(OCCCN2CCOCC2)ccc2c1N=C(NC(=O)c1cnc(NCCCN3CCOCC3)nc1)N1CCN=C21] |
| 44 | 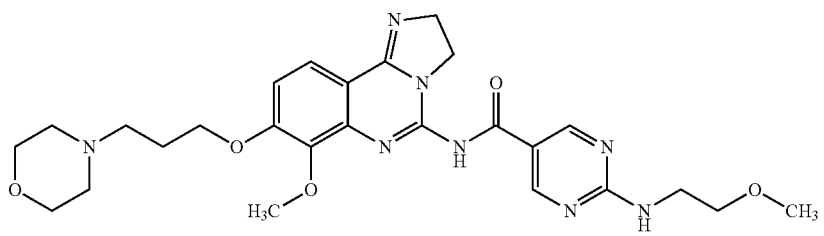 [SMILES: COCCNc1ncc(C(=O)NC2=Nc3c(ccc(OCCCN4CCOCC4)c3OC)C3=NCCN23)cn1] |
| 45 | 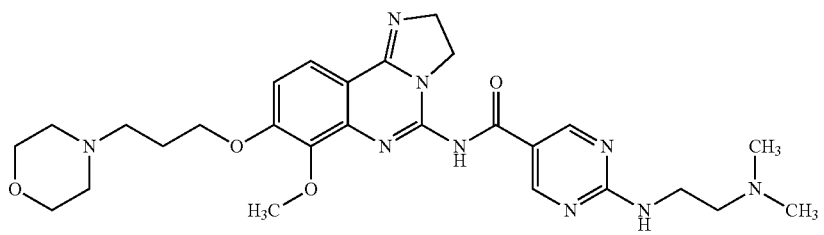 [SMILES: COc1c(OCCCN2CCOCC2)ccc2c1N=C(NC(=O)c1cnc(NCCN(C)C)nc1)N1CCN=C21] |
| 46 | 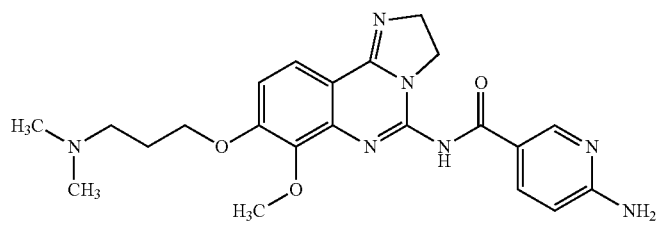 [SMILES: COc1c(OCCCN(C)C)ccc2c1N=C(NC(=O)c1ccc(N)nc1)N1CCN=C21] |
| 47 | 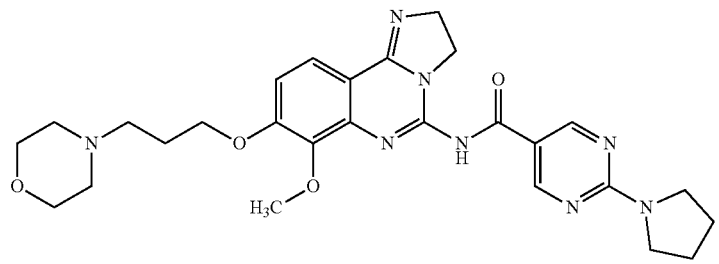 [SMILES: COc1c(OCCCN2CCOCC2)ccc2c1N=C(NC(=O)c1cnc(N3CCCC3)nc1)N1CCN=C21] |
| 48 | 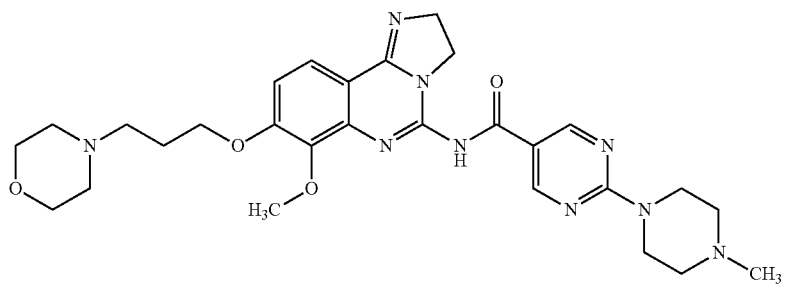 [SMILES: COc1c(OCCCN2CCOCC2)ccc2c1N=C(NC(=O)c1cnc(N3CCN(C)CC3)nc1)N1CCN=C21] |

-continued
| Example | Structure |
|---|---|
| 49 | 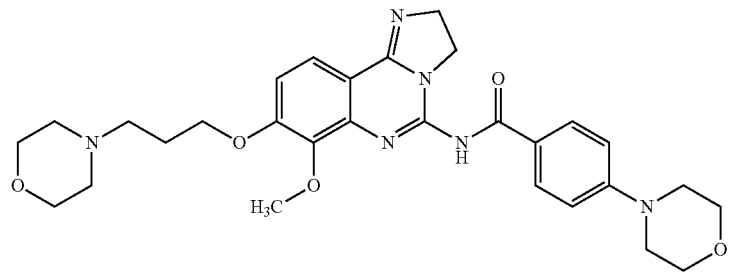 [SMILES: COc1c(OCCCN2CCOCC2)ccc2c1N=C(NC(=O)c1ccc(N3CCOCC3)cc1)N1CCN=C21] |
| 50 | 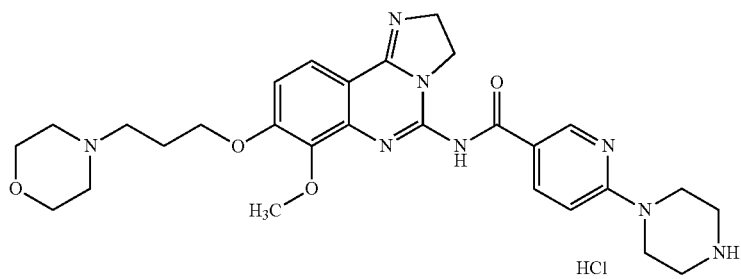 [SMILES: COc1c(OCCCN2CCOCC2)ccc2c1N=C(NC(=O)c1ccc(N3CCNCC3)nc1)N1CCN=C21 ; Cl] |
| 51 | 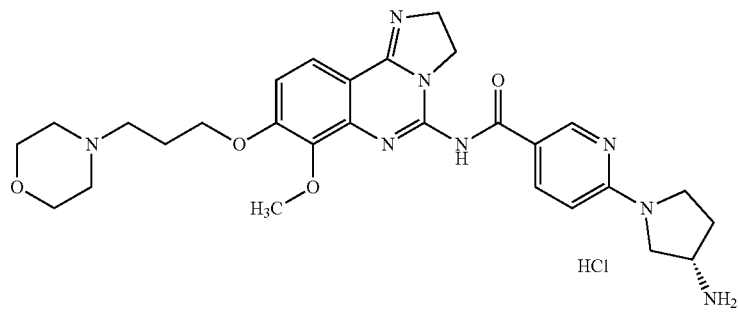 [SMILES: COc1c(OCCCN2CCOCC2)ccc2c1N=C(NC(=O)c1ccc(N3CC[C@H](N)C3)nc1)N1CCN=C21 ; Cl] |
| 52 | 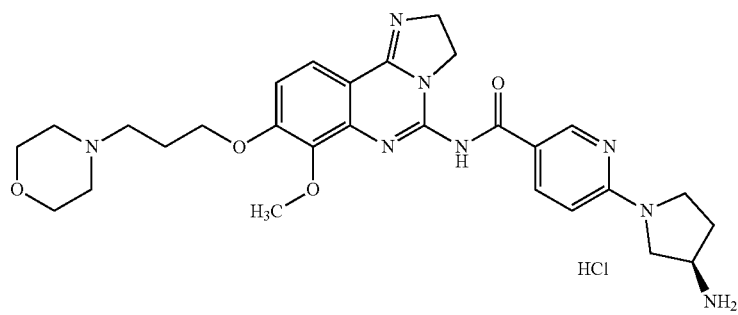 [SMILES: COc1c(OCCCN2CCOCC2)ccc2c1N=C(NC(=O)c1ccc(N3CC[C@@H](N)C3)nc1)N1CCN=C21 ; Cl] |
| 53 | 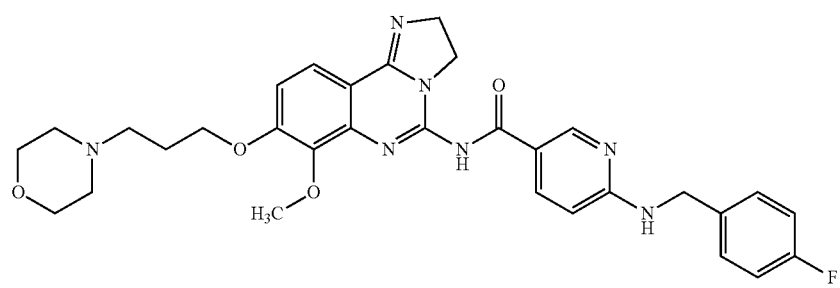 [SMILES: COc1c(OCCCN2CCOCC2)ccc2c1N=C(NC(=O)c1ccc(NCc3ccc(F)cc3)nc1)N1CCN=C21] |

-continued
| Example | Structure |
|---|---|
| 54 | 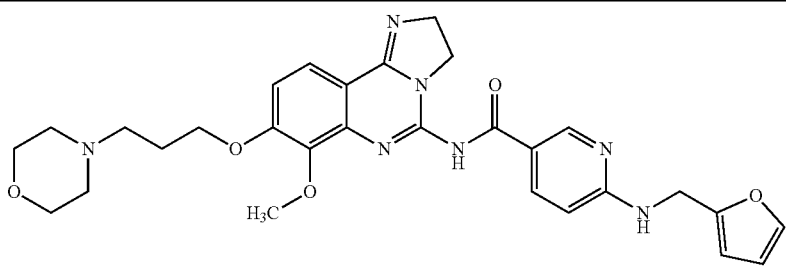 |
| 55 | 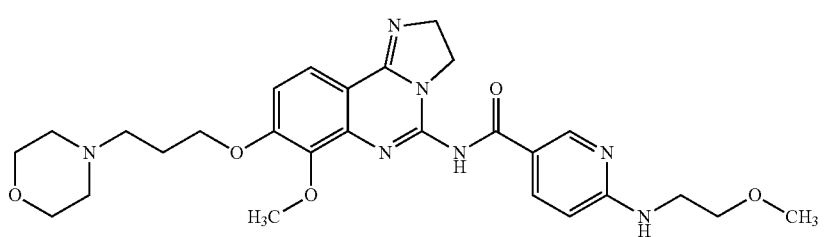 [SMILES: COCCNc1ccc(C(=O)NC2=Nc3c(ccc(OCCCN4CCOCC4)c3OC)C3=NCCN23)cn1] |
| 56 | 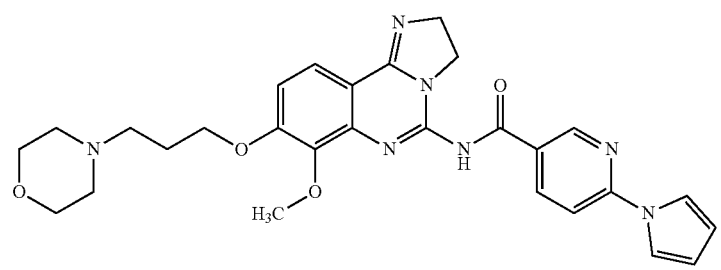 [SMILES: COc1c(OCCCN2CCOCC2)ccc2c1N=C(NC(=O)c1ccc(-n3cccc3)nc1)N1CCN=C21] |
| 57 | 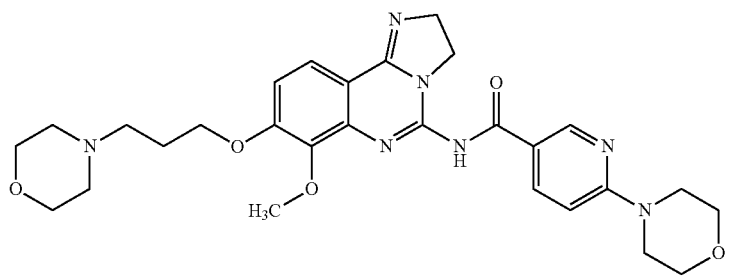 [SMILES: COc1c(OCCCN2CCOCC2)ccc2c1N=C(NC(=O)c1ccc(N3CCOCC3)nc1)N1CCN=C21] |
| 58 | 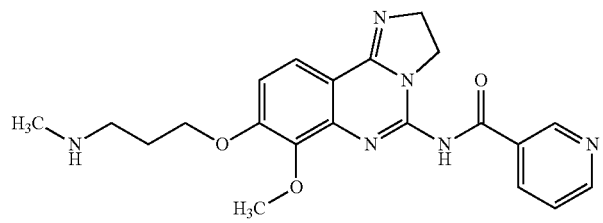 [SMILES: CNCCCOc1ccc2c(c1OC)N=C(NC(=O)c1cccnc1)N1CCN=C21] |
| 59 | 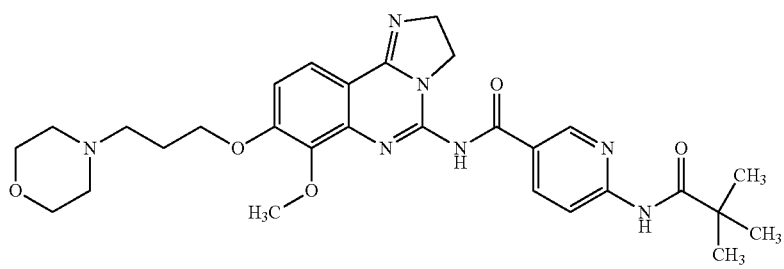 [SMILES: COc1c(OCCCN2CCOCC2)ccc2c1N=C(NC(=O)c1ccc(NC(=O)C(C)(C)C)nc1)N1CCN=C21] |

| Example | Structure |
|---|---|
| 60 | 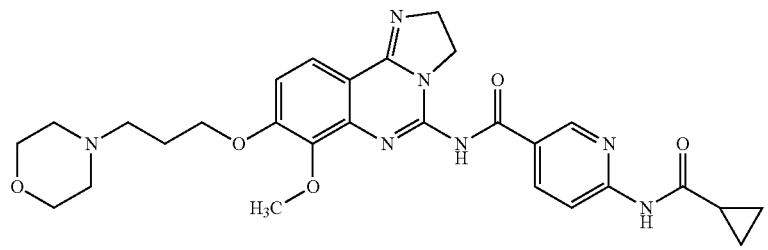 [SMILES: COc1c(OCCCN2CCOCC2)ccc2c1N=C(NC(=O)c1ccc(NC(=O)C3CC3)nc1)N1CCN=C21] |
| 61 | 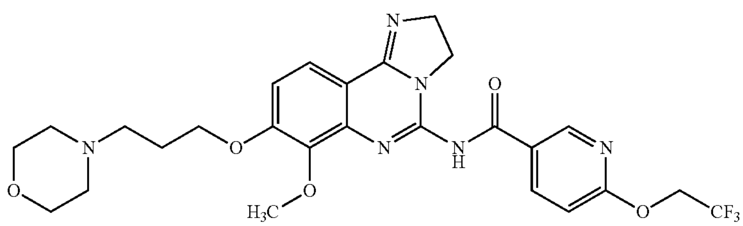 [SMILES: COc1c(OCCCN2CCOCC2)ccc2c1N=C(NC(=O)c1ccc(OCC(F)(F)F)nc1)N1CCN=C21] |
| 62 | 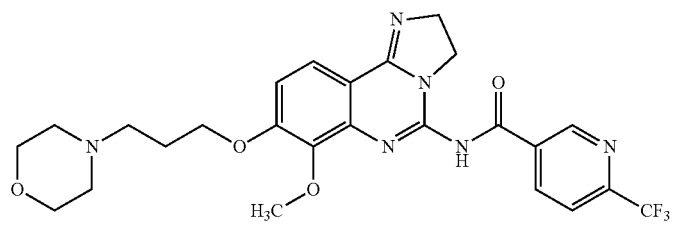 [SMILES: COc1c(OCCCN2CCOCC2)ccc2c1N=C(NC(=O)c1ccc(C(F)(F)F)nc1)N1CCN=C21] |
| 63 | 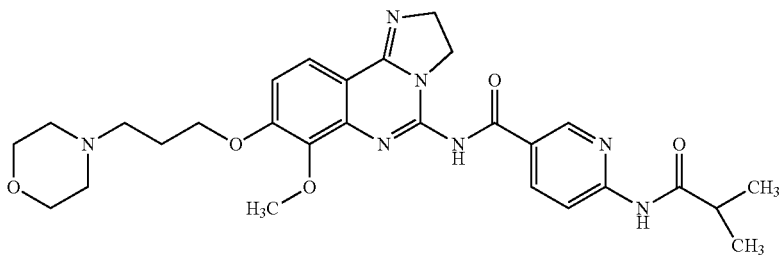 [SMILES: COc1c(OCCCN2CCOCC2)ccc2c1N=C(NC(=O)c1ccc(NC(=O)C(C)C)nc1)N1CCN=C21] |
| 64 | 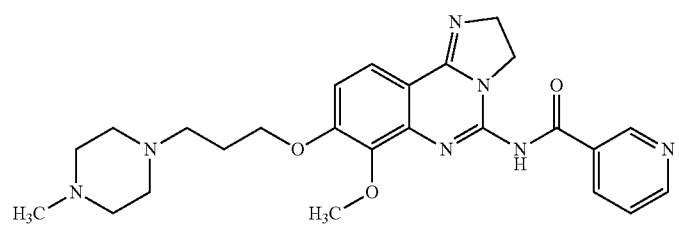 [SMILES: COc1c(OCCCN2CCN(C)CC2)ccc2c1N=C(NC(=O)c1cccnc1)N1CCN=C21] |
| 65 | 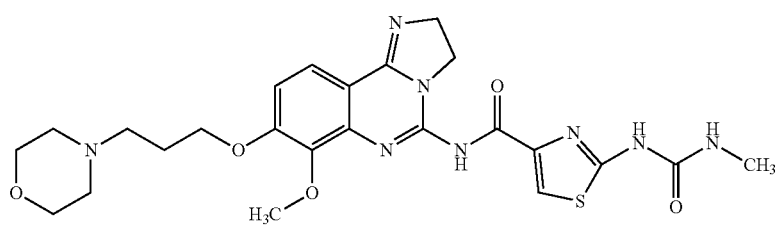 [SMILES: CNC(=O)Nc1nc(C(=O)NC2=Nc3c(ccc(OCCCN4CCOCC4)c3OC)C3=NCCN23)cs1] |

| Example | Structure |
|---|---|
| 66 | 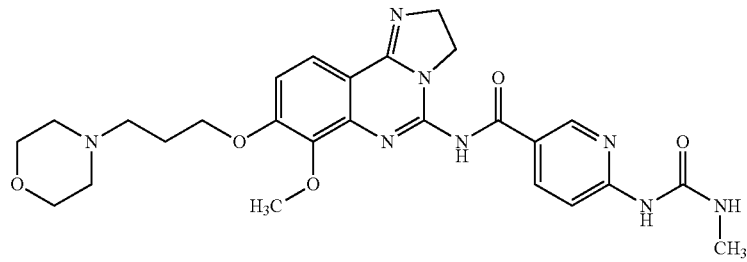 [SMILES: CNC(=O)Nc1ccc(C(=O)NC2=Nc3c(ccc(OCCCN4CCOCC4)c3OC)C3=NCCN23)cn1] |
| 67 | 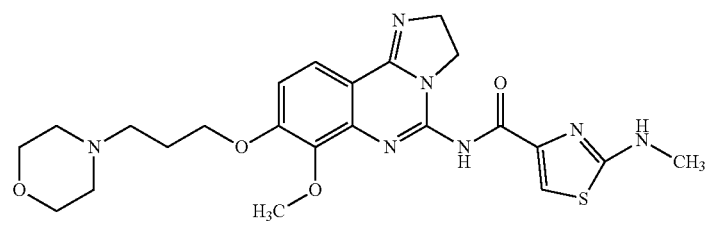 [SMILES: CNc1nc(C(=O)NC2=Nc3c(ccc(OCCCN4CCOCC4)c3OC)C3=NCCN23)cs1] |
| 68 | 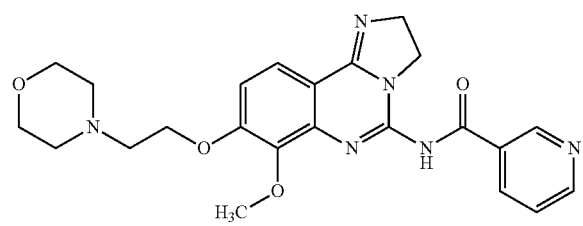 [SMILES: COc1c(OCCN2CCOCC2)ccc2c1N=C(NC(=O)c1cccnc1)N1CCN=C21] |
| 69 | 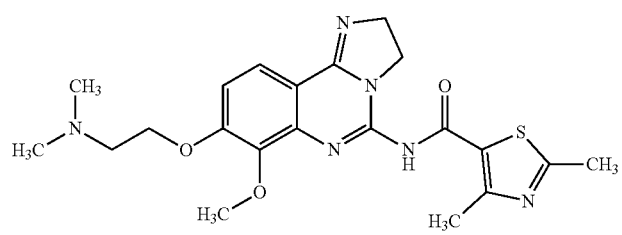 |
| 70 | 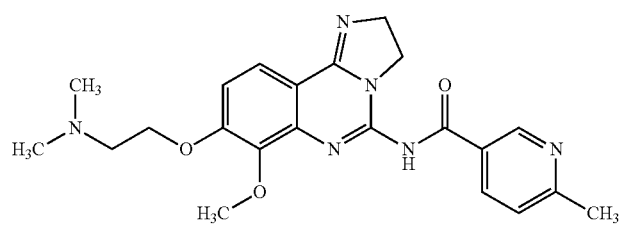 |
| 71 | 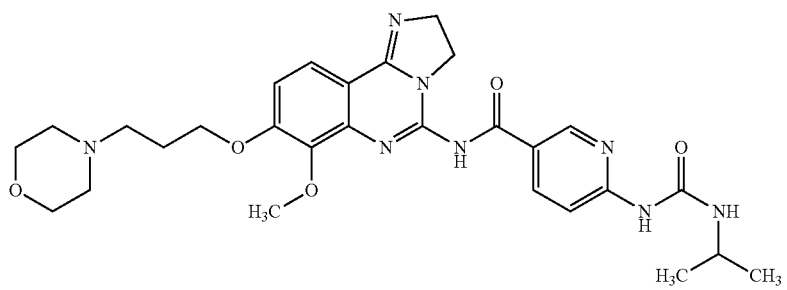 [SMILES: COc1c(OCCCN2CCOCC2)ccc2c1N=C(NC(=O)c1ccc(NC(=O)NC(C)C)nc1)N1CCN=C21] |

| Example | Structure |
|---|---|
| 72 | 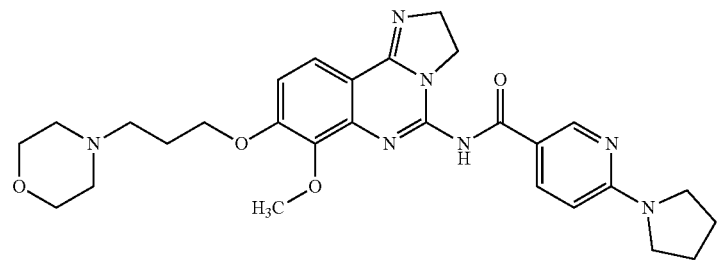 [SMILES: COc1c(OCCCN2CCOCC2)ccc2c1N=C(NC(=O)c1ccc(N3CCCC3)nc1)N1CCN=C21] |
| 73 | 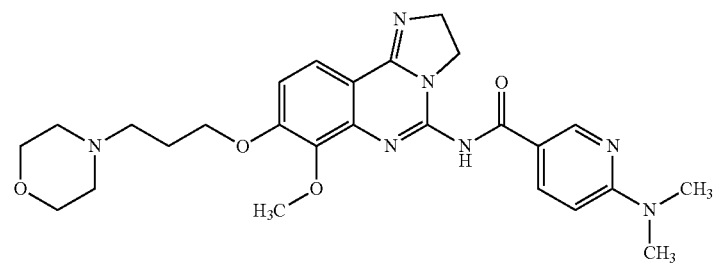 [SMILES: COc1c(OCCCN2CCOCC2)ccc2c1N=C(NC(=O)c1ccc(N(C)C)nc1)N1CCN=C21] |
| 74 | 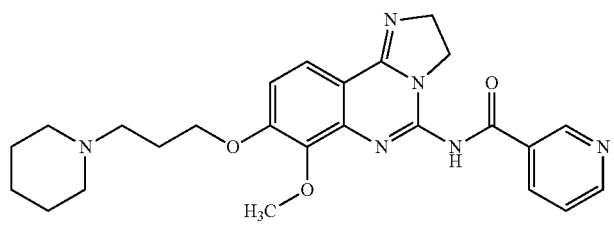 [SMILES: COc1c(OCCCN2CCCCC2)ccc2c1N=C(NC(=O)c1cccnc1)N1CCN=C21] |
| 75 | 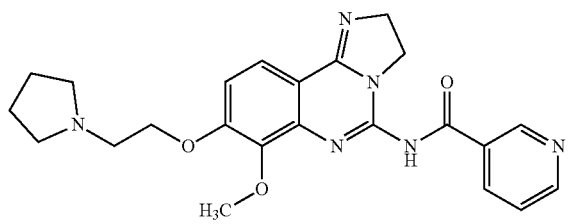 [SMILES: COc1c(OCCN2CCCC2)ccc2c1N=C(NC(=O)c1cccnc1)N1CCN=C21] |
| 76 | 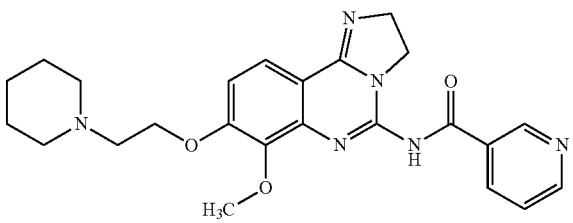 [SMILES: COc1c(OCCN2CCCCC2)ccc2c1N=C(NC(=O)c1cccnc1)N1CCN=C21] |
| 77 | 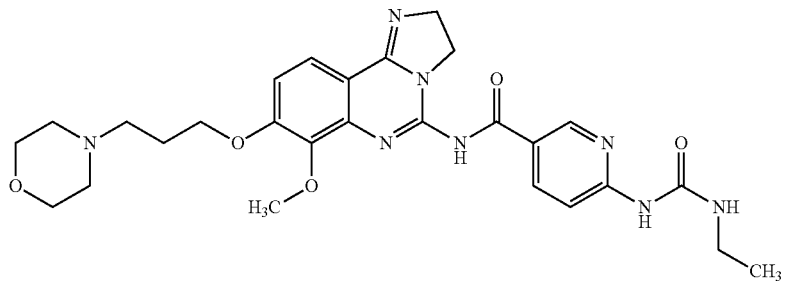 [SMILES: CCNC(=O)Nc1ccc(C(=O)NC2=Nc3c(ccc(OCCCN4CCOCC4)c3OC)C3=NCCN23)cn1] |

-continued
| Example | Structure |
|---|---|
| 78 | 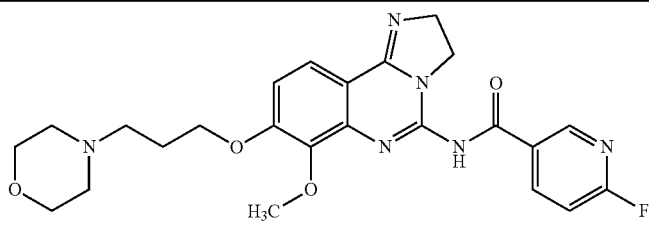 |
| 79 | 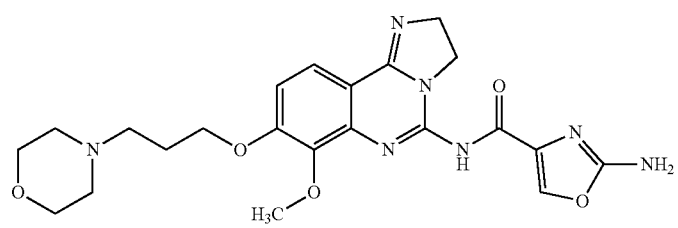 [SMILES: COc1c(OCCCN2CCOCC2)ccc2c1N=C(NC(=O)c1coc(N)n1)N1CCN=C21] |
| 80 | 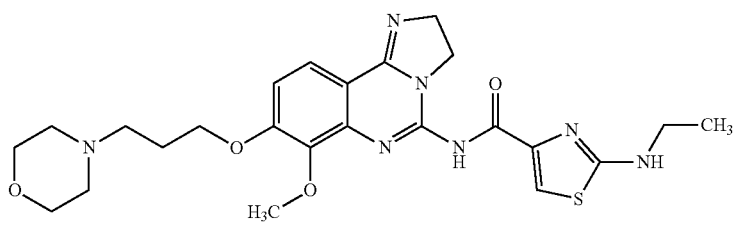 [SMILES: CCNc1nc(C(=O)NC2=Nc3c(ccc(OCCCN4CCOCC4)c3OC)C3=NCCN23)cs1] |
| 81 | 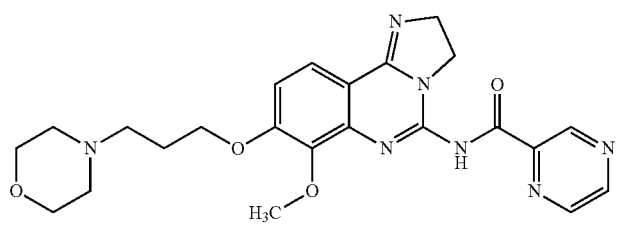 [SMILES: COc1c(OCCCN2CCOCC2)ccc2c1N=C(NC(=O)c1cnccn1)N1CCN=C21] |
| 82 | 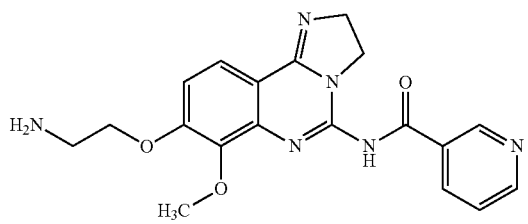 [SMILES: COc1c(OCCN)ccc2c1N=C(NC(=O)c1cccnc1)N1CCN=C21] |
| 83 | 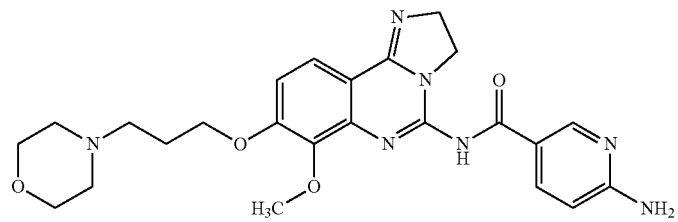 [SMILES: COc1c(OCCCN2CCOCC2)ccc2c1N=C(NC(=O)c1ccc(N)nc1)N1CCN=C21] |
| 84 | 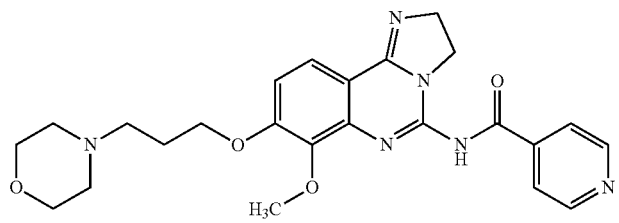 [SMILES: COc1c(OCCCN2CCOCC2)ccc2c1N=C(NC(=O)c1ccncc1)N1CCN=C21] |

| Example | Structure |
|---|---|
| 85 | 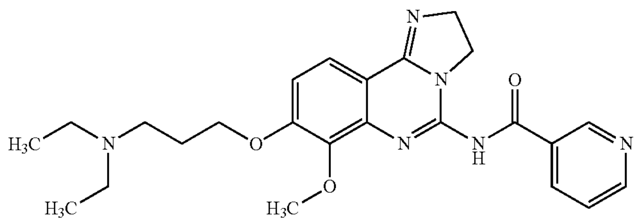 [SMILES: CCN(CC)CCCOc1ccc2c(c1OC)N=C(NC(=O)c1cccnc1)N1CCN=C21] |
| 86 | 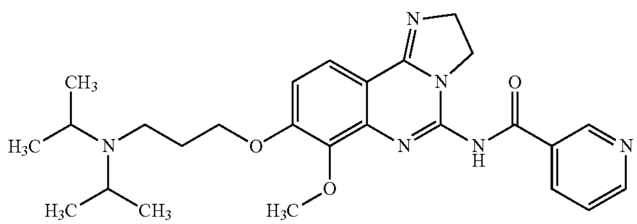 [SMILES: COc1c(OCCCN(C(C)C)C(C)C)ccc2c1N=C(NC(=O)c1cccnc1)N1CCN=C21] |
| 87 | 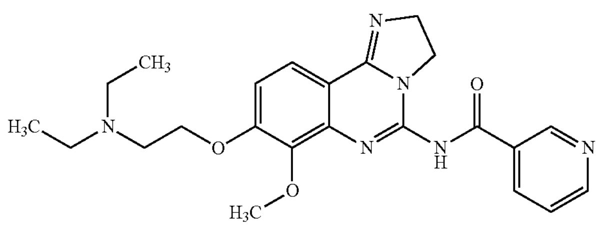 [SMILES: CCN(CC)CCOc1ccc2c(c1OC)N=C(NC(=O)c1cccnc1)N1CCN=C21] |
| 88 | 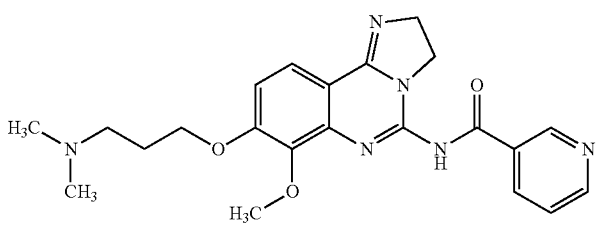 [SMILES: COc1c(OCCCN(C)C)ccc2c1N=C(NC(=O)c1cccnc1)N1CCN=C21] |
| 89 | 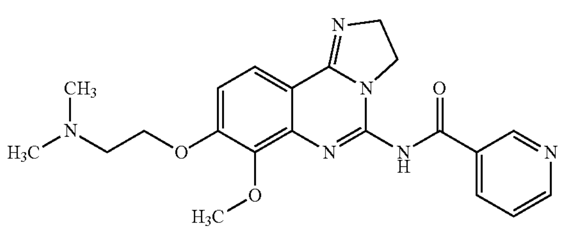 [SMILES: COc1c(OCCN(C)C)ccc2c1N=C(NC(=O)c1cccnc1)N1CCN=C21] |
| 90 | 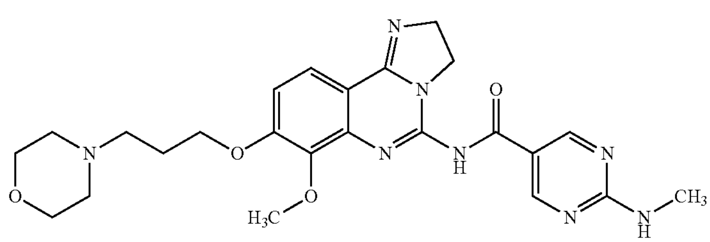 [SMILES: CNc1ncc(C(=O)NC2=Nc3c(ccc(OCCCN4CCOCC4)c3OC)C3=NCCN23)cn1] |
| 91 | 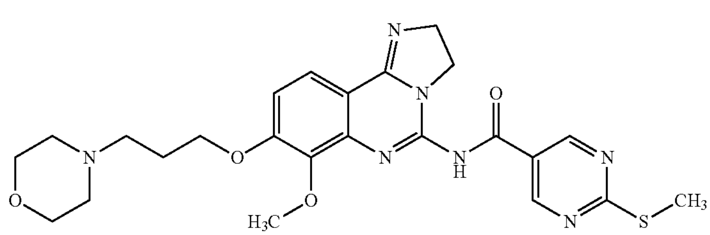 [SMILES: COc1c(OCCCN2CCOCC2)ccc2c1N=C(NC(=O)c1cnc(SC)nc1)N1CCN=C21] |

| Example | Structure |
|---|---|
| 92 | 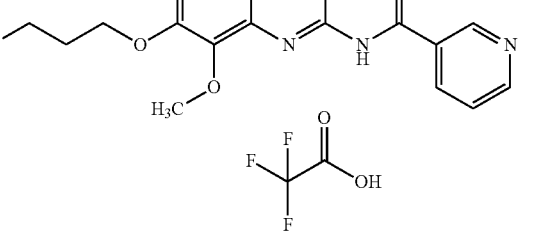 |
| 93 | 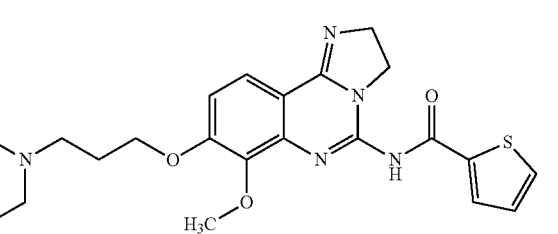 |
| 94 | 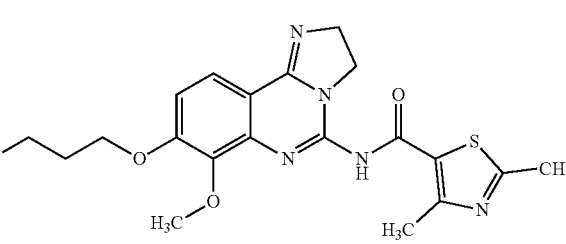 |
| 95 | 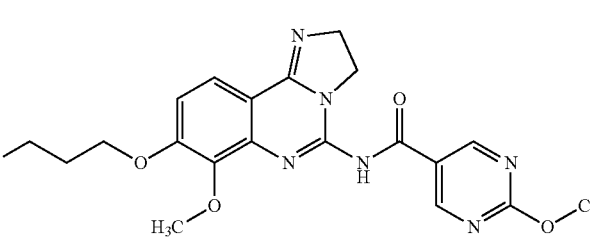 |
| 96 | 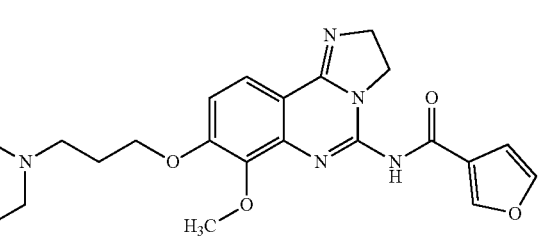 |
| 97 | 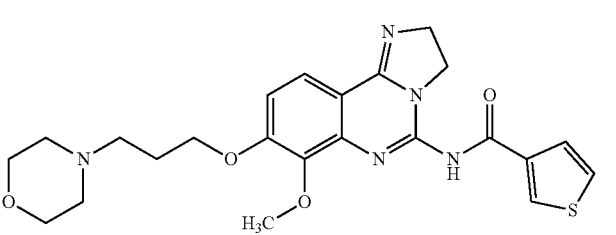 [SMILES: COc1c(OCCCN2CCOCC2)ccc2c1N=C(NC(=O)c1ccsc1)N1CCN=C21] |

| Example | Structure |
|---|---|
| 98 | 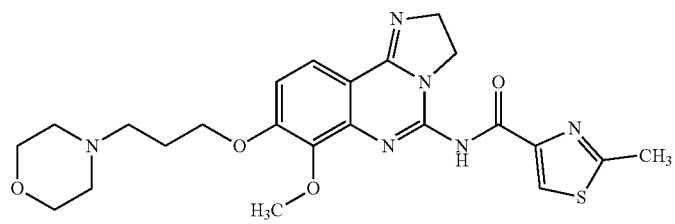 [SMILES: COc1c(OCCCN2CCOCC2)ccc2c1N=C(NC(=O)c1csc(C)n1)N1CCN=C21] |
| 99 | 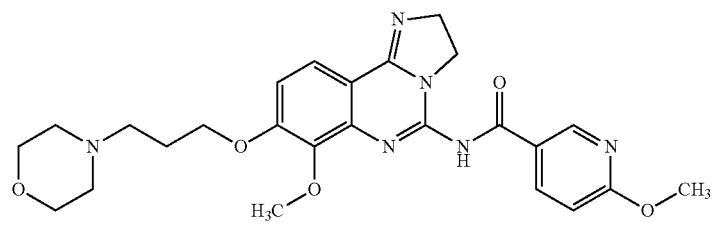 [SMILES: COc1ccc(C(=O)NC2=Nc3c(ccc(OCCCN4CCOCC4)c3OC)C3=NCCN23)cn1] |
| 100 | 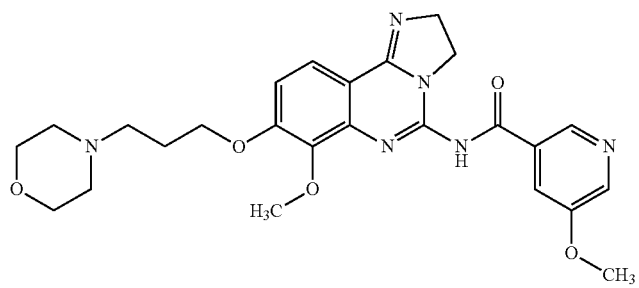 [SMILES: COc1cncc(C(=O)NC2=Nc3c(ccc(OCCCN4CCOCC4)c3OC)C3=NCCN23)c1] |
| 101 | 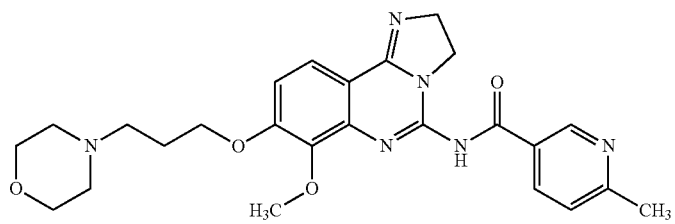 [SMILES: COc1c(OCCCN2CCOCC2)ccc2c1N=C(NC(=O)c1ccc(C)nc1)N1CCN=C21] |
| 102 | 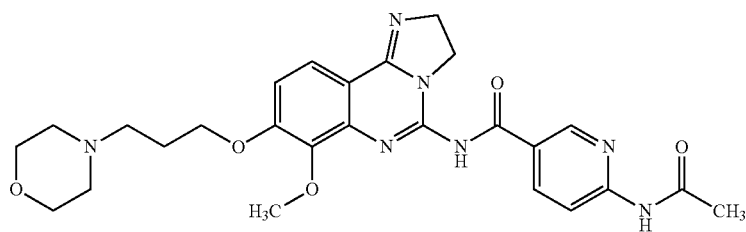 [SMILES: COc1c(OCCCN2CCOCC2)ccc2c1N=C(NC(=O)c1ccc(NC(C)=O)nc1)N1CCN=C21] |
| 103 | 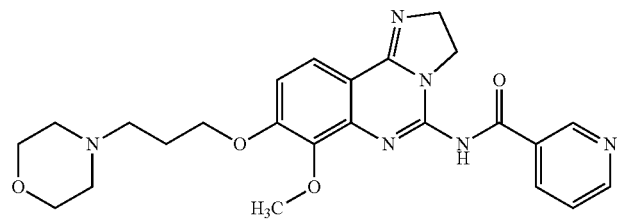 [SMILES: COc1c(OCCCN2CCOCC2)ccc2c1N=C(NC(=O)c1cccnc1)N1CCN=C21] | or a physiologically acceptable salt, solvate, hydrate or stereoisomer thereof, said compounds are published as specific compound Examples 1 to 103 in International patent application PCT/US2007/024985, published as WO 2008/070150 A1 on Jun. 12, 2008, which is incorporated herein by reference in its entirety. In WO 2008/070150, said specific compound Examples may be synthesized according to the Examples. Biological test data for certain of said compounds are given therein on pp. 101 to 107.

Said component A may be in the form of a pharmaceutical formulation which is ready for use to be administered simultaneously, concurrently, separately or sequentially. The components may be administered independently of one another by the oral, intravenous, topical, local installations, intraperitoneal or nasal route.

In accordance with an embodiment of the above-mentioned aspects of the present invention, said combinations are of:

component B: which is one or more substituted 5-(1-benzothiophen-2-yl)pyrrolo[2,1-f][1,2,4]-triazin-4-amine compounds of general formula (B):

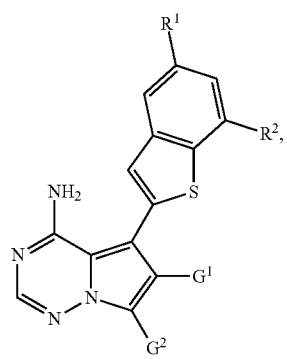

(B)

wherein
$R^1$ is hydrogen, chloro, methyl or methoxy,
$R^2$ is hydrogen or methoxy, with the proviso that at least one of $R^1$ and $R^2$ is other than hydrogen,
$G^1$ represents chloro, $(C_1-C_4)$-alkyl, $(C_1-C_4)$-alkoxycarbonyl, 5-membered aza-heteroaryl, or the group —$CH_2$—$OR^3$, —$CH_2$—$NR^4R^5$ or —C(=O)—$NR^4R^6$, wherein
  $R^3$ is hydrogen, $(C_1-C_4)$-alkyl, $(C_3-C_6)$-cycloalkyl or phenyl,
    (i) said $(C_1-C_4)$-alkyl is optionally substituted with hydroxy, $(C_1-C_4)$-alkoxy, hydroxycarbonyl, $(C_1-C_4)$-alkoxycarbonyl, amino, aminocarbonyl, mono-$(C_1-C_4)$-alkylaminocarbonyl, di-$(C_1-C_4)$-alkylaminocarbonyl, $(C_3-C_6)$-cycloalkyl or up to three fluoro atoms,
    and
    (ii) said $(C_3-C_6)$-cycloalkyl is optionally substituted with one or two substituents independently selected from the group consisting of $(C_1-C_4)$-alkyl, hydroxy and amino,
    and
    (iii) said phenyl is optionally substituted with one or two substituents independently selected from the group consisting of fluoro, chloro, bromo, cyano, trifluoromethyl, trifluoromethoxy, $(C_1-C_4)$-alkyl and $(C_1-C_4)$-alkoxy, $R^4$ is hydrogen or $(C_1-C_4)$-alkyl,
$R^5$ is hydrogen, $(C_1-C_4)$-alkyl, $(C_1-C_4)$-alkylcarbonyl, $(C_3-C_6)$-cycloalkyl or 4- to 6-membered heterocycloalkyl, wherein
  (i) said $(C_1-C_4)$-alkyl is optionally substituted with hydroxy, $(C_1-C_4)$-alkoxy, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl or $(C_3-C_6)$-cycloalkyl,
  and
  (ii) said $(C_3-C_6)$-cycloalkyl is optionally substituted with one or two substituents independently selected from the group consisting of $(C_1-C_4)$-alkyl, hydroxy and amino,
  and
  (iii) said 4- to 6-membered heterocycloalkyl is optionally substituted with one or two substituents independently selected from the group consisting of $(C_1-C_4)$-alkyl, hydroxy, oxo and amino,
$R^6$ is hydrogen, $(C_1-C_4)$-alkyl, $(C_3-C_6)$-cycloalkyl or 4- to 6-membered heterocycloalkyl, wherein
  (i) said $(C_1-C_4)$-alkyl is optionally substituted with hydroxy, $(C_1-C_4)$-alkoxy, hydroxycarbonyl, $(C_1-C_4)$-alkoxycarbonyl, amino, aminocarbonyl, mono-$(C_1-C_4)$-alkylaminocarbonyl, di-$(C_1-C_4)$-alkylaminocarbonyl or $(C_3-C_6)$-cycloalkyl,
  and
  (ii) said $(C_3-C_6)$-cycloalkyl is optionally substituted with one or two substituents independently selected from the group consisting of $(C_1-C_4)$-alkyl, hydroxy and amino,
  and
  (iii) said 4- to 6-membered heterocycloalkyl is optionally substituted with one or two substituents independently selected from the group consisting of $(C_1-C_4)$-alkyl, hydroxy, oxo and amino,
or
$R^4$ and $R^5$, or $R^4$ and $R^6$, respectively, are joined and, taken together with the nitrogen atom to which they are attached, form a monocyclic, saturated 4- to 7-membered heterocycloalkyl ring which may contain a second ring heteroatom selected from $N(R^7)$ and O, and which may be substituted on ring carbon atoms with one or two substituents independently selected from the group consisting of $(C_1-C_4)$-alkyl, oxo, hydroxy, amino and aminocarbonyl, and wherein
  $R^7$ is hydrogen, $(C_1-C_4)$-alkyl, formyl or $(C_1-C_4)$-alkylcarbonyl, and
$G^2$ represents chloro, cyano, $(C_1-C_4)$-alkyl, or the group —$CR^{8A}R^{8B}$—OH, —$CH_2$—$NR^9R^{10}$, —C(=O)—$NR^{11}R^{12}$ or —$CH_2$—$OR^{15}$, wherein
$R^{8A}$ and $R^{8B}$ are independently selected from the group consisting of hydrogen, $(C_1-C_4)$-alkyl, cyclopropyl and cyclobutyl,
$R^9$ is hydrogen or $(C_1-C_4)$-alkyl,
$R^{10}$ is hydrogen, $(C_1-C_4)$-alkyl, $(C_1-C_4)$-alkylcarbonyl, $(C_3-C_6)$-cycloalkyl or 4- to 6-membered heterocycloalkyl, wherein
  (i) said $(C_1-C_4)$-alkyl is optionally substituted with hydroxy, amino, aminocarbonyl, mono-$(C_1-C_4)$-alkylaminocarbonyl or di-$(C_1-C_4)$-alkylaminocarbonyl,
  and
  (ii) said $(C_3-C_6)$-cycloalkyl is optionally substituted with one or two independently selected from the group consisting of $(C_1-C_4)$-alkyl, hydroxy and amino,
and
(iii) said 4- to 6-membered heterocycloalkyl is optionally substituted with one or two substituents independently selected from the group consisting of $(C_1-C_4)$-alkyl, hydroxy, oxo and amino, $R^{11}$ is hydrogen or $(C_1-C_4)$-alkyl, $R^{12}$ is hydrogen, $(C_1-C_4)$-alkyl, $(C_3-C_6)$-cycloalkyl or 4- to 6-membered heterocycloalkyl, wherein
(i) said $(C_1-C_4)$-alkyl is optionally substituted with hydroxy, amino, aminocarbonyl, mono-$(C_1-C_4)$-alkylaminocarbonyl or di-$(C_1-C_4)$-alkylaminocarbonyl,
and
(ii) said $(C_3-C_6)$-cycloalkyl is optionally substituted with one or two substituents independently selected from the group consisting of $(C_1-C_4)$-alkyl, hydroxy and amino,
and
(iii) said 4- to 6-membered heterocycloalkyl is optionally substituted with one or two substituents independently selected from the group consisting of $(C_1-C_4)$-alkyl, hydroxy, oxo and amino,
or $R^9$ and $R^{10}$, or $R^{11}$ and $R^{12}$, respectively, are joined and, taken together with the nitrogen atom to which they are attached, form a monocyclic, saturated 4- to 7-membered heterocycloalkyl ring which may contain a second ring heteroatom selected from $N(R^{13})$, O, S and $S(O)_2$, and which may be substituted on ring carbon atoms with up to three substituents independently selected from the group consisting of fluoro, $(C_1-C_4)$-alkyl, oxo, hydroxy, amino and aminocarbonyl, and wherein
$R^{13}$ is hydrogen, $(C_1-C_4)$-alkyl, $(C_3-C_6)$-cycloalkyl, formyl or $(C_1-C_4)$-alkylcarbonyl,
and
$R^{15}$ is $(C_1-C_4)$-alkyl,
with the proviso that $G^1$ is not chloro when $G^2$ is chloro or cyano,
or a physiologically acceptable salt, solvate, hydrate or stereoisomer thereof;

said compounds are published as compounds of general formula (I) in International patent application PCT/EP2012/074977, published as WO 2013/087578 on Jun. 20, 2013, which is incorporated herein by reference in its entirety. In WO 2013/087578, said compounds of general formula (I) are described on pp. 5 et seq., pp. 13 et seq. and pp. 109 et seq., they may be synthesized according to the methods given therein on pp. 19, et seq. and pp. 53 et seq., and are exemplified as specific compound Examples 1 to 127 therein on pp. 109 to 205. Biological test data for certain of said compounds are given therein on pp. 206 to 226.

The definitions used in relation to the structure (B) in this text are as follows:

$(C_1-C_4)$-Alkyl in the context of the invention represents a straight-chain or branched alkyl radical having 1 to 4 carbon atoms. There may be mentioned by way of example and preferably: methyl, ethyl, n-propyl, isopropyl, n-butyl, iso-butyl, sec-butyl, and tert-butyl.

$(C_1-C_4)$-Alkoxy in the context of the invention represents a straight-chain or branched alkoxy radical having 1 to 4 carbon atoms. There may be mentioned by way of example and preferably: methoxy, ethoxy, n-propoxy, isopropoxy, n-butoxy, iso-butoxy, sec-butoxy, and tert-butoxy.

Mono-$(C_1-C_4)$-alkylamino in the context of the invention represents an amino group with a straight-chain or branched alkyl substituent which contains 1 to 4 carbon atoms. There may be mentioned by way of example and preferably: methylamino, ethylamino, n-propylamino, isopropylamino, n-butylamino, and tert-butylamino.

Di-$(C_1-C_4)$-alkylamino in the context of the invention represents an amino group with two identical or different straight-chain or branched alkyl substituents which each contain 1 to 4 carbon atoms. There may be mentioned by way of example and preferably: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino, and N-tert-butyl-N-methylamino.

$(C_1-C_4)$-Alkylcarbonyl in the context of the invention represents a straight-chain or branched alkyl radical having 1 to 4 carbon atoms which is bonded to the rest of the molecule via a carbonyl group [—C(=O)—]. There may be mentioned by way of example and preferably: acetyl, propionyl, n-butyryl, iso-butyryl, n-pentanoyl, and pivaloyl.

$(C_1-C_4)$-Alkoxycarbonyl in the context of the invention represents a straight-chain or branched alkoxy radical having 1 to 4 carbon atoms which is bonded to the rest of the molecule via a carbonyl group [—C(=O)—]. There may be mentioned by way of example and preferably: methoxycarbonyl, ethoxycarbonyl, n-propoxycarbonyl, isopropoxycarbonyl, n-butoxycarbonyl, and tert-butoxycarbonyl.

Mono-$(C_1-C_4)$-alkylaminocarbonyl in the context of the invention represents an amino group which is bonded to the rest of the molecule via a carbonyl group [—C(=O)—] and which has a straight-chain or branched alkyl substituent having 1 to 4 carbon atoms. There may be mentioned by way of example and preferably: methylaminocarbonyl, ethylaminocarbonyl, n-propylaminocarbonyl, isopropylaminocarbonyl, n-butylamino-carbonyl, and tert-butylaminocarbonyl.

Di-$(C_1-C_4)$-alkylaminocarbonyl in the context of the invention represents an amino group which is bonded to the rest of the molecule via a carbonyl group [—C(=O)—] and which has two identical or different straight-chain or branched alkyl substituents having in each case 1 to 4 carbon atoms. There may be mentioned by way of example and preferably: N,N-dimethylaminocarbonyl, N,N-diethylaminocarbonyl, N-ethyl-N-methyl-aminocarbonyl, N-methyl-N-n-propylaminocarbonyl, N-isopropyl-N-methylamino-carbonyl, N,N-diisopropylaminocarbonyl, N-n-butyl-N-methylaminocarbonyl, and N-tert-butyl-N-methylaminocarbonyl.

$(C_3-C_6)$-Cycloalkyl in the context of the invention represents a monocyclic, saturated carbocycle having 3 to 6 ring carbon atoms. There may be mentioned by way of example: cyclopropyl, cyclobutyl, cyclopentyl, and cyclohexyl. Preferred are cyclopropyl and cyclobutyl.

4- to 7-membered heterocycloalkyl and 4- to 6-membered heterocycloalkyl in the context of the invention represent a monocyclic, saturated heterocycle with 4 to 7 or, respectively, 4 to 6 ring atoms in total, which contains one or two identical or different ring heteroatoms from the series N, O, S and $S(O)_2$, and which can be bonded via a ring carbon atom or via a ring nitrogen atom (if present). 4- to 6-membered heterocycloalkyl containing one ring nitrogen atom and optionally one further ring heteroatom from the series N, O or $S(O)_2$ is preferred. 5- or 6-membered heterocycloalkyl containing one ring nitrogen atom and optionally one further ring heteroatom from the series N or O is particularly preferred. There may be mentioned by way of example: azetidinyl, oxetanyl, thietanyl, pyrrolidinyl, pyrazolidinyl, imidazolidinyl, tetrahydrofuranyl, thiolanyl, 1,1-dioxidothiolanyl, 1,2-oxazolidinyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl, thiomorpholinyl, 1,1-dioxidothiomorpholinyl, azepanyl, 1,4-diazepanyl, and 1,4-oxazepanyl. Preferred are azetidinyl, pyrrolidinyl, pyrazolidinyl, imidazolidinyl, 1,2-oxazolidinyl, 1,3-oxazolidinyl, piperidinyl, piperazinyl, 1,2-oxazinanyl, morpholinyl, and thiomorpholinyl. Particularly preferred are pyrrolidinyl, piperidinyl, piperazinyl, and morpholinyl.

5-membered aza-heteroaryl in the context of the invention represents an aromatic heterocyclic radical (heteroaromatic) having 5 ring atoms in total, which contains at least one ring nitrogen atom and optionally one or two further ring heteroatoms from the series N, O and/or S, and which is bonded via a ring carbon atom or optionally via a ring nitrogen atom (when allowed by valency). 5-membered aza-heteroaryl containing one ring nitrogen atom and one or two further ring heteroatoms from the series N and/or O is preferred. There may be mentioned by way of example: pyrrolyl, pyrazolyl, imidazolyl, oxazolyl, thiazolyl, isoxazolyl, isothiazolyl, triazolyl, oxadiazolyl, and thiadiazolyl. Preferred are pyrazolyl, imidazolyl, oxazolyl, isoxazolyl, and oxadiazolyl. An oxo substituent in the context of the invention represents an oxygen atom, which is bonded to a carbon atom via a double bond.

Said component B may be in the form of a pharmaceutical formulation which is ready for use to be administered simultaneously, concurrently, separately or sequentially. The components may be administered independently of one another by the oral, intravenous, topical, local installations, intraperitoneal or nasal route.

In accordance with another embodiment of the above-mentioned aspects of the present invention, said combinations are of:

component B: which is one or more substituted 5-(1-benzothiophen-2-yl)pyrrolo[2,1-f][1,2,4]-triazin-4-amine compounds of general formula (B), supra, which is selected from the list consisting of:

Example 1

4-{[4-Amino-6-(methoxymethyl)-5-(7-methoxy-5-methyl-1-benzothiophen-2-yl)pyrrolo[2,1-f][1,2,4]triazin-7-yl]methyl}piperazin-2-one Example 2

4-{[4-Amino-6-(methoxymethyl)-5-(7-methoxy-5-methyl-1-benzothiophen-2-yl)pyrrolo[2,1-f][1,2,4]triazin-7-yl]methyl}piperazin-2-one dihydrochloride Example 3

(3R)-3-({[4-Amino-6-(methoxymethyl)-5-(7-methoxy-5-methyl-1-benzothiophen-2-yl)pyrrolo[2,1-f][1,2,4]triazin-7-yl]methyl}amino)pyrrolidin-2-one dihydrochloride Example 4

(3R)-3-({[4-Amino-6-(methoxymethyl)-5-(7-methoxy-5-methyl-1-benzothiophen-2-yl)pyrrolo[2,1-f][1,2,4]triazin-7-yl]methyl}amino)pyrrolidin-2-one Example 5

4-{[4-Amino-6-(ethoxymethyl)-5-(7-methoxy-5-methyl-1-benzothiophen-2-yl)pyrrolo[2,1-f][1,2,4]triazin-7-yl]methyl}piperazin-2-one Example 6

4-{[4-Amino-6-(ethoxymethyl)-5-(7-methoxy-5-methyl-1-benzothiophen-2-yl)pyrrolo-[2,1-f][1,2,4]triazin-7-yl]methyl}piperazin-2-one dihydrochloride Example 7

(3R)-3-({[4-Amino-6-(ethoxymethyl)-5-(7-methoxy-5-methyl-1-benzothiophen-2-yl)pyrrolo[2,1-f][1,2,4]triazin-7-yl]methyl}amino)pyrrolidin-2-one dihydrochloride Example 8

(3R)-3-({[4-Amino-6-(ethoxymethyl)-5-(7-methoxy-5-methyl-1-benzothiophen-2-yl)pyrrolo[2,1-f][1,2,4]triazin-7-yl]methyl}amino)pyrrolidin-2-one Example 9

$N^2$-{[4-Amino-6-(ethoxymethyl)-5-(7-methoxy-5-methyl-1-benzothiophen-2-yl)pyrrolo[2,1-f][1,2,4]triazin-7-yl]methyl}glycinamide dihydrochloride Example 10

6-(Ethoxymethyl)-5-(7-methoxy-5-methyl-1-benzothiophen-2-yl)-7-(morpholin-4-ylmethyl)pyrrolo[2,1-f][1,2,4]triazin-4-amine Example 11

1-(4-{[4-Amino-6-(ethoxymethyl)-5-(7-methoxy-5-methyl-1-benzothiophen-2-yl)pyrrolo[2,1-f][1,2,4]triazin-7-yl]methyl}piperazin-1-yl)ethanone dihydrochloride Example 12

[4-Amino-5-(7-methoxy-5-methyl-1-benzothiophen-2-yl)-7-(piperazin-1-ylmethyl)pyrrolo[2,1-f][1,2,4]triazin-6-yl]methanol bis(formiate)

Example 13

4-{[4-Amino-6-(hydroxymethyl)-5-(7-methoxy-5-methyl-1-benzothiophen-2-yl)pyrrolo[2,1-f][1,2,4]triazin-7-yl]methyl}piperazin-2-one Example 14

7-{[(3S)-3-Amino-3-methylpyrrolidin-1-yl]methyl}-6-(methoxymethyl)-5-(7-methoxy-5-methyl-1-benzothiophen-2-yl)pyrrolo[2,1-f][1,2,4]triazin-4-amine trihydrochloride Example 15

7-{[(3S)-3-Amino-3-methylpyrrolidin-1-yl]methyl}-6-(ethoxymethyl)-5-(7-methoxy-5-methyl-1-benzothiophen-2-yl)pyrrolo[2,1-f][1,2,4]triazin-4-amine

Example 16

1-(4-{[4-Amino-6-(methoxymethyl)-5-(7-methoxy-5-methyl-1-benzothiophen-2-yl)pyrrolo[2,1-f][1,2,4]triazin-7-yl]methyl}piperazin-1-yl)ethanone dihydrochloride

Example 17

6-(Methoxymethyl)-5-(7-methoxy-5-methyl-1-benzothiophen-2-yl)-7-(piperazin-1-ylmethyl)pyrrolo[2,1-f][1,2,4]triazin-4-amine formiate

Example 18

6-(Ethoxymethyl)-5-(7-methoxy-5-methyl-1-benzothiophen-2-yl)-7-(piperazin-1-ylmethyl)pyrrolo[2,1-f][1,2,4]triazin-4-amine

Example 19

6-(Ethoxymethyl)-5-(7-methoxy-5-methyl-1-benzothiophen-2-yl)-7-(piperazin-1-ylmethyl)pyrrolo[2,1-f][1,2,4]triazin-4-amine dihydrochloride

Example 20

1-(4-{[4-Amino-6-(ethoxymethyl)-5-(7-methoxy-5-methyl-1-benzothiophen-2-yl)pyrrolo-[2,1-f][1,2,4]triazin-7-yl]methyl}piperazin-1-yl)ethanone

Example 21

4-({4-Amino-6-[(2-hydroxyethoxy)methyl]-5-(7-methoxy-5-methyl-1-benzothiophen-2-yl)pyrrolo[2,1-f][1,2,4]triazin-7-yl}methyl)piperazin-2-one formiate

Example 22

2-{[4-Amino-5-(7-methoxy-5-methyl-1-benzothiophen-2-yl)-7-(piperazin-1-ylmethyl)pyrrolo[2,1-f][1,2,4]triazin-6-yl]methoxy}ethanol dihydrochloride

Example 23

6-(Butoxymethyl)-5-(7-methoxy-5-methyl-1-benzothiophen-2-yl)-7-(piperazin-1-ylmethyl)pyrrolo[2,1-f][1,2,4]triazin-4-amine formiate

Example 24

5-(7-Methoxy-5-methyl-1-benzothiophen-2-yl)-7-(piperazin-1-ylmethyl)-6-(propoxy-methyl)pyrrolo[2,1-f][1,2,4]triazin-4-amine bis(formiate)

Example 25

6-[(Cyclopropylmethoxy)methyl]-5-(7-methoxy-5-methyl-1-benzothiophen-2-yl)-7-(piperazin-1-ylmethyl)pyrrolo[2,1-f][1,2,4]triazin-4-amine bis(formiate)

Example 26

6-[(Cyclobutyloxy)methyl]-5-(7-methoxy-5-methyl-1-benzothiophen-2-yl)-7-(piperazin-1-ylmethyl)pyrrolo[2,1-f][1,2,4]triazin-4-amine

Example 27

6-(Isopropoxymethyl)-5-(7-methoxy-5-methyl-1-benzothiophen-2-yl)-7-(piperazin-1-yl-methyl)pyrrolo[2,1-f][1,2,4]triazin-4-amine formiate

Example 28

6-[(2-Methoxyethoxy)methyl]-5-(7-methoxy-5-methyl-1-benzothiophen-2-yl)-7-(piperazin-1-ylmethyl)pyrrolo[2,1-f][1,2,4]triazin-4-amine formiate

Example 29

5-(7-Methoxy-5-methyl-1-benzothiophen-2-yl)-7-(piperazin-1-ylmethyl)-6-[(2,2,2-trifluoroethoxy)methyl]pyrrolo[2,1-f][1,2,4]triazin-4-amine formiate

Example 30

6-[(2-Aminoethoxy)methyl]-5-(7-methoxy-5-methyl-1-benzothiophen-2-yl)-7-(piperazin-1-ylmethyl)pyrrolo[2,1-f][1,2,4]triazin-4-amine trihydrochloride

Example 31

Methyl {[4-amino-5-(7-methoxy-5-methyl-1-benzothiophen-2-yl)-7-(piperazin-1-yl-methyl)pyrrolo[2,1-f][1,2,4]triazin-6-yl]methoxy}acetate

Example 32

{[4-Amino-5-(7-methoxy-5-methyl-1-benzothiophen-2-yl)-7-(piperazin-1-ylmethyl)pyrrolo[2,1-f][1,2,4]triazin-6-yl]methoxy}acetic acid

Example 33

2-{[4-Amino-5-(7-methoxy-5-methyl-1-benzothiophen-2-yl)-7-(piperazin-1-ylmethyl)pyrrolo[2,1-f][1,2,4]triazin-6-yl]methoxy}acetamide

Example 34

2-({7-[(4-Acetylpiperazin-1-yl)methyl]-4-amino-5-(7-methoxy-5-methyl-1-benzothiophen-2-yl)pyrrolo[2,1-f][1,2,4]triazin-6-yl}methoxy)acetamide

Example 35

5-(7-Methoxy-5-methyl-1-benzothiophen-2-yl)-6-(phenoxymethyl)-7-(piperazin-1-yl-methyl)pyrrolo[2,1-f][1,2,4]triazin-4-amine bis(formiate)

Example 36

5-(7-Methoxy-5-methyl-1-benzothiophen-2-yl)-6-[(methylamino)methyl]-7-(piperazin-1-ylmethyl)pyrrolo[2,1-f][1,2,4]triazin-4-amine trihydrochloride

Example 37

6-[(Dimethylamino)methyl]-5-(7-methoxy-5-methyl-1-benzothiophen-2-yl)-7-(piperazin-1-ylmethyl)pyrrolo[2,1-f][1,2,4]triazin-4-amine trihydrochloride

Example 38

6-[(Ethylamino)methyl]-5-(7-methoxy-5-methyl-1-benzothiophen-2-yl)-7-(piperazin-1-ylmethyl)pyrrolo[2,1-f][1,2,4]triazin-4-amine trihydrochloride

Example 39

2-({[4-Amino-5-(7-methoxy-5-methyl-1-benzothiophen-2-yl)-7-(piperazin-1-ylmethyl)pyrrolo[2,1-f][1,2,4]triazin-6-yl]methyl}amino)ethanol trihydrochloride

Example 40 rac-1-{[4-Amino-5-(7-methoxy-5-methyl-1-benzothiophen-2-yl)-7-(piperazin-1-ylmethyl)pyrrolo[2,1-f][1,2,4]triazin-6-yl]methyl}piperidin-3-ol trihydrochloride

Example 41

1-{[4-Amino-5-(7-methoxy-5-methyl-1-benzothiophen-2-yl)-7-(piperazin-1-ylmethyl)pyrrolo[2,1-f][1,2,4]triazin-6-yl]methyl}piperidin-4-ol trihydrochloride

Example 42 rac-1-{[4-Amino-5-(7-methoxy-5-methyl-1-benzothiophen-2-yl)-7-(piperazin-1-ylmethyl)pyrrolo[2,1-f][1,2,4]triazin-6-yl]methyl}pyrrolidin-3-ol trihydrochloride

Example 43

6-[(Diethylamino)methyl]-5-(7-methoxy-5-methyl-1-benzothiophen-2-yl)-7-(piperazin-1-ylmethyl)pyrrolo[2,1-f][1,2,4]triazin-4-amine trihydrochloride

Example 44

6-[(Cyclobutylamino)methyl]-5-(7-methoxy-5-methyl-1-benzothiophen-2-yl)-7-(piperazin-1-ylmethyl)pyrrolo[2,1-f][1,2,4]triazin-4-amine trihydrochloride

Example 45

5-(7-Methoxy-5-methyl-1-benzothiophen-2-yl)-7-(piperazin-1-ylmethyl)-6-(pyrrolidin-1-ylmethyl)pyrrolo[2,1-f][1,2,4]triazin-4-amine trihydrochloride

Example 46

6-[(Cyclopropylamino)methyl]-5-(7-methoxy-5-methyl-1-benzothiophen-2-yl)-7-(piperazin-1-ylmethyl)pyrrolo[2,1-f][1,2,4]triazin-4-amine trihydrochloride

Example 47

6-{[(Cyclopropylmethyl)amino]methyl}-5-(7-methoxy-5-methyl-1-benzothiophen-2-yl)-7-(piperazin-1-ylmethyl)pyrrolo[2,1-f][1,2,4]triazin-4-amine trihydrochloride

Example 48

N-{[4-Amino-5-(7-methoxy-5-methyl-1-benzothiophen-2-yl)-7-(piperazin-1-ylmethyl)pyrrolo[2,1-f][1,2,4]triazin-6-yl]methyl}glycine trihydrochloride

Example 49

4-{[4-Amino-5-(7-methoxy-5-methyl-1-benzothiophen-2-yl)-7-(piperazin-1-ylmethyl)pyrrolo[2,1-f][1,2,4]triazin-6-yl]methyl}piperazin-2-one trihydrochloride

Example 50

[4-Amino-5-(7-methoxy-5-methyl-1-benzothiophen-2-yl)-7-(morpholin-4-ylmethyl)pyrrolo[2,1-f][1,2,4]triazin-6-yl]methanol

Example 51

(3S)-3-({[4-Amino-5-(7-methoxy-5-methyl-1-benzothiophen-2-yl)-7-(morpholin-4-ylmethyl)pyrrolo[2,1-f][1,2,4]triazin-6-yl]methyl}amino)pyrrolidin-2-one

Example 52

4-{[4-Amino-5-(7-methoxy-5-methyl-1-benzothiophen-2-yl)-7-(morpholin-4-ylmethyl)pyrrolo[2,1-f][1,2,4]triazin-6-yl]methyl}piperazin-2-one

Example 53 rac-1-({[4-Amino-5-(7-methoxy-5-methyl-1-benzothiophen-2-yl)-7-(morpholin-4-ylmethyl)pyrrolo[2,1-f][1,2,4]triazin-6-yl]methyl}amino)propan-2-ol

Example 54

1-({[4-Amino-5-(7-methoxy-5-methyl-1-benzothiophen-2-yl)-7-(morpholin-4-ylmethyl)-pyrrolo[2,1-f][1,2,4]triazin-6-yl]methyl}amino)-2-methylpropan-2-ol

Example 55

1-(4-{[4-Amino-6-(hydroxymethyl)-5-(7-methoxy-5-methyl-1-benzothiophen-2-yl)pyrrolo[2,1-f][1,2,4]triazin-7-yl]methyl}piperazin-1-yl)ethanone

Example 56

(3R)-3-[({7-[(4-Acetylpiperazin-1-yl)methyl]-4-amino-5-(7-methoxy-5-methyl-1-benzothiophen-2-yl)pyrrolo[2,1-f][1,2,4]triazin-6-yl}methyl)amino]pyrrolidin-2-one

Example 57

1-(4-{[4-Amino-6-{[(2-hydroxy-2-methylpropyl)amino]methyl}-5-(7-methoxy-5-methyl-1-benzothiophen-2-yl)pyrrolo[2,1-f][1,2,4]triazin-7-yl]methyl}piperazin-1-yl)ethanone

Example 58

4-({4-Amino-5-(7-methoxy-5-methyl-1-benzothiophen-2-yl)-6-[(3-oxopiperazin-1-yl)-methyl]pyrrolo[2,1-f][1,2,4]triazin-7-yl}methyl)piperazine-1-carbaldehyde formiate

Example 59

4-({7-[(4-Acetylpiperazin-1-yl)methyl]-4-amino-5-(7-methoxy-5-methyl-1-benzothiophen-2-yl)pyrrolo[2,1-f][1,2,4]triazin-6-yl}methyl)piperazin-2-one

Example 60

Methyl 4-amino-5-(7-methoxy-5-methyl-1-benzothiophen-2-yl)-7-(piperazin-1-ylcarbonyl)pyrrolo[2,1-f][1,2,4]triazine-6-carboxylate bis(formate)

Example 61

5-(7-Methoxy-5-methyl-1-benzothiophen-2-yl)-6-(1,3-oxazol-5-yl)-7-(piperazin-1-ylmethyl)pyrrolo[2,1-f][1,2,4]triazin-4-amine trihydrochloride

Example 62

6-(Aminomethyl)-5-(7-methoxy-5-methyl-1-benzothiophen-2-yl)-7-(piperazin-1-ylmethyl)pyrrolo[2,1-f][1,2,4]triazin-4-amine trihydrochloride

Example 63

N-{[4-Amino-5-(7-methoxy-5-methyl-1-benzothiophen-2-yl)-7-(piperazin-1-ylmethyl)pyrrolo[2,1-f][1,2,4]triazin-6-yl]methyl}acetamide bis(trifluoroacetate)

Example 64

N-{[4-Amino-5-(7-methoxy-5-methyl-1-benzothiophen-2-yl)-7-(piperazin-1-ylmethyl)pyrrolo[2,1-f][1,2,4]triazin-6-yl]methyl}acetamide dihydrochloride

Example 65

N-({4-Amino-7-[(4-formylpiperazin-1-yl)methyl]-5-(7-methoxy-5-methyl-1-benzothiophen-2-yl)pyrrolo[2,1-f][1,2,4]triazin-6-yl}methyl)acetamide formiate

Example 66

N-({7-[(4-Acetylpiperazin-1-yl)methyl]-4-amino-5-(7-methoxy-5-methyl-1-benzothiophen-2-yl)pyrrolo[2,1-f][1,2,4]triazin-6-yl}methyl)acetamide

Example 67

N-({4-Amino-5-(7-methoxy-5-methyl-1-benzothiophen-2-yl)-7-[(3-oxopiperazin-1-yl)methyl]pyrrolo[2,1-f][1,2,4]triazin-6-yl}methyl)acetamide

Example 68

4-Amino-6-(hydroxymethyl)-5-(7-methoxy-5-methyl-1-benzothiophen-2-yl)pyrrolo[2,1-f][1,2,4]triazine-7-carbonitrile

Example 69

4-Amino-6-(methoxymethyl)-5-(7-methoxy-5-methyl-1-benzothiophen-2-yl)pyrrolo[2,1-f][1,2,4]triazine-7-carbonitrile

Example 70

4-Amino-6-(ethoxymethyl)-5-(7-methoxy-5-methyl-1-benzothiophen-2-yl)pyrrolo[2,1-f][1,2,4]triazine-7-carbonitrile

Example 71

4-Amino-5-(7-methoxy-5-methyl-1-benzothiophen-2-yl)-6-[(3-oxopiperazin-1-yl)methyl]pyrrolo[2,1-f][1,2,4]triazine-7-carbonitrile

Example 72

N,N'-{[4-Amino-5-(7-methoxy-5-methyl-1-benzothiophen-2-yl)pyrrolo[2,1-f][1,2,4]triazine-6,7-diyl]bis(methylene)}diacetamide

Example 73

2-[4-Amino-6-(hydroxymethyl)-5-(7-methoxy-5-methyl-1-benzothiophen-2-yl)pyrrolo[2,1-f][1,2,4]triazin-7-yl]propan-2-ol

Example 74

4-{[4-Amino-7-(2-hydroxypropan-2-yl)-5-(7-methoxy-5-methyl-1-benzothiophen-2-yl)pyrrolo[2,1-f][1,2,4]triazin-6-yl]methyl}piperazin-2-one

Example 75

[4-Amino-5-(7-methoxy-5-methyl-1-benzothiophen-2-yl)-7-methylpyrrolo[2,1-f][1,2,4]triazin-6-yl]methanol

Example 76

4-{[4-Amino-5-(7-methoxy-5-methyl-1-benzothiophen-2-yl)-7-methylpyrrolo[2,1-f][1,2,4]triazin-6-yl]methyl}piperazin-2-one

Example 77

1-({[4-Amino-5-(7-methoxy-5-methyl-1-benzothiophen-2-yl)-7-methylpyrrolo[2,1-f][1,2,4]triazin-6-yl]methyl}amino)-2-methylpropan-2-ol formiate

Example 78

1-({[4-Amino-5-(7-methoxy-5-methyl-1-benzothiophen-2-yl)-7-methylpyrrolo[2,1-f][1,2,4]triazin-6-yl]methyl}amino)-2-methylpropan-2-ol

Example 79

[4-Amino-7-chloro-5-(7-methoxy-5-methyl-1-benzothiophen-2-yl)pyrrolo[2,1-f][1,2,4]triazin-6-yl]methanol

Example 80

4-{[4-Amino-7-chloro-5-(7-methoxy-5-methyl-1-benzothiophen-2-yl)pyrrolo[2,1-f][1,2,4]triazin-6-yl]methyl}piperazin-2-one

Example 81

1-({[4-Amino-7-chloro-5-(7-methoxy-5-methyl-1-benzothiophen-2-yl)pyrrolo[2,1-f][1,2,4]triazin-6-yl]methyl}amino)-2-methylpropan-2-ol formiate

Example 82

1-({[4-Amino-7-chloro-5-(7-methoxy-5-methyl-1-benzothiophen-2-yl)pyrrolo[2,1-f][1,2,4]triazin-6-yl]methyl}amino)-2-methylpropan-2-ol

Example 83

7-Chloro-6-(ethoxymethyl)-5-(7-methoxy-5-methyl-1-benzothiophen-2-yl)pyrrolo[2,1-f]-[1,2,4]triazin-4-amine

Example 84

5-(7-Methoxy-5-methyl-1-benzothiophen-2-yl)-6-methyl-7-(piperazin-1-ylmethyl)pyrrolo[2,1-f][1,2,4]triazin-4-amine formiate

Example 85

6-Chloro-5-(7-methoxy-5-methyl-1-benzothiophen-2-yl)-7-(piperazin-1-ylmethyl)pyrrolo[2,1-f][1,2,4]triazin-4-amine trihydrochloride

Example 86

[4-Amino-6-(ethoxymethyl)-5-(7-methoxy-5-methyl-1-benzothiophen-2-yl)pyrrolo[2,1-f][1,2,4]triazin-7-yl]methanol

Example 87

1-{[4-Amino-6-(ethoxymethyl)-5-(7-methoxy-5-methyl-1-benzothiophen-2-yl)pyrrolo[2,1-f][1,2,4]triazin-7-yl]methyl}imidazolidin-2-one

Example 88

4-{[4-Amino-5-(7-methoxy-1-benzothiophen-2-yl)-6-(methoxymethyl)pyrrolo[2,1-f][1,2,4]triazin-7-yl]methyl}piperazin-2-one

Example 89

4-{[4-Amino-6-(methoxymethyl)-5-(5-methyl-1-benzothiophen-2-yl)pyrrolo[2,1-f][1,2,4]triazin-7-yl]methyl}piperazin-2-one

Example 90

1-[4-Amino-6-(ethoxymethyl)-5-(7-methoxy-5-methyl-1-benzothiophen-2-yl)pyrrolo[2,1-f][1,2,4]triazin-7-yl]ethanol

Example 91

[4-Amino-6-(ethoxymethyl)-5-(7-methoxy-5-methyl-1-benzothiophen-2-yl)pyrrolo[2,1-f][1,2,4]triazin-7-yl](cyclopropyl)methanol

Example 92

(3S)-3-({[4-Amino-6-(methoxymethyl)-5-(7-methoxy-5-methyl-1-benzothiophen-2-yl)pyrrolo[2,1-f][1,2,4]triazin-7-yl]methyl}amino)pyrrolidin-2-one

Example 93

(3S)-3-({[4-Amino-6-(ethoxymethyl)-5-(7-methoxy-5-methyl-1-benzothiophen-2-yl)pyrrolo[2,1-f][1,2,4]triazin-7-yl]methyl}amino)pyrrolidin-2-one

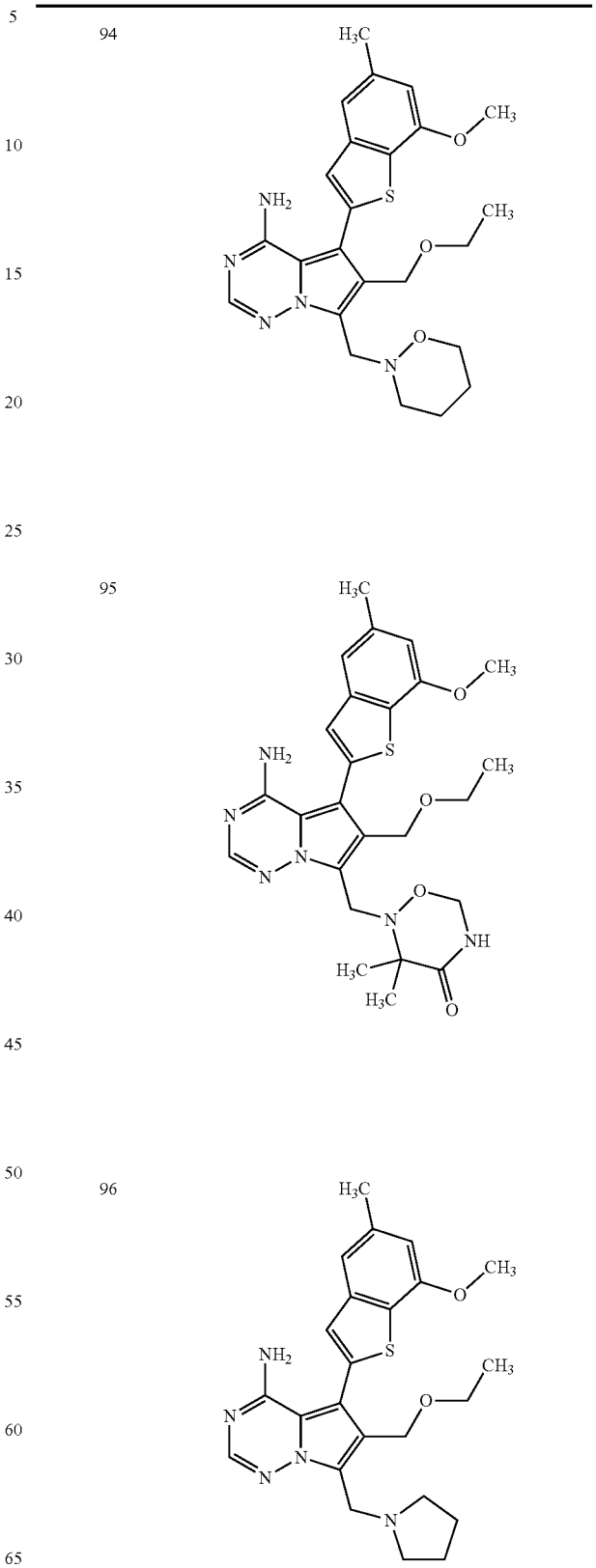

| Example No. | Structure |
|---|---|
| 94 | 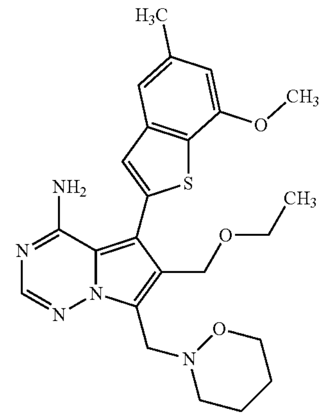 [SMILES: CCOCc1c(-c2cc3cc(C)cc(OC)c3s2)c2c(N)ncnn2c1CN1CCCCO1] |
| 95 | 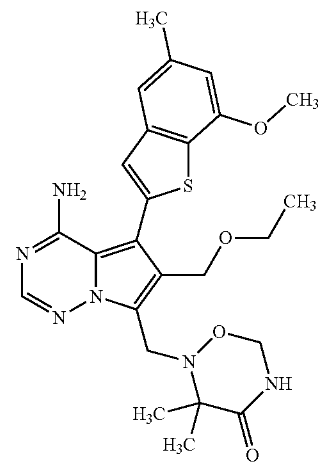 [SMILES: CCOCc1c(-c2cc3cc(C)cc(OC)c3s2)c2c(N)ncnn2c1CN1OCNC(=O)C1(C)C] |
| 96 | 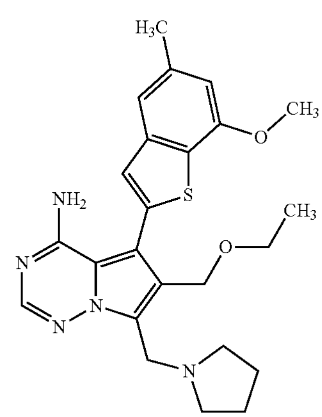 [SMILES: CCOCc1c(-c2cc3cc(C)cc(OC)c3s2)c2c(N)ncnn2c1CN1CCCC1] |

| Example No. | Structure |
|---|---|
| 97 | 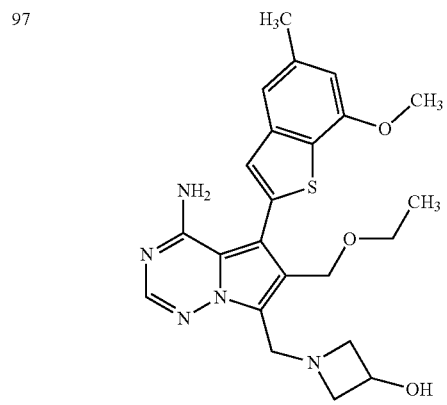 |
| 98 | 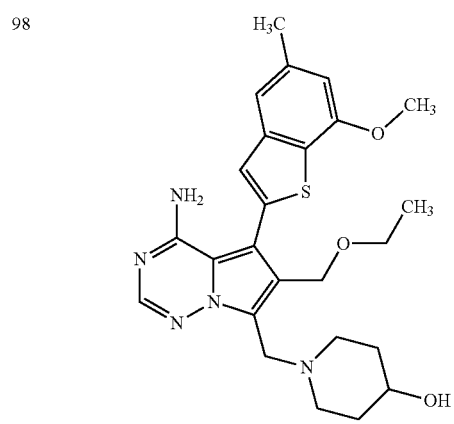 |
| 99 | 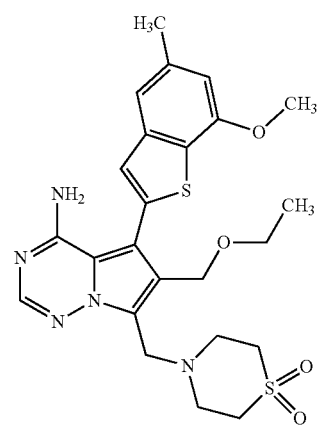 [SMILES: CCOCc1c(-c2cc3cc(C)cc(OC)c3s2)c2c(N)ncnn2c1CN1CCS(=O)(=O)CC1] |
| Example No. | Structure |
|---|---|
| 100 | 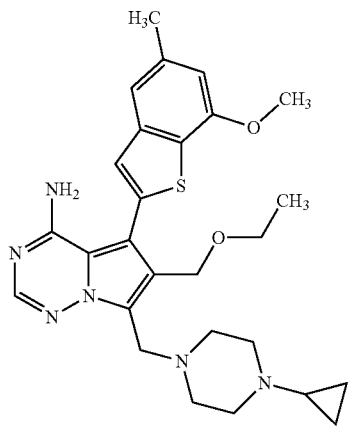 [SMILES: CCOCc1c(-c2cc3cc(C)cc(OC)c3s2)c2c(N)ncnn2c1CN1CCN(C2CC2)CC1] |
| 101 | 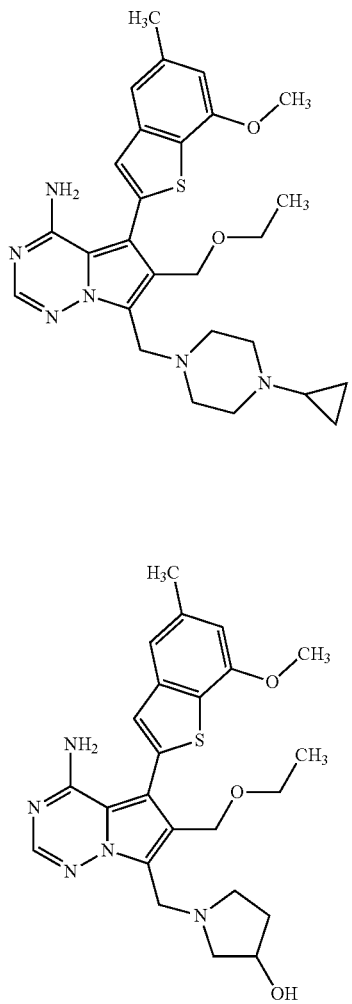 |
| 102 | 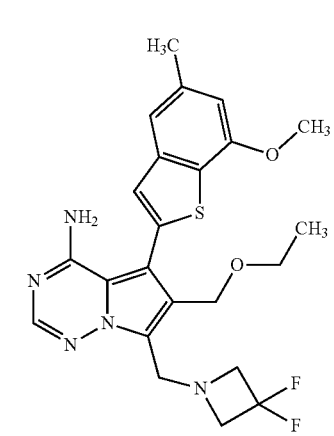 [SMILES: CCOCc1c(-c2cc3cc(C)cc(OC)c3s2)c2c(N)ncnn2c1CN1CC(F)(F)C1] |

| Example No. | Structure |
|---|---|
| 103 | 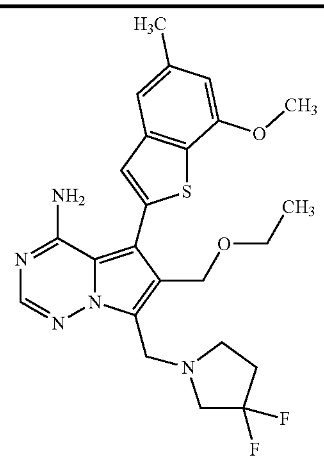 |
| 104 | 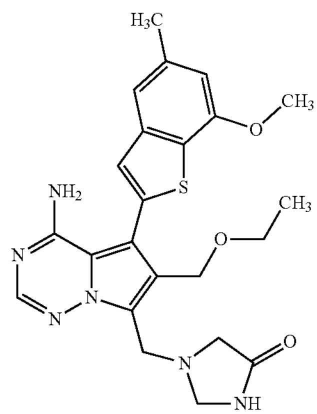 [SMILES: CCOCc1c(-c2cc3cc(C)cc(OC)c3s2)c2c(N)ncnn2c1CN1CNC(=O)C1] |
| 105 | 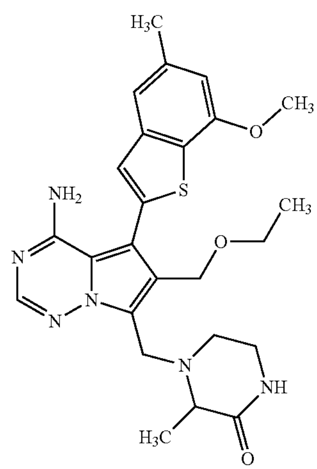 [SMILES: CCOCc1c(-c2cc3cc(C)cc(OC)c3s2)c2c(N)ncnn2c1CN1CCNC(=O)C1C] |

Example 106

4-Amino-6-(ethoxymethyl)-5-(7-methoxy-5-methyl-1-benzothiophen-2-yl)-N-[(3R)-2-oxopyrrolidin-3-yl]pyrrolo[2,1-f][1,2,4]triazine-7-carboxamide

Example 107

4-{[4-Amino-6-(ethoxymethyl)-5-(7-methoxy-5-methyl-1-benzothiophen-2-yl)pyrrolo[2,1-f][1,2,4]triazin-7-yl]carbonyl}piperazin-2-one

| Example No. | Structure |
|---|---|
| 108 | 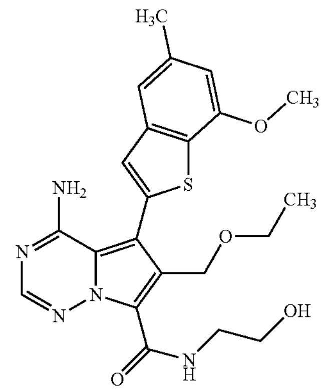 [SMILES: CCOCc1c(-c2cc3cc(C)cc(OC)c3s2)c2c(N)ncnn2c1C(=O)NCCO] |
| 109 | 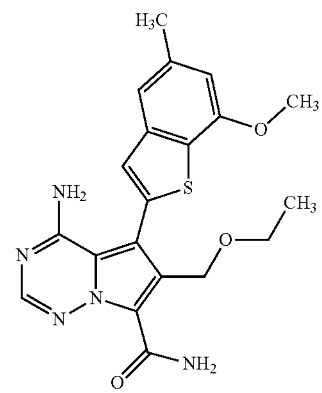 [SMILES: CCOCc1c(-c2cc3cc(C)cc(OC)c3s2)c2c(N)ncnn2c1C(N)=O] |
| 110 | 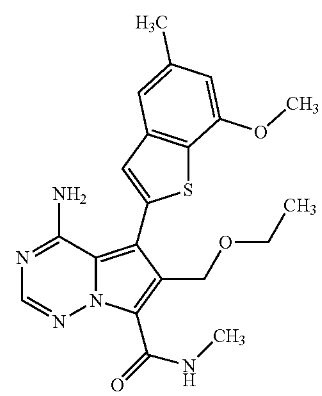 [SMILES: CCOCc1c(-c2cc3cc(C)cc(OC)c3s2)c2c(N)ncnn2c1C(=O)NC] |
| 111 | 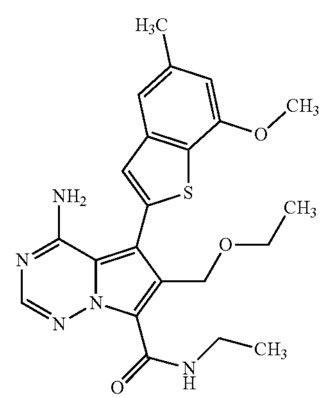 [SMILES: CCNC(=O)c1c(COCC)c(-c2cc3cc(C)cc(OC)c3s2)c2c(N)ncnn12] |

-continued

| Example No. | Structure |
| --- | --- |
| 112 | (structure) |
| 113 | (structure) |
| 114 | (structure) |

-continued

| Example No. | Structure |
| --- | --- |
| 115 | (structure) |
| 116 | (structure) |
| 117 | (structure) |

| Example No. | Structure |
|---|---|
| 118 | 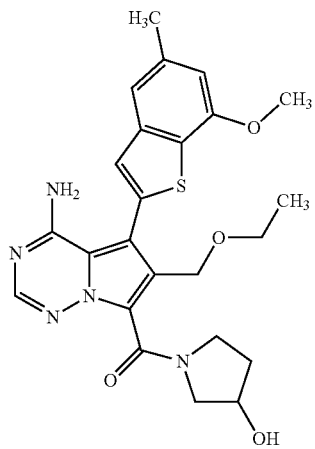 [SMILES: CCOCc1c(-c2cc3cc(C)cc(OC)c3s2)c2c(N)ncnn2c1C(=O)N1CCC(O)C1] |
| 119 | 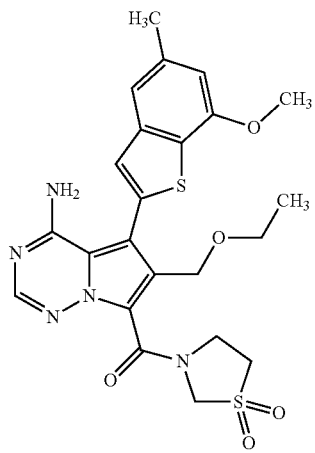 [SMILES: CCOCc1c(-c2cc3cc(C)cc(OC)c3s2)c2c(N)ncnn2c1C(=O)N1CCS(=O)(=O)C1] |
| 120 | 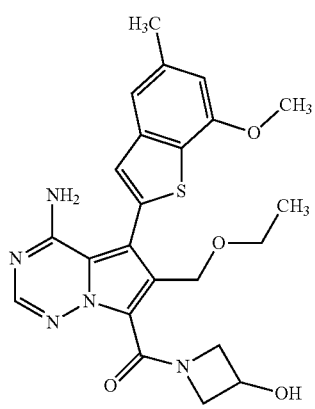 [SMILES: CCOCc1c(-c2cc3cc(C)cc(OC)c3s2)c2c(N)ncnn2c1C(=O)N1CC(O)C1] |
| Example No. | Structure |
|---|---|
| 121 | 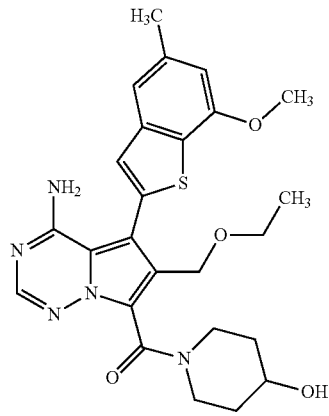 [SMILES: CCOCc1c(-c2cc3cc(C)cc(OC)c3s2)c2c(N)ncnn2c1C(=O)N1CCC(O)CC1] |
| 122 | 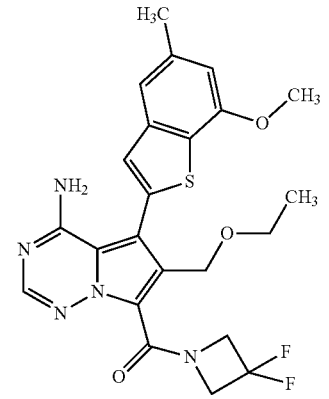 [SMILES: CCOCc1c(-c2cc3cc(C)cc(OC)c3s2)c2c(N)ncnn2c1C(=O)N1CC(F)(F)C1] |
| 123 | 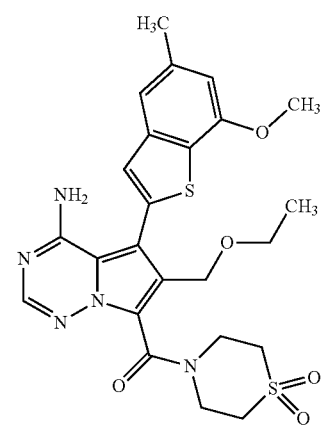 [SMILES: CCOCc1c(-c2cc3cc(C)cc(OC)c3s2)c2c(N)ncnn2c1C(=O)N1CCS(=O)(=O)CC1] |
Example 124
4-{[4-Amino-5-(5,7-dimethoxy-1-benzothiophen-2-yl)-6-(methoxymethyl)pyrrolo[2,1-f]-[1,2,4]triazin-7-yl]methyl}piperazin-2-one
Example 125
4-{[4-Amino-7-(hydroxymethyl)-5-(7-methoxy-5-methyl-1-benzothiophen-2-yl)pyrrolo[2,1-f][1,2,4]triazin-6-yl]methyl}piperazin-2-one Example 126

4-{[4-Amino-7-(methoxymethyl)-5-(7-methoxy-5-methyl-1-benzothiophen-2-yl)pyrrolo[2,1-f][1,2,4]triazin-6-yl]methyl}piperazin-2-one Example 127

4-{[4-Amino-7-(ethoxymethyl)-5-(7-methoxy-5-methyl-1-benzothiophen-2-yl)pyrrolo[2,1-f][1,2,4]triazin-6-yl]methyl}piperazin-2-one In accordance with an embodiment of the above-mentioned aspects of the present invention, said combinations are of:

component A: 2-amino-N-[7-methoxy-8-(3-morpholin-4-ylpropoxy)-2,3-dihydroimidazo[1,2-c]quinazolin-5-yl]pyrimidine-5-carboxamide; and component B: 4-{[4-Amino-6-(methoxymethyl)-5-(7-methoxy-5-methyl-1-benzothiophen-2-yl)pyrrolo[2,1-f][1,2,4]triazin-7-yl]methyl}piperazin-2-one.

Said component B may be in the form of a pharmaceutical formulation which is ready for use to be administered simultaneously, concurrently, separately or sequentially. The components may be administered independently of one another by the oral, intravenous, topical, local installations, intraperitoneal or nasal route.

In accordance with an embodiment, the present invention relates to a combination of any component A mentioned herein with any component B mentioned herein.

In a particular embodiment, the present invention relates to a combination of a component A with a component B, as mentioned in the Examples section herein.

Useful Forms of Components A and B of the Combinations of the Present Invention

As mentioned supra, either or both of components A and B of any of the combinations of the present invention may be in a useful form, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chlorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, sulfate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, or butyl chlorides, bromides and iodides; dialkyl sulfates like dimethyl, diethyl, dibutyl sulfate, or diamyl sulfates, long chain halides such as decyl, lauryl, myristyl and strearyl chlorides, bromides and iodides, aralkyl halides like benzyl and phenethyl bromides and others.

A solvate for the purpose of this invention is a complex of a solvent and a compound of the invention in the solid state. Exemplary solvates would include, but are not limited to, complexes of a compound of the invention with ethanol or methanol. Hydrates are a specific form of solvate wherein the solvent is water.

Pharmaceutical Formulations of Components A and B of the Combinations of the Present Invention As mentioned supra, the components A or B may, independently from one another, be in the form of a pharmaceutical formulation which is ready for use to be administered simultaneously, concurrently, separately or sequentially. The components may be administered independently of one another by the oral, intravenous, topical, local installations, intraperitoneal or nasal route.

Said compositions can be utilized to achieve the desired pharmacological effect by administration to a patient in need thereof. A patient, for the purpose of this invention, is a mammal, including a human, in need of treatment for the particular condition or disease. Therefore, the present invention includes combinations in which components A and B, independently of one another, are pharmaceutical formulations compositions that are comprised of a pharmaceutically acceptable carrier and a pharmaceutically effective amount of a said component. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of component, and/or combination. A pharmaceutically effective amount of a combination is preferably that amount which produces a result or exerts an influence on the particular condition being treated. The combinations of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the combinations can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the combinations of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit.

For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The combinations of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid.

Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite); emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Cancer

Within the context of the present invention, the term "cancer" includes, but is not limited to, cancers of the endometrium, breast, lung, brain, reproductive organs, digestive tract, urinary tract, liver, eye, skin, head and neck, thyroid, parathyroid and their distant metastases. Those disorders also include multiple myeloma, lymphomas, sarcomas, and leukemias.

Examples of endometrial cancer include, but not limited to type I EC (estrogen-dependent and/or progesterone-dependent with endometrioid histology) and type II EC, or endometriosis (hormone-independent poorly differentiated endometrioid, clear cell and serous carcinomas).

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

The present invention relates to a method for using the combinations of the present invention, in the treatment or prophylaxis of a cancer, particularly endometrial cancer (hereinafter abbreviated to "EC"), particularly 1st line, 2nd line, relapsed, refractory, type I or type II EC, or endometriosis. The combinations of the present invention can be utilized to inhibit, block, reduce, decrease, etc., cell proliferation and/or cell division, and/or produce apoptosis, in the treatment or prophylaxis of cancer, in particular EC (hereinafter abbreviated to "EC"), particularly 1st line, 2nd line, relapsed, refractory, type I or type II EC, or endometriosis. This method comprises administering to a mammal in need thereof, including a human, an amount of a combination of this invention, or a pharmaceutically acceptable salt, isomer, polymorph, metabolite, hydrate, solvate or ester thereof; etc. which is effective for the treatment or prophylaxis of cancer, in particular EC, particularly 1st line, 2nd line, relapsed, refractory, type I or type II EC, or endometriosis.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Dose and Administration

Based upon standard laboratory techniques known to evaluate compounds useful for the treatment or prophylaxis of cancer, in particular endometrial cancer (EC), particularly 1st line, 2nd line, relapsed, refractory, type I or type II EC, or endometriosis, by standard toxicity tests and by standard pharmacological assays for the determination of treatment of the conditions identified above in mammals, and by comparison of these results with the results of known medicaments that are used to treat these conditions, the effective dosage of the combinations of this invention can readily be determined for treatment of the indication. The amount of the active ingredient to be administered in the treatment of the condition can vary widely according to such considerations as the particular combination and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1,500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific combination employed, the age and general condition of the patient, time of administration, route of administration, rate of excretion of the drug, drug combinations, and the like. The desired mode of treatment and number of doses of a combination of the present invention or a pharmaceutically acceptable salt or ester or composition thereof can be ascertained by those skilled in the art using conventional treatment tests.

Therapies Using Combinations of Component A as Described Supra, Component B as Described Supra, and Component C: One or More Further Pharmaceutical Agents.

The combinations of component A and component B of this invention can be administered as the sole pharmaceutical agent or in combination with one or more further pharmaceutical agents where the resulting combination of components A, B and C causes no unacceptable adverse effects. For example, the combinations of components A and B of this invention can be combined with component C, i.e. one or more further pharmaceutical agents, such as known anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agents, and the like, as well as with admixtures and combinations thereof.

Component C, can be one or more pharmaceutical agents such as 1311-chTNT, abarelix, abiraterone, aclarubicin, adotrastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin, or combinations thereof.

Alternatively, said component C can be one or more further pharmaceutical agents selected from gemcitabine, paclitaxel (when component B is not itself paclitaxel), cisplatin, carboplatin, sodium butyrate, 5-FU, doxirubicin, tamoxifen, etoposide, trastumazab, gefitinib, intron A, rapamycin, 17-AAG, U0126, insulin, an insulin derivative, a PPAR ligand, a sulfonylurea drug, an α-glucosidase inhibitor, a biguanide, a PTP-1B inhibitor, a DPP-IV inhibitor, a 11-beta-HSD inhibitor, GLP-1, a GLP-1 derivative, GIP, a GIP derivative, PACAP, a PACAP derivative, secretin or a secretin derivative.

Optional anti-hyper-proliferative agents which can be added as component C to the combination of components A and B of the present invention include but are not limited to compounds listed on the cancer chemotherapy drug regimens in the 11th Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use as component C with the combination of components A and B of the present invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel (when component B is not itself paclitaxel), pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use as component C with the combination of components A and B of the present invention include but are not limited to other anti-cancer agents such as epothilone and its derivatives, irinotecan, raloxifen and topotecan.

Generally, the use of cytotoxic and/or cytostatic agents as component C in combination with a combination of components A and B of the present invention will serve to:

(1) yield better efficacy in reducing the growth of a tumor or even eliminate the tumor as compared to administration of either agent alone, (2) provide for the administration of lesser amounts of the administered chemo-therapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

Biomarkers:

Biomarkers used for patient stratification are e.g. the loss of tumor suppressor PTEN or FBXW7, either alone or in combination with another form of PI3K pathway activation selected from perturbation of any of the following alone or in combination: mutation in PIK3CA, PIK3CB, PIK3CD, PIK3CG, PIK3R1, PIK3R2, PIK3R3, PIK3R4, PIK3R5, FGFR1, FGFR2, FGFR3 and/or FGFR4; PTEN loss and alteration of PIK3CA, PIK3CB, PIK3CD, PIK3CG, PIK3R1, PIK3R2, PIK3R3, PIK3R4, PIK3R5, FGFR1, FGFR2, FGFR3 and/or FGFR4, which may be measured at either the protein level, mRNA level, or DNA level, for predicting the sensitivity and/or resistance of a patient with endometrial cancer (hereinafter abbreviated to "EC"), particularly 1st line, 2nd line, relapsed, refractory, type I or type II EC, or endometriosis, to a combination of a component A and a component B as defined herein, thus providing rationale-based dosage as defined herein to overcome said resistance of a patient with endometrial cancer (hereinafter abbreviated to "EC"), particularly 1st line, 2nd line, relapsed, refractory, type I or type II EC, or endometriosis, to a combination of a component A and a component B as defined herein (patient stratification).

EXAMPLES

The following abbreviations are used in the Examples:
Component A:
"copanlisib" or "compound A" means compound Example 13 of WO 2008/070150 A1 as shown herein (which is an example of component A as described and defined herein);
"copanlisib dihydrochloride" or "compound A*" means compound Example 1 of European patent application number EP 11 161 111.7, and in PCT application number PCT/EP2012/055600 published under WO 2012/136553, both of which are hereby incorporated herein in their entirety by reference (which is an example of component A as described and defined herein).
Component B:
"FGFRi" or "compound B" means compound Example 1 of WO 2013/087578, i.e. a compound of structure:

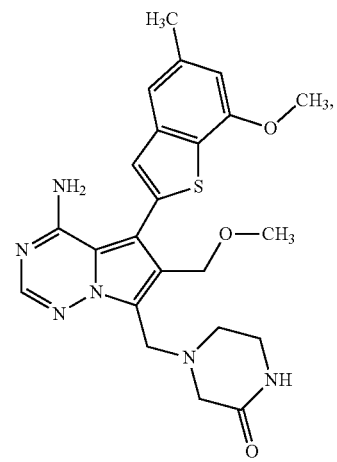 [SMILES: COCc1c(-c2cc3cc(C)cc(OC)c3s2)c2c(N)ncnn2c1CN1CCNC(=O)C1]

(which is an example of component B as described and defined herein).

Materials and Methods:

In vitro combination assessment: The effects of combinations of the present invention were evaluated using combination index isobologram analysis for in vitro assessment. The efficacy parameters were the effects in a 48-hour caspase 3/7 activation assay. Briefly, cells were plated in 384-well plate with 25 µL medium. After 24 hours, 5 µL of experimental media containing:

either A alone, or
B alone, or
the combination of A (as component A) plus either B, (as component B), at different ratios (***) were used to make serial 3-fold dilutions to generate response curves with 7 concentrations. Experiments were conducted in triplicates. Caspase 3/7 assay was conducted at 48 hours after compound exposure.

The in vivo efficacy was evaluated in tumor xenograft models in nude mice with established human tumor cell lines at the MTD and sub-MTD dosages. Tumor cells were cultivated according to ATCC protocols in recommended media contained 10% FCS. Cells were harvested for transplantation in a subconfluent (70%) state. The number of cells for inoculation was indicated in Table 1. The volume of implantation was 100 µl for mice. When the tumors were approximately in size of 25-50 mm², the animals were randomized to treatment and control groups and treatment was started. Treatment of each animal was based on individual body weight. The optimal formulation, application route and schedule were used for each compound (see table 2). Oral administration (p.o.) was carried out via a gastric tube. The oral application volumes were 10 ml/kg and the intravenous application volumes were 10 ml/kg. Tumor area (product of the longest diameter and its perpendicular) using a caliper. The animal body weight was monitored as a measure for treatment-related toxicity. Measurement of tumor area and body weight was performed 2-3 times weekly. T/C ratios (Treatment/Control) were calculated with final tumor areas. Treatment responses were evaluated by means of the clinically-used RECIST criteria (complete response, partial response, stable disease and progressive disease) and response rates were calculated accordingly (RR=number of animals with complete and partial response).

TABLE 1

Tumor models used for assessment of compound A (copanlisib) and compound B (FGFRi) in endometrial tumor models in vivo.

| Tumor model | Mode of Implantation |
| --- | --- |
| MFE 280 | s.c. implantation of 1 × 10⁶ cells suspended in 50% Matrigel into the inguinal region of female mice |

TABLE 2

Formulations, application route and schedules used in the in vivo studies.

| Drug | Formulation | Application route | Application schedule |
| --- | --- | --- | --- |
| Compound A | 5% Mannitol/0.9% NaCl | i.v. | Q2D |
| Doxorubicin | 0.9% NaCl | i.p. | Q14D |
| Compound B | 10% EtOH, 40% Solutol, 50% water (~2% HCl [2M]) | p.o. | QD |

The invention is demonstrated in the following examples which are not meant to limit the invention in any way:

Example 1. Synergistic Combination of PI3K Inhibitor Compound A (Copanlisib) and FGFR Inhibitor Compound B in MFE 280 Endometrial Tumor Model As indicated in Table 1 and in Cosmic database, endometrial cancer is a heterogeneous disease with distinct molecular characteristics. The most frequent aberration is the activation of the PI3K and loss-of-function of PTEN. It has been reported that activating mutations of FGFR2 are present in both type I and type II endometrial cancer (Pollock et al). Activating mutations in FGFR2 have been identified in approximately 10% of human endometrial carcinomas. Three out of 11 cell lines tested in vitro harbor activating FGFR2 mutation (MFE 280, MFE296 and AN3CA). Surprisingly, these 3 cell lines all have coexisting PIK3CA mutations or loss-of-function of PTEN, but no KRAS mutation.

FIG. 1: Synergistic combination of PI3K inhibitor compound A (Copanlisib) with FGFR inhibitor compound B in MFE-280 cells ($PIK3CA^{G1047Y}$, $FGFR2^{S252W}$). The combination of PI3K inhibitor compound A (copanlisib) and FGFR inhibitor compound B was tested and compared to the single agent activity in MFE 280 to address the activity in apoptosis induction using a cleaved caspase 3/7 assay. MFE 280 cells are bearing both activating PIK3CA and FGFR2 mutations. As single agent, neither Compound A nor Compound B showed apoptosis induction up to 5 and 10 µM, respectively. However when combining Compound A and Compound B, significant apoptosis was induced at sub-µM concentrations, e.g. 0.33 µM of compound A+0.44 µM compound B (FIG. 1 (A)), 0.22 µM compound A+0.66 µM compound B (FIG. 1 (B)).

Figure 2:
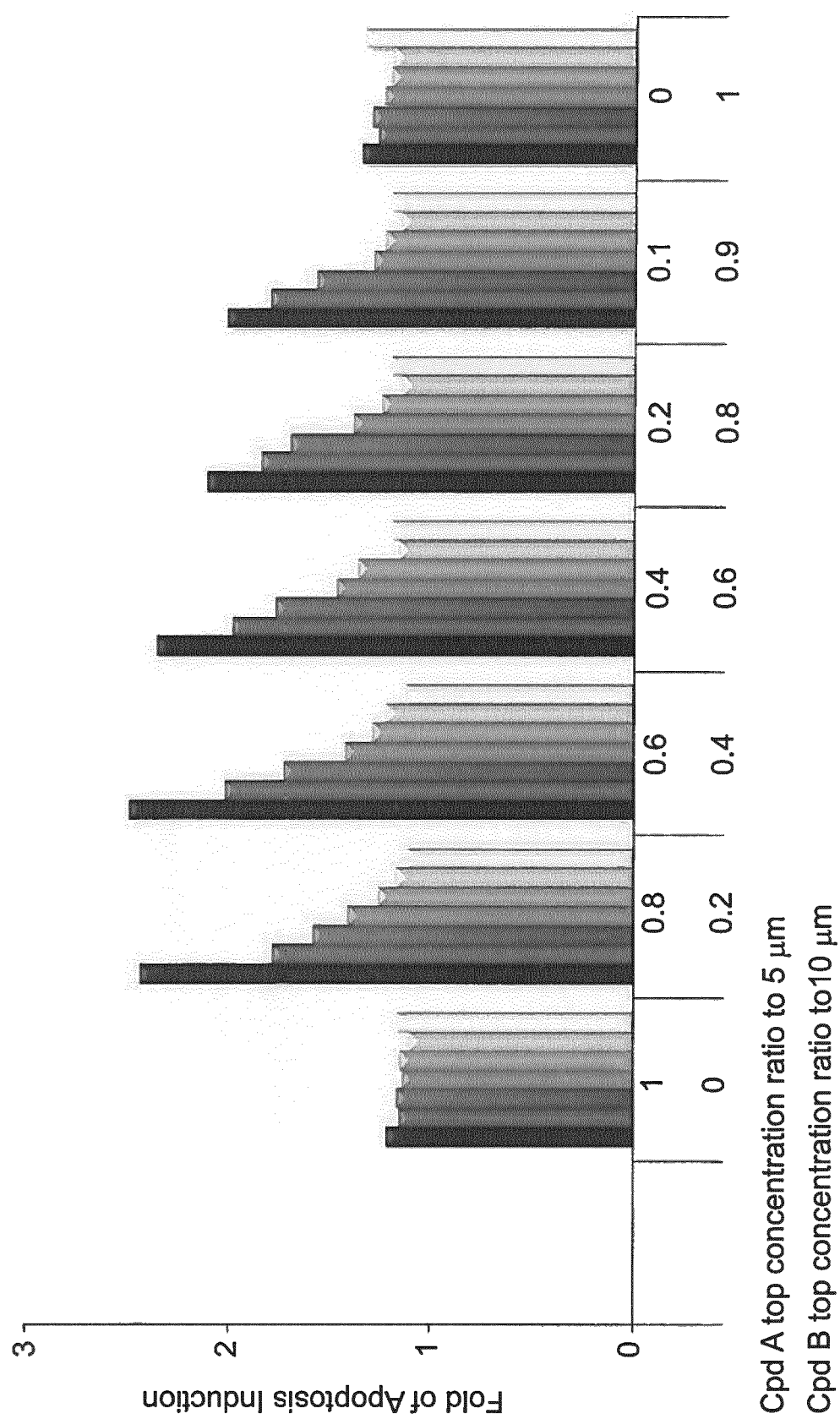
FIG. 2 shows a graph of apoptosis induction by PI3K inhibitor compound A (copanlisib) and/or FGFR inhibitor compound B in MFE-296 cells.

FIG. 2: Synergistic combination of PI3K inhibitor compound A (Copanlisib) with FGFR inhibitor compound B in MFE-296 cells ($PTEN^{del}$, $FGFR2^{N549K}$). The combination of PI3K inhibitor compound A (copanlisib) and FGFR inhibitor compound B was tested and compared to the single agent activity in MFE 296 to address the activity in apoptosis induction using a cleaved caspase 3/7 assay. MFE 296 cells are bearing activating FGFR2 mutation and loss-of-PTEN. As single agent, neither Compound A nor Compound B showed apoptosis induction up to 5 and 10 µM, respectively. However when combining Compound A and Compound B, dose-dependent apoptosis was detected by measuring activated caspase 3/7.

Figure 3A:
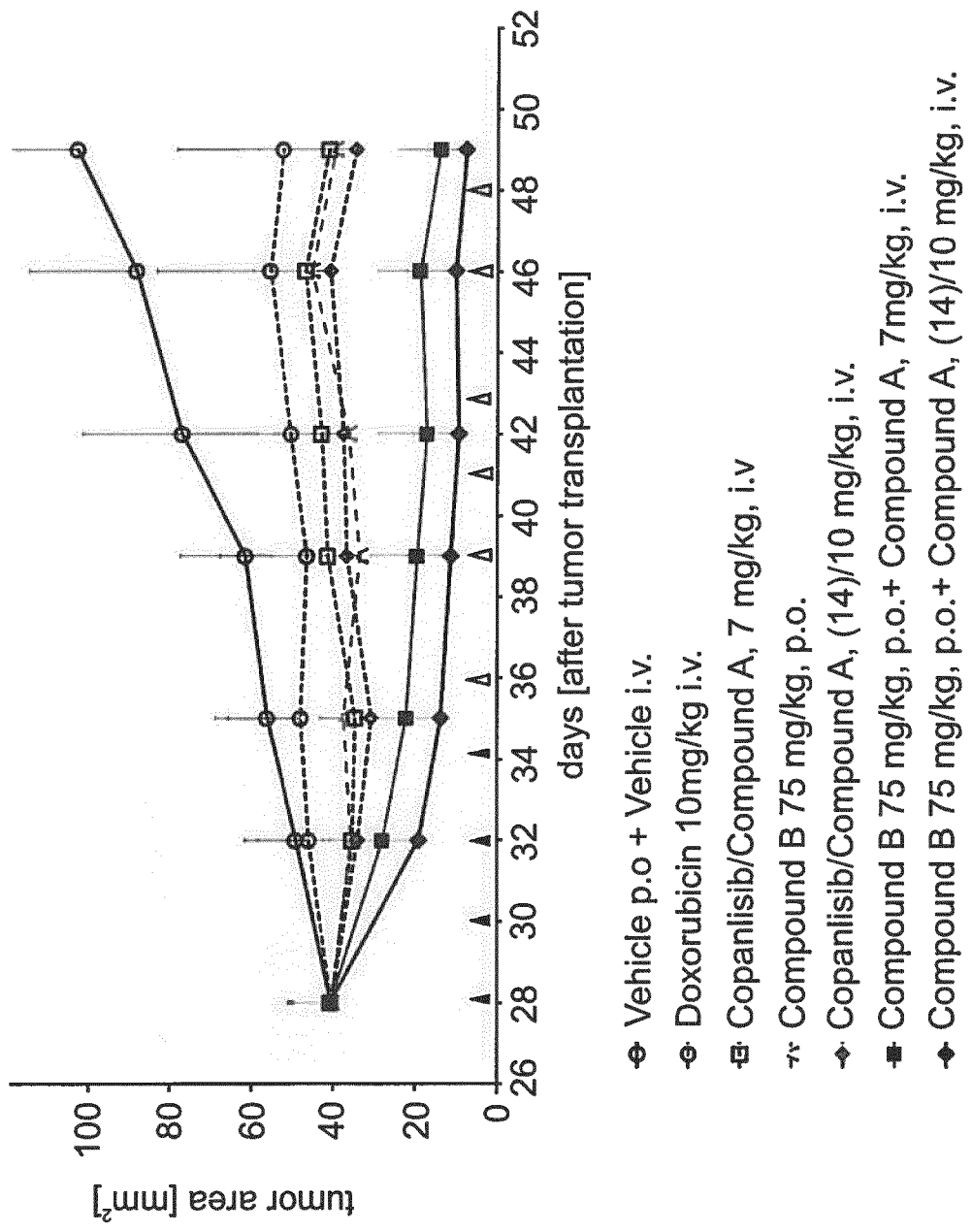
FIG. 3A shows a graph of in vivo efficacy results of PI3K inhibitor compound A (copanlisib) and/or FGFR inhibitor compound B in a MFE-280 xenograft tumor model.
Figure 3B:
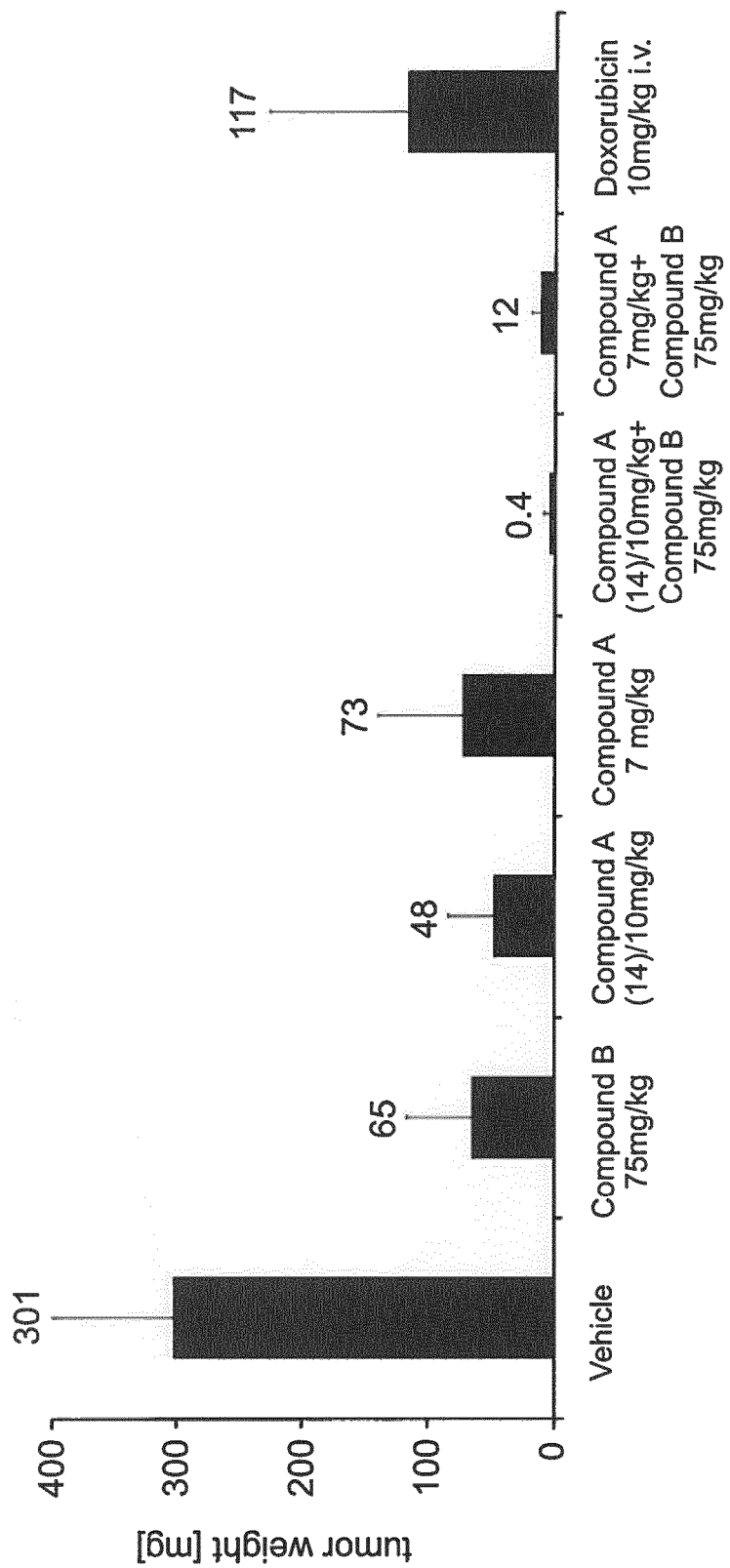
FIG. 3B shows a graph of final tumor weight results after treatment with PI3K inhibitor compound A (copanlisib) and/or FGFR inhibitor compound B in a MFE-280 xenograft tumor model.

FIGS. 3A and 3B: Synergistic combination of PI3K inhibitor compound A (Copanlisib) with FGFR inhibitor compound B in MFE-280 xenograft tumor model. The combination of PI3K inhibitor compound A (copanlisib) and FGFR inhibitor compound B was tested and compared to the

| Cell Line | IC50 (M) | Molecular features | Histological Subtype |
| --- | --- | --- | --- |
| RUCA | 1.37E−08 | $PTEN^{del}$, ER+ | Type I |
| ECC-1 | 1.61E−7 | $PTEN^{del}$, $PIK3R1^{mut}$, ER+, PR+, | |
| Ishikawa | 3.73E−07 | $PTEN^{del}$, $PIK3R1^{mut}$, ER+, PR+ | |
| HEC-50 | 6.46E−08 | $PIK3R1^{mut}$, $KRAS^{mut}$ | Type II |
| RL95-2 | 1.44E−07 | $PIK3R1^{mut}/PTEN^{del}/NF2/BRCA2/$ | |
| KLE | <6.86E−09 | $FBXW7^{mut}$ | |
| HEC-1B | <6.86E−09 | $PIK3CA^{mut}$, $PIK3R2^{mut}$, $PTEN^{Loss}$(protein) and $KRAS^{mut}$ | |
| AN3CA | <6.86E−09 | $PTEN^{del}$, FBXW7, $FGFR2^{N549K,\ K310R}$ | |
| HEC-1A | <6.86E−09 | $PIK3CA^{G1049R}$, $PIK3R2^{mut}$, $KRAS^{mut}$ | |
| MFE 280 | <6.86E−09 | $PIK3CA^{G1047Y}$, $RB^{del}$, $FGFR2^{S252W}$ | |
| MFE 296 | <6.86E−09 | $PTEN^{del}$, $FGFR2^{N549K}$, $UTX^{del}$, | | single agent activity and the SoC doxorubicin in MFE 280, an endometrial tumor model bearing both activating PIK3CA and FGFR2 mutations. At a tumor size of about 40 mm² the subcutaneously growing MFE-280 tumors were treated intravenously with two different doses of compound A (copanlisib), 14 (filled triangles)/10 (open triangles) mg/kg, and 7 mg/kg) and in combination of compound A and compound B. The dosing schedule for compound A is depicted in FIG. 3A with triangles. No body weight loss was observed compared to starting body weight in both monotherapy and combination therapy with 7 mg/kg of compound A. The dose of compound A at 14 mg/kg (filled triangles) was reduced to 10 mg/kg (open triangles) in both monotherapy and combination groups due to individual animal showed body weight loss in the combination group. Doxorubicin was applied intravenously 1 time every 14 days as a SoC reference.

Figure 4:
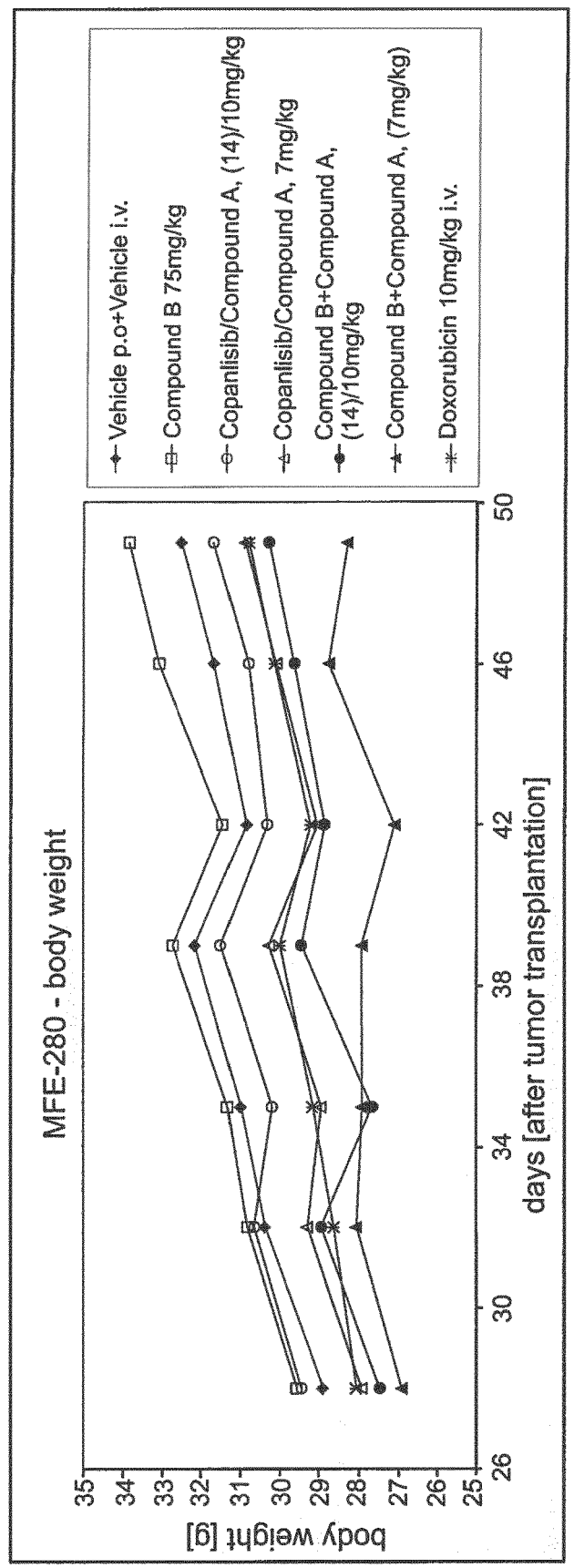
FIG. 4 shows a graph of body weight evolution over the course of treatment with PI3K inhibitor compound A (copanlisib) and/or FGFR inhibitor compound B in a MFE-280 xenograft tumor model.

Treatment of PI3K inhibitor compound A (copanlisib) led to an approximately 84% ((14)10 mg/kg) and 76% (7 mg/kg) reduction of tumor weight. FGFR inhibitor compound B also reached 78% tumor growth inhibition at the end of the study. Both inhibitors were more potent compared to the SoC Doxorubicin (61% tumor growth inhibition assessed by tumor weight). Combination of compound B with (14)10 mg/kg and 7 mg/kg compound A (copanlisib) further enhanced tumor growth inhibition to 99% and 96%, respectively. More importantly, combination therapy led to 100% response rate compared to 12.5% to 37.5% response rate in the animal groups treated with each single agent. Of note, 57% and 25% of the animals in the combination therapy groups even reached complete tumor remission (Table 3). Furthermore, combination of compound A (copanlisib 7 mg/kg) and compound B (FGFRi 75 mg/kg) was well tolerated without body weight loss during the entire treatment period, only individual body weight loss were observed with compound A (copanlisib 14 mg/kg) and compound B (FGFRi 75 mg/kg) which triggered reduction of the dose of compound A to 10 mk/kg after the fourth treatment doses (FIG. 4).

TABLE 3

Efficacy of PI3K inhibitor compound A (copanlisib) and FGFR inhibitor compound B in MFE 280 xenograft tumor model

| Treatment group | T/C[a] (tumor area) | T/C (tumor weight) | RR[b] (%) | CR[b] (%) | PR[b] (%) | SD[b] (%) | PD[b] (%) |
|---|---|---|---|---|---|---|---|
| Vehicle | 1.00 | 1.00 | 0 | 0 | 0 | 0 | 100% |
| Compound B 75 mg/kg | 0.39 | 0.22 | 12.5 | 12.5 | 0 | 75 | 12.5 |
| Compound A (14)10 mg/kg | 0.34 | 0.16 | 37.5 | 0 | 37.5 | 62.5 | 0 |
| Compound A 7 mg/kg | 0.40 | 0.24 | 25 | 0 | 25 | 50 | 25 |
| Compound A (14)10 mg/kg + Compound B 75 mg/kg | 0.07 | 0.01 | 100 | 57.1 | 42.9 | 0 | 0 |
| Compound A 7 mg/kg + Compound B 75 mg/kg | 0.14 | 0.04 | 100 | 25 | 75 | 0 | 0 |
| Doxorubicin | 0.51 | 0.39 | 12.5 | 0 | 12.5 | 50 | 37.5 |

[a]T/C = Treatment/Control ratio, Calculated from mean tumor areas or final tumor weights at the study end.
[b]Response: PD = progressive disease, the number of tumors exhibiting >20% tumor increase; SD = stable disease, the number of tumors exhibiting <30% tumor shrinkage and <20% tumor increase; PR = partial response, the number of tumors exhibiting >30% tumor shrinkage; CR = complete response, the number of not measureable tumors.

Example 2. Clinical Benefit of PI3K Inhibitor Compound A (Copanlisib) in Endometrial Cancer Patients In a phase I dose escalation study, subjects were treated with Compound A (copanlisib) administered intravenously over 60 minutes on days 1, 8, and 15 of every 28 day cycle. Seventeen subjects were treated in 5 dose escalation cohorts (0.1, 0.2, 0.4, 0.8, and 1.2 mg/kg), and the maximum tolerated dose (MTD) was determined to be 0.8 mg/kg. Additional patients were enrolled into the study in 3 expansion cohorts treated at the MTD to assess safety, pharmacokinetics, biomarkers, and clinical benefit in selected patient populations, including solid tumors (n=25), non-Hodgkin lymphoma (NHL; n=9), and diabetic solid tumor patients (n=6; treated at 0.4 mg/kg). Clinical benefit (patients experiencing complete response [CR], partial response [PR], or stable disease [SD]) was observed in 4 of 5 (80%) endometrial cancer patients treated in this study (Table 4), including one patient with CR and 2 with extended SD lasting more than 8 cycles (more than 224 days).

PIK3CA, BRAF, and KRAS mutations were tested using digital PCR on archival tumor samples and cell free DNA isolated from plasma. Next generation sequencing (NGS) of a panel of tumor genes and immunohistochemistry (IHC) for PTEN protein were also performed on archival tumor samples. Of note, the sole patient in the study with a CR had an endometrial cancer with PTEN loss by IHC and mutations in both the PTEN and PIK3CA genes (Table 4). Of the 2 endometrial cancer patients with extended SD lasting more than 8 cycles, PTEN data could only be generated for 1 (patient #2117), and this tumor was also PTEN-negative by IHC (Table 4). The other endometrial cancer patient with extended SD (with 24.3% tumor shrinkage) harbored a KRAS tumor mutation (Table 4). This data shows that Compound A (copanlisib) may provide clinical benefit to patients with endometrial cancer either with or without PIK3CA mutations, with or without PTEN loss or mutation, and with or without mutations in KRAS. Activation of PI3K pathway signaling via a number of mechanisms alone or in combination, such as PTEN loss and/or mutation, PIK3CA mutation, and/or KRAS mutation, may enrich Compound A (copanlisib) activity in this population.

TABLE 4

Clinical outcomes and biomarker data among endometrial cancer patients treated in a phase I study of Compound A (copanlisib)

| Pt # | Nb Prior Systemic Anti-cancer Therapy (setting) | Stage At Study Entry | Compound A (copanlisib) dose | Best response | Best % change in tumor size from screening | PIK3CA mutation status | PTEN mutation status | PTEN protein (IHC, % of cells positive) | BRAF mutation status | KRAS mutation status |
|---|---|---|---|---|---|---|---|---|---|---|
| 2004 | 2 (adjuvant) | IV | 0.4 mg/kg (40 mg) | SD 8 cycles | −24.3 | WT | Nd | nd | WT | MUT |
| 2008 | 2 (adjuvant) | IV | 0.8 mg/kg (40 mg) | PD | 2.4 | MUT (H1047R) | Nd | nd | WT | WT |
| 2116 | 2 (palliative) | IV | 0.8 mg/kg (59 mg) | SD 2 cycles | −8.7 | WT | Nd | 25% (PTEN-positive) | WT | WT |
| 2117 | 2 (adjuvant) | IIIC | 0.8 mg/kg (51 mg) | SD 8 cycles | −9.1 | WT | Nd | 0% (PTEN-negative) | WT | WT |
| 3106 | 0* (adjuvant) | IV | 0.8 mg/kg (46 mg, then 37 mg°) | CR# | −61.8 | MUT (T1052K/ R88L) | MUT | 0% (PTEN-negative) | WT | WT |

Pt, patient; WT, wild-type; MUT, mutant; nd, not done
*Only surgery, patient declined adjuvant chemotherapy and radiation
PR at end of cycle 2 until end of cycle 8, then CR until end of cycle 14
°Dose reduction at cycle 5 due to adverse event These findings provide a rationale to develop personalized therapies for the treatment of endometrial cancer (hereinafter abbreviated to "EC"), particularly 1st line, 2nd line, relapsed, refractory, type I or type II EC, or endometriosis.

Hence, as mentioned supra, the present invention relates to the use of biomarkers which is the loss of tumor suppressor PTEN or FBXW7, either alone or in combination with another form of PI3K pathway activation (as described in the next paragraph), for predicting the sensitivity and/or resistance of a patient with endometrial cancer (hereinafter abbreviated to "EC"), particularly 1st line, 2nd line, relapsed, refractory, type I or type II EC, or endometriosis, to a 2,3-dihydroimidazo[1,2-c]quinazoline compound as defined herein, thus providing rationale-based dosage as defined herein to overcome resistance (patient selection or stratification). Other forms of PI3K pathway activation include, but are not limited to, perturbation of any of the following alone or in combination: mutation in PIK3CA, PIK3CB, PIK3CD, PIK3CG, PIK3R1, PIK3R2, PIK3R3, PIK3R4, PIK3R5, FGFR1, FGFR2, FGFR3 and/or FGFR4. PTEN loss and alteration of PIK3CA, PIK3CB, PIK3CD, PIK3CG, PIK3R1, PIK3R2, PIK3R3, PIK3R4, PIK3R5, FGFR1, FGFR2, FGFR3 and/or FGFR4 may be measured at either the protein level, mRNA level, or DNA level.

In accordance with an embodiment, the present invention relates to a method of determining the loss of tumor suppressor PTEN or FBXW7.

In accordance with another embodiment, the present invention relates to a method for determining perturbations in PIK3CA, PIK3CB, PIK3CD, PIK3CG, PIK3R1, PIK3R2, PIK3R3, PIK3R4, PIK3R5, FGFR1, FGFR2, FGFR3 and/or FGFR4. PTEN loss and alteration o of PIK3CA, PIK3CB, PIK3CD, PIK3CG, PIK3R1, PIK3R2, PIK3R3, PIK3R4, PIK3R5, FGFR1, FGFR2, FGFR3 and/or FGFR4.

The invention claimed is:
1. A combination of:
   component A: 2-amino-N-[7-methoxy-8-(3-morpholin-4-ylpropoxy)-2,3-dihydroimidazo[1,2-c]quinazolin-5-yl]pyrimidine-5-carboxamide,
   or a physiologically acceptable salt, solvate, hydrate or stereoisomer thereof, optionally in the form of a pharmaceutical formulation which is ready for use to be administered simultaneously, concurrently, separately or sequentially;
   and
   component B: 4-{[4-Amino-6-(methoxymethyl)-5-(7-methoxy-5-methyl-1-benzothiophen-2-yl)pyrrolo[2,1-f][1,2,4]triazin-7-yl]methyl}piperazin-2-one,
   or a physiologically acceptable salt, solvate, hydrate or stereoisomer thereof, optionally in the form of a pharmaceutical formulation which is ready for use to be administered simultaneously, concurrently, separately or sequentially.

2. The combination according to claim 1, wherein said component A is:
   2-amino-N-[7-methoxy-8-(3-morpholin-4-ylpropoxy)-2,3-dihydroimidazo[1,2-c]quinazolin-5-yl]pyrimidine-5-carboxamide.

3. The combination according to claim 1, wherein said component A is:
   2-amino-N-[7-methoxy-8-(3-morpholin-4-ylpropoxy)-2,3-dihydroimidazo[1,2-c]quinazolin-5-yl]pyrimidine-5-carboxamide dihydrochloride.

4. The combination according to claim 1, wherein said component B is:
   4-{[4-Amino-6-(methoxymethyl)-5-(7-methoxy-5-methyl-1-benzothiophen-2-yl)pyrrolo[2,1-f]-[1,2,4]triazin-7-yl]methyl}piperazin-2-one.

5. The combination according to claim 1, wherein said component A is:
   2-amino-N-[7-methoxy-8-(3-morpholin-4-ylpropoxy)-2,3-dihydroimidazo[1,2-c]quinazolin-5-yl]pyrimidine-5-carboxamide; and
   said component B is:
   4-{[4-Amino-6-(methoxymethyl)-5-(7-methoxy-5-methyl-1-benzothiophen-2-yl)pyrrolo[2,1-f]-[1,2,4]triazin-7-yl]methyl}piperazin-2-one.

6. The combination according to claim 1, wherein said component A is:
   2-amino-N-[7-methoxy-8-(3-morpholin-4-ylpropoxy)-2,3-dihydroimidazo[1,2-c]quinazolin-5-yl]pyrimidine-5-carboxamide dihydrochloride; and said component B is:

4-{[4-Amino-6-(methoxymethyl)-5-(7-methoxy-5-methyl-1-benzothiophen-2-yl)pyrrolo[2,1-f]-[1,2,4]triazin-7-yl]methyl}piperazin-2-one.

7. A method of treatment of endometrial cancer in a subject, comprising administering to said subject a therapeutically effective amount of the combination according to claim 1.

8. The method according to claim 7, wherein said endometrial cancer is selected from the group consisting of 1st line, 2nd line, relapsed, refractory, type I or type II endometrial cancer, and endometriosis.

9. The method according to claim 7, wherein said endometrial cancer is 1st line, 2nd line, relapsed, refractory, or type I endometrial cancer.

10. The method according to claim 7, wherein said endometrial cancer is 1st line, 2nd line, relapsed, refractory, type II endometrial cancer, or endometriosis.

11. A kit comprising the combination according to claim 1, wherein optionally both or either of said components A and B are in the form of a pharmaceutical formulation which is ready for use to be administered simultaneously, concurrently, separately or sequentially.

12. The kit according to claim 11, wherein:

said component A is: 2-amino-N-[7-methoxy-8-(3-morpholin-4-ylpropoxy)-2,3-dihydroimidazo[1,2-c]quinazolin-5-yl]pyrimidine-5-carboxamide; and said component B is 4-{[4-Amino-6-(methoxymethyl)-5-(7-methoxy-5-methyl-1-benzothiophen-2-yl)pyrrolo[2,1-f][1,2,4]triazin-7-yl]methyl}piperazin-2-one.

13. The kit according to claim 11, wherein:

said component A is: 2-amino-N-[7-methoxy-8-(3-morpholin-4-ylpropoxy)-2,3-dihydroimidazo[1,2-c]quinazolin-5-yl]pyrimidine-5-carboxamide dihydrochloride; and said component B is: 4-{[4-Amino-6-(methoxymethyl)-5-(7-methoxy-5-methyl-1-benzothiophen-2-yl)pyrrolo[2,1-f][1,2,4]triazin-7-yl]methyl}piperazin-2-one.

* * * * *